(12) United States Patent
Harriott et al.

(10) Patent No.: US 11,040,970 B2
(45) Date of Patent: Jun. 22, 2021

(54) VMAT2 INHIBITOR COMPOUNDS AND COMPOSITIONS THEREOF

(71) Applicant: Neurocrine Biosciences, Inc., San Diego, CA (US)

(72) Inventors: Nicole Harriott, San Diego, CA (US); Donald Hettinger, San Diego, CA (US); Shawn Branum, San Diego, CA (US); Jeffrey C. Culhane, San Diego, CA (US)

(73) Assignee: Neurocrine Biosciences, Inc., San Diego, CA (US)

(*) Notice: Subject to any disclaimer, the term of this patent is extended or adjusted under 35 U.S.C. 154(b) by 0 days.

(21) Appl. No.: 16/606,191

(22) PCT Filed: Apr. 17, 2018

(86) PCT No.: PCT/US2018/028031
§ 371 (c)(1),
(2) Date: Oct. 17, 2019

(87) PCT Pub. No.: WO2018/195121
PCT Pub. Date: Oct. 25, 2018

(65) Prior Publication Data
US 2020/0131173 A1 Apr. 30, 2020

Related U.S. Application Data

(60) Provisional application No. 62/487,413, filed on Apr. 19, 2017, provisional application No. 62/652,837, filed on Apr. 4, 2018.

(51) Int. Cl.
| C07D 487/04 | (2006.01) |
| A61K 31/495 | (2006.01) |
| A61P 25/00 | (2006.01) |
| C07D 471/04 | (2006.01) |

(52) U.S. Cl.
CPC ................ *C07D 471/04* (2013.01)

(58) Field of Classification Search
CPC ...... C07D 487/04; A61K 31/495; A61P 25/00
See application file for complete search history.

(56) References Cited

U.S. PATENT DOCUMENTS

| 5,798,119 | A | 8/1998 | Herbig et al. |
| 8,039,627 | B2 | 10/2011 | Gano |
| 2008/0188460 | A1 | 8/2008 | Casara et al. |
| 2012/0077839 | A1 | 3/2012 | Gano |
| 2015/0080416 | A1 | 3/2015 | Lu et al. |
| 2016/0289226 | A1 | 10/2016 | Ashweek et al. |

FOREIGN PATENT DOCUMENTS

| WO | WO 02/072584 | 9/2002 |
| WO | WO 2005/000846 | 1/2005 |
| WO | WO 2008/058261 | 5/2008 |
| WO | WO 2015/120317 | 8/2015 |
| WO | WO 2016/127133 | 8/2016 |
| WO | WO 2018/119224 | 6/2018 |
| WO | WO 2018/119266 | 6/2018 |
| WO | WO 2010/044981 | 4/2020 |

OTHER PUBLICATIONS

Bystritsky, "Treatment-resistant anxiety disorders," Mol. Psychiatry, 2006, 11:805-814.
Collier et al., "Radiosynthesis and in-vivo evaluation of the pseudopeptide s-opioid antagonist," J. Labelled Compd. Radiopharm., 1999, 42:S264-S266.
Corvin, "Two patients walk into a clinic . . . a genomics perspective on the future of schizophrenia," BMC Biol., 2011, 9: 77.
Hoare et al., "Conformational states of the corticotropin releasing factor 1 (CRF1) receptor: detection, and pharmacological evaluation by peptide ligands," Peptides, 2003, 24(12):1881-97.
International Preliminary Report on Patentability in Application No. PCT/US2018/028031, dated Oct. 22, 2019, 6 pages.
Khalsa et al., Treatment-resistant OCD: options beyond first-line medications,: Curr. Psychiatry, 2011, 10:45-52.
Kolzer et al., "Synthesis of Bioactive 2-Aza-Analogues of Ipecac and Alangium Alkaloids," 2010, 5:1456-1464.
Le Bas et al., "Radioiodinated analogs of EP 00652218 for the exploration of the tachykinin nk1 receptor by spect," J. Labelled Compd. Radiopharm. 2001, 44:S280-S282.
Login et al., "Tetrabenazine has properties of a dopamine receptor antagonist," Ann. Neurology, 1982, 12:257-62.
Near, "[3H]Dihydrotetrabenazine binding to bovine striatal synaptic vesicles," Mol. Pharmacol., 1986, 30(2):252-57.
Pallanti and Quercioli, "Treatment-refractory obsessive-compulsive disorder: methodological issues, operational definitions and therapeutic lines," Neuropsychopharmacol. Biol. Psychiatry, 2006, 30:400-412.
Pettibone et al., "Tetrabenazine-induced depletion of brain monoamines: Mechanism by which desmethylimipramine protects cortical ," Eur. J. Pharmacol., 1984, 102:431-6.

(Continued)

*Primary Examiner* — Bruck Kifle
(74) *Attorney, Agent, or Firm* — Fish & Richardson P.C.

(57) ABSTRACT

Provided is a compound selected from compounds of Formula (I) and pharmaceutically acceptable salts, solvates, and hydrates thereof: (I) wherein $R^1$, $R^2$, $R^3$ and $R^4$ are as defined herein. Such compounds are inhibitors of the vesicular monoamine transporter 2 (VMAT2) and have utility for treating, for example, neurological and psychiatric diseases and disorders. Also disclosed are compositions containing such compounds in combination with a pharmaceutically acceptable carrier, as well as methods relating to their use in subjects in need thereof.

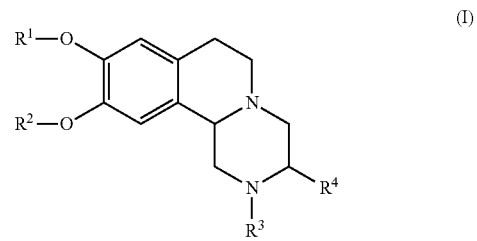

29 Claims, No Drawings

(56) References Cited

OTHER PUBLICATIONS

Reches et al., "Tetrabenazine, an amine-depleting drug, also blocks dopamine receptors in rat brain," J. Pharmacol. Exp. Ther., 1983, 225:515-521.
Scherman et al., "Characterization of the monoamine carrier of chromaffin granule membrane by binding of [2-3H]dihydrotetrabenazine," Proc. Natl. Acad. Sci. USA, 1983, 80:584-8.
Teng et al., "Lobeline displaces [3H]dihydrotetrabenazine binding and releases [3H]doparnine from. rat striatal synaptic vesicles: comparison with d-amphetamine," J Neurochem., 1998, 71(1):258-65.
Verkerk et al., "Identification of a gene (FMR-1) containing a CGG repeat coincident with a breakpoint cluster region exhibiting length variation in fragile X syndrome," Cell, 1991, 65:905-14.
Wadenberg et al., "The conditioned avoidance response test re-evaluated: is it a sensitive test for the detection of potentially atypical antipsychotics?," Biobehav. Rev., 1999, 23(6):851-62.
Yamazaki et al.. "Synthesis in Azabenzoquinolizine Group. III. Synthesis of 9, 1 O-Dimethoxy-1,2,3,4,6, 7-hexahydro-11 bH-pyrimido( 4,3-aJisoquinoline Derivatives," Pharmaceutical Faculty, University of Toyama, 1959, 79(8):1008-1013.
Zhu et al., "Synthesis and Mode of Action of 125I- and 3H-Labeled Thieno[2,3-c]pyridine Antagonists of Cell Adhesion Molecule Expression," J. Org. Chem., 2002, 67(3):943-948.

VMAT2 INHIBITOR COMPOUNDS AND COMPOSITIONS THEREOF

This disclosure relates generally to VMAT2 inhibitor compounds, compositions and methods related thereto.

Dysregulation of dopaminergic systems is integral to several central nervous system (CNS) disorders, including neurological and psychiatric diseases and disorders. These neurological and psychiatric diseases and disorders include hyperkinetic movement disorders, and conditions such as schizophrenia and mood disorders. The transporter protein vesicular monoamine transporter-2 (VMAT2) plays an important role in presynaptic dopamine release and regulates monoamine uptake from the cytoplasm to the synaptic vesicle for storage and release.

3-Isobutyl-9,10-dimethoxy-1,3,4,6,7,11b-hexahydro-2H-pyrido[2,1-a]-isoquinolin-2-one, also known as tetrabenazine (TBZ), has been used as a drug for decades. Tetrabenazine is a potent, reversible inhibitor of catecholamine uptake by vesicular monoamine transporter-2 (VMAT2) ($IC_{50}$=3.2 nM) (see, e.g., Scherman et al., *Proc. Natl. Acad. Sci. USA*, (1983) 80:584-8) and is currently used in the treatment of various hyperkinetic disorders. Side effects associated with TBZ include sedation, depression, akathisia and Parkinsonism. Inhibition of VMAT2 by TBZ results in depletion of brain monoamines in vivo (see, e.g., Pettibone et al., *Eur. J. Pharmacol.* (1984) 102:431-6). TBZ also inhibits presynaptic and postsynaptic dopamine receptors in rat brain (see, e.g., Login et al., (1982) *Ann. Neurology* 12:257-62; Reches et al., *J. Pharmacol. Exp. Ther.* (1983) 225:515-521). This off-target activity of TBZ may be responsible for some of the observed side effects.

Despite the advances that have been made in this field, a need remains in the art for improved VMAT2 inhibitors, including compounds, compositions, and methods related thereto. The present disclosure fulfills these and other needs, as evident in reference to the following disclosure.

BRIEF SUMMARY

Provided are vesicular monoamine transporter 2 (VMAT2) inhibitors, as well compositions and methods of use related thereto.

Provided is a compound selected from compounds of Formula (I) and pharmaceutically acceptable salts, solvates, and hydrates thereof:

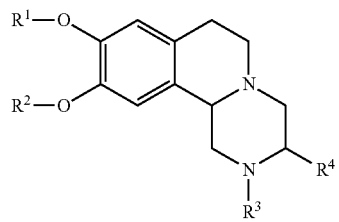

(I)

wherein:
$R^1$ and $R^2$ are independently lower alkyl, lower cycloalkyl, or lower cycloalkylalkyl, wherein each lower alkyl, lower cycloalkyl, and lower cycloalkylalkyl is independently unsubstituted or substituted with one or more halo, cyano, or lower alkoxy;
$R^3$ is lower alkyl; and
$R^4$ is lower alkyl or lower cycloalkylalkyl.

Also provided is a pharmaceutical composition comprising one or more compounds described herein in combination with one or more pharmaceutically acceptable excipients and/or diluents.

Also provided are methods for treating diseases, disorders, or conditions that benefit from inhibiting VMAT2. Also provided are methods for treating neurological and/or psychiatric diseases and disorders in a subject in need thereof by administering to the subject in need thereof a pharmaceutically effective amount of one or more compounds described herein, or a pharmaceutical composition comprising the same.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

Terms not specifically defined herein should be given the meanings that would be given to them by one of skill in the art in light of the disclosure and the context. As used in the specification, however, unless specified to the contrary, the terms have the meaning indicated.

In the following description, certain specific details are set forth in order to provide a thorough understanding of various embodiments. However, one skilled in the art will understand that the present compounds may be made and used without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising," are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

As used in the specification and appended claims, unless specified to the contrary, the following terms have the meaning indicated.

"VMAT2" refers to human vesicular monoamine transporter isoform 2, an integral membrane protein that acts to transport monoamines, particularly neurotransmitters such as dopamine, norepinephrine, serotonin, and histamine, from cellular cytosol into synaptic vesicles.

The term "VMAT2 inhibitor", "inhibit VMAT2", or "inhibition of VMAT2" refers to the ability of a compound disclosed herein to alter the function of VMAT2. A VMAT2 inhibitor may block or reduce the activity of VMAT2 by forming a reversible or irreversible covalent bond between the inhibitor and VMAT2 or through formation of a noncovalently bound complex. Such inhibition may be manifest only in particular cell types or may be contingent on a particular biological event. The term "VMAT2 inhibitor", "inhibit VMAT2", or "inhibition of VMAT2" also refers to altering the function of VMAT2 by decreasing the probability that a complex forms between a VMAT2 and a natural substrate.

The subject in need of the compositions and methods described herein includes a subject who has been diagnosed by a person skilled in the medical and psychiatric arts with a neurological and/or psychiatric diseases and disorder, including a hyperkinetic movement disorder (e.g., tardive dyskinesia). A subject (or patient) to be treated may be a mammal, including a human or non-human primate. The mammal may be a domesticated animal such as a cat or a dog.

As understood by a person skilled in the medical art, the terms, "treat" and "treatment," refer to medical management of a disease, disorder, or condition of a subject (i.e., patient) (see, e.g., Stedman's Medical Dictionary). The terms "treatment" and "treating" embraces both preventative, i.e. prophylactic, or therapeutic, i.e. curative and/or palliative, treatment. Thus the terms "treatment" and "treating" comprise therapeutic treatment of patients having already developed the condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods described herein may be used, for instance, as therapeutic treatment over a period of time as well as for chronic therapy. In addition, the terms "treatment" and "treating" comprise prophylactic treatment, i.e., a treatment of patients at risk to develop a condition mentioned hereinbefore, thus reducing the risk.

Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disorder. Prophylactic administration of a composition herein may commence upon first treatment with dopamine receptor blocking drugs such as neuroleptics. As discussed herein, beneficial or desired clinical results from treating a subject include, but are not limited to, abatement, lessening, or alleviation of symptoms that result from or are associated the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the condition or disorder as well as subjects prone to have or at risk of developing the disease, condition, or disorder (e.g., TD or other conditions or disorders described herein), and those in which the disease, condition, or disorder is to be prevented (i.e., decreasing the likelihood of occurrence of the disease, disorder, or condition). A therapeutically effective amount of any one of the VMAT2 inhibitors described herein in the amount of the VMAT2 inhibitor that provides a statistically or clinically significant therapeutic and/or prophylactic benefit to the treated subject.

Methods for determining the effectiveness of a therapeutic for treating neurological and psychiatric diseases and disorders are routinely practiced in the art by a person skilled in the medical and clinical arts. By way of example, a subject with a hyperkinetic movement disorder may be diagnosed, monitored, and evaluated by the Abnormal Involuntary Movement Scale (AIMS). The AIMS is a structured neurological examination that was developed in 1976 and has been used extensively in movement disorder assessments. It consists of seven distinct ratings of regional involuntary body movements that are scored on a zero to four scale with zero being rated as none and four being rated as severe.

"Monotherapy" refers to to the administration of a single active or therapeutic compound to a subject in need thereof. In some embodiments, monotherapy will involve administration of a therapeutically effective amount of a compound described herein. Monotherapy may be contrasted with combination therapy, in which a combination of multiple active compounds is administered, such as with each component of the combination present in a therapeutically effective amount.

"Maintenance therapy" refers to treatment given to patients to enable them, e.g., to stay in remission, to maintain their health in a disease-free, or limited-disease, state. Maintenance medications are typically taken for a prolonged period of time.

"Adjunctive therapy" refers to a treatment that is used in conjunction with a primary treatment and its purpose is to assist the primary treatment. Adjunctive therapies are co-administered therapies. For example, if Obsessive-Compulsive Disorder is being treated, the primary therapy may be, e.g., an antidepressant, and the co-administration of a compound described herein would be considered an adjunctive therapy.

"Lower alkyl" refers to a straight or branched hydrocarbon chain radical consisting solely of carbon and hydrogen atoms, saturated or unsaturated, having from one to eight carbon atoms (C1-8), or one to six carbon atoms (C1-6) in a more specific embodiment, or one to four carbon atoms (C1-4) in a more specific embodiment, and which is attached to the rest of the molecule by a single bond. Fully saturated lower alkyls include, but are not limited to, methyl, ethyl, n-propyl, iso-propyl, n-butyl, t-butyl, n-pentyl, iso-pentyl, neo-pentyl, n-hexyl, 2-methylpentyl, 3-methylpentyl, 2,3-dimethylbutyl, 2,2-dimethylbutyl, and the like. Unsaturated lower alkyls include, but are not limited to, any of the above listed saturated lower alkyls containing at least one double bond between adjacent carbon atoms, such as ethenyl, prop-1-enyl, but-1-enyl, pent-1-enyl, penta-1,4-dienyl, and the like.

"Lower cycloalkyl" refers to a non-aromatic monocyclic hydrocarbon radical consisting solely of carbon and hydrogen atoms having from three to eight carbon atoms, or three to six carbon atoms (C3-6) in a more specific embodiment, or three or four carbon atoms ($C_3$ or $C_4$) in a more specific embodiment, which is saturated or unsaturated, and attached to the rest of the molecule by a single bond. Such radicals include, but are not limited to, cyclopropyl, cyclobutyl, cyclopentyl and cyclohexyl.

"Lower cycloalkylalkyl" refers to a lower alkyl as defined above wherein a hydrogen atom is replaced with a lower cycloalkyl radical as defined above. Such radicals include, but are not limited to, —$CH_2$-cyclopropyl, —$CH_2$-cyclobutyl, —$CH_2$-cyclopentyl and the like.

"Lower alkoxy" refers to the radical —O(lower alkyl), wherein lower alkyl is as defined above.

"Cyano" refers to the —CN radical.

"Halo" refers to bromo, chloro, fluoro or iodo.

With regard to stereoisomers, the compounds described herein have multiple chiral (or asymmetric) centers which give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans). Likewise, unless otherwise indicated, all possible isomers, as well as their racemic and optically pure forms, and all tautomeric forms are also intended to be included. It is therefore contemplated that various stereoisomers and mixtures thereof include "enantiomers," which refers to two stereoisomers whose molecules are nonsuperimposeable mirror images of one another. Thus, the compounds may occur in any isomeric form, including racemates, racemic mixtures, and as individual enantiomers or diastereomers.

Accordingly, it is understood that the present invention embraces each diastereoisomer, each enantiomer and mixtures thereof of each compound and generic formula disclosed herein just as if they were each individually disclosed with the specific stereochemical designation for each chiral carbon. Separation of the individual isomers (such as, by chiral HPLC, recrystallization of diastereoisomeric mixtures and the like) or selective synthesis (such as, by enantiomeric selective syntheses and the like) of the individual isomers is accomplished by application of various methods which are well known to practitioners in the art.

Additionally, individual compounds and chemical genera of the present invention encompass all pharmaceutically acceptable salts, solvates, and hydrates, thereof.

It is understood that when the phrase "pharmaceutically acceptable salts, solvates, and hydrates" or the phrase "pharmaceutically acceptable salt, solvate, or hydrate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate or hydrate" is used when referring to salts described herein, it embraces pharmaceutically acceptable solvates and/or hydrates of such salts.

The compounds described herein may generally be utilized as the free acid or free base. Alternatively, the compounds may be used in the form of acid or base addition salts. Acid addition salts of a free amino group may be prepared by methods well known in the art, and may be formed from organic and inorganic acids. Suitable organic acids include maleic, fumaric, benzoic, ascorbic, succinic, methanesulfonic, p-toluenesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, a "pharmaceutically acceptable salt" is intended to encompass any and all acceptable salt forms, including mono- and di-salt forms.

The compounds described herein may exist in a continuum of solid states ranging from fully amorphous to fully crystalline. Furthermore, some of the compounds described herein may exist as polymorphs.

In addition, some of the compounds may also form solvates with water or other organic solvents. The term "solvate" is used herein to describe a molecular complex comprising a compound described herein and one or more pharmaceutically acceptable solvent molecules. When the solvent molecule is water, the molecular complex is referred to as a "hydrate". Such hydrates and solvates are similarly included within the scope of this disclosure.

As one of skill in the art would appreciate, any of the compounds described herein may incorporate isotopes. Accordingly, also provided are radiolabeled compounds that would be useful not only in radio-imaging but also in assays, both in vitro and in vivo, for localizing and quantitating receptors in tissue samples, including human and for identifying receptor ligands by inhibition binding of a radiolabeled compound. It is a further object of this invention to develop novel receptor assays of which comprise such radiolabeled compounds.

These isotopically-labeled compounds are otherwise identical to those described herein, wherein one or more atoms are replaced by an atom having an atomic mass or mass number different from the atomic mass or mass number usually found in nature. Examples of isotopes that can be incorporated into these compounds include isotopes of hydrogen, carbon, nitrogen, oxygen, fluorine and chlorine, such as, but not limited to, $^2$H, $^3$H, $^{13}$C, $^{14}$C, $^{15}$N, $^{18}$O, $^{17}$O, $^{18}$F, and $^{36}$Cl. Certain isotopically-labeled compounds, for example those into which radioactive isotopes such as $^3$H and $^{14}$C are incorporated, are also useful in drug or substrate tissue distribution assays. Tritiated hydrogen ($^3$H) and carbon-14 ($^{14}$C) isotopes are particularly preferred for their ease of preparation and detectability. Substitution with heavier isotopes such as deuterium ($^2$H or D) can provide certain therapeutic advantages resulting from greater metabolic stability, for example increased in vivo half-life or reduced dose requirements and, therefore, may be preferred in some circumstances. Isotopically-labeled compounds can generally be prepared by performing procedures routinely practiced in the art.

The present disclosure includes all isotopes of atoms occurring in the present compounds, intermediates, salts and crystalline forms thereof. Isotopes include those atoms having the same atomic number but different mass numbers. One aspect of the present invention includes every combination of one or more atoms in the present compounds, intermediates, salts, and crystalline forms thereof that is replaced with an atom having the same atomic number but a different mass number. One such example is the replacement of an atom that is the most naturally abundant isotope, such as $^1$H or $^{12}$C, found in one the present compounds, intermediates, salts, and crystalline forms thereof, with a different atom that is not the most naturally abundant isotope, such as $^2$H or $^3$H (replacing $^1$H), or $^{11}$C, $^{13}$C, or $^{14}$C (replacing $^{12}$C). Accordingly, one aspect of the present invention includes every combination of one or more hydrogen atoms in the present compounds, intermediates, salts, and crystalline forms thereof that is replaced with a deuterium. A compound wherein such a replacement has taken place is commonly referred to as being an isotopically-labeled compound. Isotopic-labeling of the present compounds, intermediates, salts, and crystalline forms thereof can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2$H (deuterium) and $^3$H (tritium). Isotopes of carbon include $^{11}$C, $^{13}$C, and $^{14}$C. Isotopes of nitrogen include $^{13}$N and $^{15}$N. Isotopes of oxygen include $^{15}$O, $^{17}$O, and $^{18}$C. Isotope of fluorine include $^{18}$F. Isotopes of phosphorous include $^{32}$P and $^{33}$P. Isotopes of sulfur include $^{35}$S. Isotopes of chlorine include $^{36}$Cl. Isotopes of bromine include $^{75}$Br, $^{76}$Br, $^{77}$Br, and $^{82}$Br. Isotopes of iodine include $^{123}$I, $^{124}$I, $^{125}$I, and $^{131}$I.

Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present compounds, intermediates, salts, and crystalline forms thereof, wherein the naturally occurring distribution of the isotopes in the composition is perturbed. Another aspect of the present invention includes compositions and pharmaceutical compositions comprising compounds as described herein wherein the compound is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Certain isotopically-labeled compounds of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Examples by substituting an isotopically labeled reagent for a non-isotopically labeled reagent. Other synthetic methods that are useful are discussed below. Moreover, it should be understood that all of the atoms represented in the compounds of the invention can be either the most commonly occurring isotope of such atoms or a scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A representative procedure was reported by Zhu, G-D. and co-workers in J. Org. Chem., 2002, 67, 943-948.

B. Ortho $^{125}$Iodination of phenols: This procedure allows for the incorporation of $^{125}$I at the ortho position of a phenol as reported by Collier, T. L. and co-workers in J. Labelled Compd. Radiopharm., 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in J. Labelled Compd. Radiopharm. 2001, 44, S280-S282.

Provided is a compound selected from compounds of Formula (I) and pharmaceutically acceptable salts, solvates, and hydrates thereof:

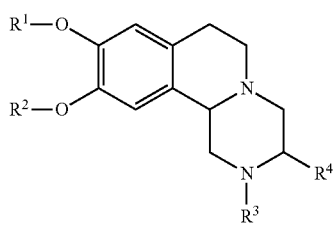

(I)

wherein:

$R^1$ and $R^2$ are independently lower alkyl, lower cycloalkyl, or lower cycloalkylalkyl, wherein each lower alkyl, lower cycloalkyl, and lower cycloalkylalkyl is independently unsubstituted or substituted with one or more halo, cyano, or lower alkoxy;

$R^3$ is lower alkyl; and $R^4$ is lower alkyl or lower cycloalkylalkyl.

In some embodiments, $R^1$ is lower alkyl. In some embodiments, $R^1$ is $C_{1-6}$ saturated alkyl. In some embodiments, $R^1$ is unsubstituted lower alkyl. In some embodiments, $R^1$ is methyl, ethyl, n-propyl, iso-propyl, iso-butyl, neo-pentyl.

In some embodiments, $R^1$ is substituted lower alkyl.

In some embodiments, $R^1$ is lower alkyl substituted with halo. In some embodiments, $R^1$ is $C_{1-4}$ saturated alkyl substituted with one, two, or three halo groups. In some embodiments, each of the one, two, or three halo groups is fluoro.

In some embodiments, $R^1$ is fluoroalkyl. In some embodiments, $R^1$ is —$(CH_2)_3CH_2F$, —$(CH_2)_2CH_2F$, —$CH_2CH_2F$, —$(CH_2)_4CF_3$, —$(CH_2)_3CF_3$, —$(CH_2)_2CF_3$, or —$CH_2CF_3$.

In some embodiments, $R^1$ is lower alkyl substituted with lower alkoxy. In some embodiments, $R^1$ is $C_{1-4}$ saturated alkyl substituted with $C_{1-4}$ saturated alkoxy. In some embodiments, $R^1$ is —$CH_2CH_2OCH_3$.

In some embodiments, $R^1$ is lower alkyl substituted with cyano. In some embodiments, $R^1$ is $C_{1-4}$ saturated alkyl substituted with a cyano group. In some embodiments, $R^1$ is —$CH_2CH_2CH_2CN$.

In some embodiments, $R^1$ is cycloalkyl. In some embodiments, $R^1$ is cyclopropyl or cyclobutyl.

In some embodiments, $R^1$ is cycloalkylalkyl. In some embodiments, $R^1$ is lower cycloalkylalkyl wherein the lower alkyl portion of the lower cycloalkylalkyl is $C_{1-4}$ saturated alkyl and the cycloalkyl portion of the lower cycloalkylalkyl is cyclopropyl, cyclobutyl, or cyclopentyl. In some embodiments, $R^1$ is —$CH_2$-cyclopropyl, —$CH_2$-cyclobutyl, or —$CH_2$-cyclopentyl.

In some embodiments, $R^1$ is substituted cycloalkylalkyl.

In some embodiments, $R^1$ is cycloalkylalkyl substituted with halo. In some embodiments, $R^1$ is lower cycloalkylalkyl substituted with halo wherein the lower alkyl portion of the lower cycloalkylalkyl is $C_{1-4}$ saturated alkyl and the cycloalkyl portion of the lower cycloalkylalkyl is cyclopropyl, cyclobutyl, or cyclopentyl and wherein either portion of the lower cycloalkylalkyl group is substituted with halo. In some embodiments, $R^1$ is:

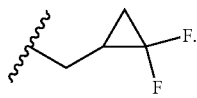 [SMILES: *CC1CC1(F)F]

In some embodiments, $R^2$ is lower alkyl. In some embodiments, $R^2$ is $C_{1-4}$ saturated alkyl. In some embodiments, $R^2$ is methyl, ethyl or propyl. In some embodiments, $R^2$ is methyl.

In some embodiments, $R^3$ is $C_{1-6}$ saturated alkyl. In some embodiments, $R^3$ is methyl, ethyl, n-propyl, iso-propyl, iso-butyl, or neo-pentyl. In some embodiments, $R^3$ is methyl.

In some embodiments, $R^4$ is lower alkyl. In some embodiments, $R^4$ is $C_{1-6}$ saturated alkyl. In some embodiments, $R^4$ is iso-butyl or neo-pentyl.

In some embodiments, $R^4$ is lower cycloalkyl or lower cycloalkylalkyl. In some embodiments, $R^4$ is cyclopropyl, cyclobutyl, or —$CH_2$-cyclobutyl. In some embodiments, $R^4$ is lower cycloalkylalkyl wherein the lower alkyl portion of the lower cycloalkylalkyl is $C_{1-4}$ saturated alkyl and the cycloalkyl portion of the lower cycloalkylalkyl is cyclopropyl or cyclobutyl.

In some embodiments, the VMAT2 inhibitor is selected from compounds of Formula (II) and pharmaceutically acceptable salts, solvates, and hydrates thereof:

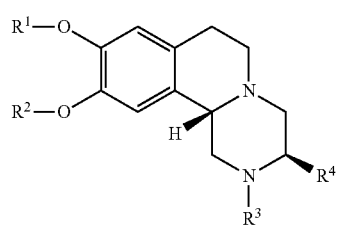

(II)

wherein $R^1$, $R^2$, $R^3$, and $R^4$ are as described herein.

In some embodiments, the VMAT2 inhibitor is selected from compounds of Formula (III) and pharmaceutically acceptable salts, solvates, and hydrates thereof:

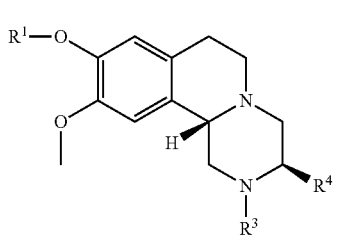

(III)

wherein $R^1$, $R^3$, and $R^4$ are as described herein.

In some embodiments, the VMAT2 inhibitor is selected from compounds of Formula (IV) and pharmaceutically acceptable salts, solvates, and hydrates thereof:

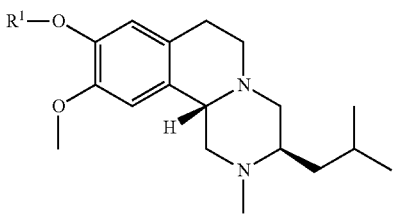

(IV)

wherein R¹ is as described herein.

In some embodiments, the VMAT2 inhibitor is selected from compounds of Formula (V) and pharmaceutically acceptable salts, solvates, and hydrates thereof:

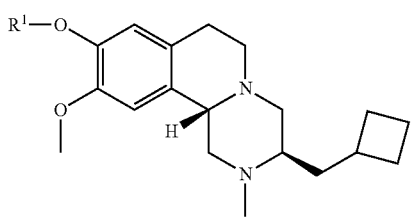

(V)

wherein R¹ is as described herein.

In some embodiments, the VMAT2 inhibitor is selected from compounds of Formula (VI) and pharmaceutically acceptable salts, solvates, and hydrates thereof:

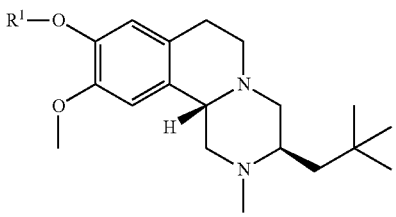

(VI)

wherein R¹ is as described herein.

In some embodiments, the VMAT2 inhibitor is deuterated at one or more positions.

In some embodiments, R¹ is deuterated at one or more positions. In some embodiments, R¹ is —$CD_3$ or —$CD_2CD_3$.

In some embodiments, R² is deuterated at one or more positions. In some embodiments, R² is —$CD_3$ or —$CD_2CD_3$.

In some embodiments, each of R¹ and R² is deuterated at one or more positions.

In some embodiments, the compound is selected from one of the following compounds and pharmaceutically acceptable salts, solvates, and hydrates thereof.

(3R,11bS)-2-ethyl-9,10-dimethoxy-3-(2-methylpropyl)-1H, 2H,3H,4H,6H,7H,11bH-piperazino[2,1-a]isoquinoline;
(3R,11bS)-9,10-dimethoxy-2-methyl-3-(2-methylpropyl)-1H,2H,3H,4H,6H,7H,11bH-piperazino[2,1-a]isoquinoline;
(3R,11bS)-9,10-dimethoxy-2,3-bis(2-methylpropyl)-1H, 2H,3H,4H,6H,7H,11bH-piperazino[2,1-a]isoquinoline;
(3R,11bR)-2-ethyl-9,10-dimethoxy-3-(2-methylpropyl)-1H, 2H,3H,4H,6H,7H,11bH-piperazino[2,1-a]isoquinoline;
(3R,11bR)-9,10-dimethoxy-2-methyl-3-(2-methylpropyl)-1H,2H,3H,4H,6H,7H,11bH-piperazino[2,1-a]isoquinoline;
(3R,11bR)-9,10-dimethoxy-2,3-bis(2-methylpropyl)-1H, 2H,3H,4H,6H,7H,11bH-piperazino[2,1-a]isoquinoline;
(3R,11bS)-9-ethoxy-10-methoxy-2-methyl-3-(2-methylpropyl)-1H,2H,3H,4H,6H,7H,11bH-piperazino[2,1-a]isoquinoline;
(3R,11bS)-10-methoxy-2-methyl-3-(2-methylpropyl)-9-(propan-2-yloxy)-1H,2H,3H,4H,6H,7H, 11bH-piperazino[2,1-a]isoquinoline;
(3R,1 b S)-9-(3-fluoropropoxy)-10-methoxy-2-methyl-3-(2-methylpropyl)-1H,2H,3H,4H,6H,7H, 11bH-piperazino[2, 1-a]isoquinoline;
(3R,11bS)-9-(2-fluoroethoxy)-10-methoxy-2-methyl-3-(2-methylpropyl)-1H,2H,3H,4H,6H,7H,11bH-piperazino[2, 1-a]isoquinoline;
(3R,11bS)-9-cyclopropoxy-10-methoxy-2-methyl-3-(2-methylpropyl)-1H,2H,3H,4H,6H,7H,11bH-piperazino[2, 1-a]isoquinoline;
(3R,11bS)-10-methoxy-2-methyl-3-(2-methylpropyl)-9-propoxy-1H,2H,3H,4H,6H,7H,11bH-piperazino[2,1-a]isoquinoline;
(3R,1 b S)-9-(cyclopentyloxy)-10-methoxy-2-methyl-3-(2-methylpropyl)-1H,2H,3H,4H,6H,7H, 11bH-piperazino[2, 1-a]isoquinoline;
(3R,11bS)-10-methoxy-2-methyl-3-(2-methylpropyl)-9-(prop-2-en-1-yloxy)-1H,2H,3H,4H,6H,7H, 11bH-piperazino[2,1-a]isoquinoline;
(3R,1bS)-10-methoxy-2-methyl-9-(2-methylpropoxy)-3-(2-methylpropyl)-1H,2H,3H,4H,6H,7H,11bH-piperazino[2, 1-a]isoquinoline;
(3R,11bS)-10-methoxy-9-(2-methoxyethoxy)-2-methyl-3-(2-methylpropyl)-1H,2H,3H,4H,6H,7H, 11bH-piperazino[2,1-a]isoquinoline;
(3R,11bS)-9-(cyclobutylmethoxy)-10-methoxy-2-methyl-3-(2-methylpropyl)-1H,2H,3H,4H,6H,7H, 11bH-piperazino[2,1-a]isoquinoline;
4-{[(3R,11bS)-10-methoxy-2-methyl-3-(2-methylpropyl)-1H,2H,3H,4H,6H,7H, 11bH-piperazino[2,1-a]isoquinolin-9-yl]oxy}butanenitrile;
(3R,11bS)-10-methoxy-2-methyl-3-(2-methylpropyl)-9-(4, 4,4-trifluorobutoxy)-1H,2H,3H,4H,6H,7H, 11bH-piperazino[2,1-a]isoquinoline;
(3R,1 b S)-9-(4-fluorobutoxy)-10-methoxy-2-methyl-3-(2-methylpropyl)-1H,2H,3H,4H,6H,7H, 11bH-piperazino[2, 1-a]isoquinoline;
(3R,11bS)-9-(cyclopropylmethoxy)-10-methoxy-2-methyl-3-(2-methylpropyl)-1H,2H,3H,4H,6H,7H, 11bH-piperazino[2,1-a]isoquinoline;
(3R,11bS)-9-cyclobutoxy-10-methoxy-2-methyl-3-(2-methylpropyl)-1H,2H,3H,4H,6H,7H,11bH-piperazino[2,1-a]isoquinoline;
(3R,11bS)-10-methoxy-2-methyl-3-(2-methylpropyl)-9-(2, 2,2-trifluoroethoxy)-1H,2H,3H,4H,6H,7H, 11bH-piperazino[2,1-a]isoquinoline;
(3R,1 b S)-9-[(2,2-difluorocyclopropyl)methoxy]-10-methoxy-2-methyl-3-(2-methylpropyl)-1H,2H,3H,4H, 6H,7H,11bH-piperazino[2,1-a]isoquinoline;
(3R,11bS)-10-methoxy-2-methyl-3-(2-methylpropyl)-9-(3, 3,3-trifluoropropoxy)-1H,2H,3H,4H, 6H,7H,11bH-piperazino[2,1-a]isoquinoline;
(3R,11 bR)-10-methoxy-2-methyl-3-(2-methylpropyl)-9-(propan-2-yloxy)-1H,2H,3H,4H,6H,7H, 11bH-piperazino[2,1-a]isoquinoline;

(3R,11bR)-9-(3-fluoropropoxy)-10-methoxy-2-methyl-3-(2-methylpropyl)-1H,2H,3H,4H,6H,7H, 11bH-piperazino[2,1-a]isoquinoline;

(3R,11bR)-9-(2-fluoroethoxy)-10-methoxy-2-methyl-3-(2-methylpropyl)-1H,2H,3H,4H,6H,7H,11bH-piperazino[2,1-a]isoquinoline;

(3R,11bR)-9-cyclopropoxy-10-methoxy-2-methyl-3-(2-methylpropyl)-1H,2H,3H,4H,6H,7H,11bH-piperazino[2,1-a]isoquinoline;

(3R,11bS)-3-(cyclobutylmethyl)-9-(3-fluoropropoxy)-10-methoxy-2-methyl-1H,2H,3H,4H,6H,7H, 11bH-piperazino[2,1-a]isoquinoline;

(3R,1bS)-3-(cyclobutylmethyl)-10-methoxy-2-methyl-9-(2,2,2-trifluoroethoxy)-1H,2H,3H,4H,6H,7H, 11bH-piperazino[2,1-a]isoquinoline;

(3R,11bS)-3-(cyclobutylmethyl)-9-[(2,2-difluorocyclopropyl)methoxy]-10-methoxy-2-methyl-1H,2H,3H,4H,6H, 7H, 11bH-piperazino[2,1-a]isoquinoline;

(3R,11bS)-3-(cyclobutylmethyl)-9-(2-fluoroethoxy)-10-methoxy-2-methyl-1H,2H,3H,4H,6H,7H,11bH-piperazino[2,1-a]isoquinoline;

(3R,11bS)-3-(cyclobutylmethyl)-9-(cyclopropylmethoxy)-10-methoxy-2-methyl-1H,2H,3H,4H,6H,7H, 11bH-piperazino[2,1-a]isoquinoline;

(3R,1bS)-9-(cyclobutylmethoxy)-3-(cyclobutylmethyl)-10-methoxy-2-methyl-1H,2H, 3H,4H,6H,7H,11bH-piperazino[2,1-a]isoquinoline;

(3R,1bS)-3-(cyclobutylmethyl)-10-methoxy-2-methyl-9-(4,4,4-trifluorobutoxy)-1H,2H,3H,4H,6H,7H,11bH-piperazino[2,1-a]isoquinoline;

(3R,11bS)-3-(cyclobutylmethyl)-9-(4-fluorobutoxy)-10-methoxy-2-methyl-1H,2H, 3H,4H,6H,7H,11bH-piperazino[2,1-a]isoquinoline;

(3R,11bR)-3-(cyclobutylmethyl)-9-(3-fluoropropoxy)-10-methoxy-2-methyl-1H,2H, 3H,4H,6H,7H,11bH-piperazino[2,1-a]isoquinoline;

(3R,11bS)-3-(2,2-dimethylpropyl)-9-(3-fluoropropoxy)-10-methoxy-2-methyl-1H,2H,3H,4H,6H,7H,11bH-piperazino[2,1-a]isoquinoline;

(3R,1bS)-3-(2,2-dimethylpropyl)-9,10-dimethoxy-2-methyl-1H,2H,3H,4H,6H,7H,11bH-piperazino[2,1-a]isoquinoline;

(3R,1bS)-3-(2,2-dimethylpropyl)-10-methoxy-2-methyl-9-(2,2,2-trifluoroethoxy)-1H,2H,3H,4H,6H,7H, 1bH-piperazino[2,1-a]isoquinoline;

(3R,1bS)-9-[(2,2-difluorocyclopropyl)methoxy]-3-(2,2-dimethylpropyl)-10-methoxy-2-methyl-1H,2H,3H,4H,6H, 7H,11bH-piperazino[2,1-a]isoquinoline;

(3R,11bS)-3-(2,2-dimethylpropyl)-10-methoxy-2-methyl-9-(3,3,3-trifluoropropoxy)-1H,2H,3H,4H,6H,7H,11bH-piperazino[2,1-a]isoquinoline;

(3R,11bS)-3-(2,2-dimethylpropyl)-9-(2-fluoroethoxy)-10-methoxy-2-methyl-1H,2H, 3H,4H,6H, 7H,11bH-piperazino[2,1-a]isoquinoline;

(3R,11bS)-9-(cyclopropylmethoxy)-3-(2,2-dimethylpropyl)-10-methoxy-2-methyl-1H,2H,3H,4H,6H,7H, 1bH-piperazino[2,1-a]isoquinoline;

(3R,11bS)-9-(cyclobutylmethoxy)-3-(2,2-dimethylpropyl)-10-methoxy-2-methyl-1H,2H,3H,4H,6H,7H,11bH-piperazino[2,1-a]isoquinoline;

(3R,1bS)-3-(2,2-dimethylpropyl)-10-methoxy-2-methyl-9-(4,4,4-trifluorobutoxy)-1H,2H,3H,4H,6H,7H,11bH-piperazino[2,1-a]isoquinoline;

(3R,11bS)-3-(2,2-dimethylpropyl)-9-(4-fluorobutoxy)-10-methoxy-2-methyl-1H,2H, 3H,4H,6H, 7H,11bH-piperazino[2,1-a]isoquinoline;

(3R,11bS)-3-(2,2-dimethylpropyl)-10-methoxy-9-(2-methoxyethoxy)-2-methyl-1H,2H, 3H,4H,6H, 7H,11bH-piperazino[2,1-a]isoquinoline;

(3R,11bS)-3-(2,2-dimethylpropyl)-9-ethoxy-10-methoxy-2-methyl-1H,2H,3H,4H,6H,7H,11bH-piperazino[2,1-a]isoquinoline;

(3R,11bS)-3-(2,2-dimethylpropyl)-10-methoxy-2-methyl-9-(propan-2-yloxy)-1H,2H,3H,4H,6H,7H,11bH-piperazino[2,1-a]isoquinoline;

(3R,11bS)-3-(2,2-dimethylpropyl)-9-(ethoxy-$d_5$)-10-methoxy-2-methyl-1H,2H,3H,4H,6H,7H,11bH-piperazino[2,1-a]isoquinoline;

(3R,1bS)-3-(2,2-dimethylpropyl)-9,10-bis(methoxy-$d_3$)-2-methyl-1H,2H,3H,4H,6H,7H,11bH-piperazino[2,1-a]isoquinoline;

(3R,11bR)-3-(2,2-dimethylpropyl)-9-(3-fluoropropoxy)-10-methoxy-2-methyl-1H,2H,3H,4H,6H,7H,11bH-piperazino[2,1-a]isoquinoline; and (3R,11bR)-3-(2,2-dimethylpropyl)-9,10-dimethoxy-2-methyl-1H,2H,3H,4H,6H,7H,11bH-piperazino[2,1-a]isoquinoline.

In some embodiments, the compound is selected from 3-(2,2-dimethylpropyl)-9,10-dimethoxy-2-methyl-1H,2H,3H,4H,6H,7H,11bH-piperazino[2,1-a]isoquinoline and pharmaceutically acceptable salts, solvates, and hydrates thereof. In some embodiments, the compound has a deuterium at one or more positions.

In some embodiments, the compound is selected from (3R,11bS)-3-(2,2-dimethylpropyl)-9,10-dimethoxy-2-methyl-1H,2H, 3H,4H,6H,7H,11bH-piperazino[2,1-a]isoquinoline and pharmaceutically acceptable salts, solvates, and hydrates thereof. In some embodiments, the compound has a deuterium at one or more positions.

In some embodiments, the compound is selected from 9-cyclopropoxy-10-methoxy-2-methyl-3-(2-methylpropyl)-1H,2H,3H,4H,6H,7H,11bH-piperazino[2,1-a]isoquinoline and pharmaceutically acceptable salts, solvates, and hydrates thereof. In some embodiments, the compound has a deuterium at one or more positions.

In some embodiments, the compound is selected from (3R,11bS)-9-cyclopropoxy-10-methoxy-2-methyl-3-(2-methylpropyl)-1H,2H,3H,4H,6H,7H,11bH-piperazino[2,1-a]isoquinoline and pharmaceutically acceptable salts, solvates, and hydrates thereof. In some embodiments, the compound has a deuterium at one or more positions.

In some embodiments, the compound is selected from 3-(2,2-dimethylpropyl)-10-methoxy-2-methyl-9-(2,2,2-trifluoroethoxy)-1H,2H,3H,4H,6H,7H,11bH-piperazino[2,1-a]isoquinoline and pharmaceutically acceptable salts, solvates, and hydrates thereof. In some embodiments, the compound has a deuterium at one or more positions.

In some embodiments, the compound is selected from (3R,11bS)-3-(2,2-dimethylpropyl)-10-methoxy-2-methyl-9-(2,2,2-trifluoroethoxy)-1H,2H,3H,4H,6H,7H, 11bH-piperazino[2,1-a]isoquinoline and pharmaceutically acceptable salts, solvates, and hydrates thereof. In some embodiments, the compound has a deuterium at one or more positions.

In some embodiments, the compound is selected from 3-(2,2-dimethylpropyl)-9-ethoxy-10-methoxy-2-methyl-1H,2H, 3H,4H, 6H, 7H, 11bH-piperazino[2,1-a]isoquinoline and pharmaceutically acceptable salts, solvates, and hydrates thereof. In some embodiments, the compound has a deuterium at one or more positions.

In some embodiments, the compound is selected from (3R,11bS)-3-(2,2-dimethylpropyl)-9-ethoxy-10-methoxy-2-methyl-1H,2H, 3H,4H, 6H, 7H, 11bH-piperazino[2,1-a]isoquinoline and pharmaceutically acceptable salts, solvates, and hydrates thereof. In some embodiments, the compound has a deuterium at one or more positions.

In some embodiments, the compound is selected from 9,10-bis(methoxy-d3)-2-methyl-3-neopentyl-1,3,4,6,7,11b-hexahydro-2H-pyrazino[2,1-a]isoquinoline and pharmaceutically acceptable salts, solvates, and hydrates thereof. In some embodiments, the compound has a deuterium at one or more additional positions.

In some embodiments, the compound is selected from (3R,11bS)-9,10-bis(methoxy-d3)-2-methyl-3-neopentyl-1, 3,4,6,7,11b-hexahydro-2H-pyrazino[2,1-a]isoquinoline and pharmaceutically acceptable salts, solvates, and hydrates thereof. In some embodiments, the compound has a deuterium at one or more additional positions.

In some embodiments, the compound is selected from 10-methoxy-2-methyl-3-(2-methylpropyl)-9-(2,2,2-trifluoroethoxy)-1H,2H,3H,4H,6H,7H, 11bH-piperazino[2,1-a]isoquinoline and pharmaceutically acceptable salts, solvates, and hydrates thereof. In some embodiments, the compound has a deuterium at one or more positions.

In some embodiments, the compound is selected from (3R,11bS)-10-methoxy-2-methyl-3-(2-methylpropyl)-9-(2, 2,2-trifluoroethoxy)-1H,2H,3H,4H,6H,7H, 11bH-piperazino[2,1-a]isoquinoline and pharmaceutically acceptable salts, solvates, and hydrates thereof. In some embodiments, the compound has a deuterium at one or more positions.

In some embodiments, the compound is selected from 10-methoxy-2-methyl-3-(2-methylpropyl)-9-(3,3,3-trifluoropropoxy)-1H,2H,3H,4H,6H,7H,11bH-piperazino[2,1-a]isoquinoline and pharmaceutically acceptable salts, solvates, and hydrates thereof. In some embodiments, the compound has a deuterium at one or more positions.

In some embodiments, the compound is selected from (3R,11bS)-10-methoxy-2-methyl-3-(2-methylpropyl)-9-(3, 3,3-trifluoropropoxy)-1H,2H,3H,4H,6H,7H, 11bH-piperazino[2,1-a]isoquinoline and pharmaceutically acceptable salts, solvates, and hydrates thereof. In some embodiments, the compound has a deuterium at one or more positions.

In some embodiments, the compound is selected from 3-(2,2-dimethylpropyl)-9-(3-fluoropropoxy)-10-methoxy-2-methyl-1H,2H,3H,4H,6H,7H, 11bH-piperazino[2,1-a]isoquinoline and pharmaceutically acceptable salts, solvates, and hydrates thereof. In some embodiments, the compound has a deuterium at one or more positions.

In some embodiments, the compound is selected from (3R,11bS)-3-(2,2-dimethylpropyl)-9-(3-fluoropropoxy)-10-methoxy-2-methyl-1H,2H,3H,4H,6H,7H, 11bH-piperazino[2,1-a]isoquinoline and pharmaceutically acceptable salts, solvates, and hydrates thereof. In some embodiments, the compound has a deuterium at one or more positions.

In some embodiments, the compound is selected from 3-(2,2-dimethylpropyl)-10-methoxy-2-methyl-9-(3,3,3-trifluoropropoxy)-1H,2H,3H,4H,6H,7H, 11bH-piperazino[2,1-a]isoquinoline and pharmaceutically acceptable salts, solvates, and hydrates thereof. In some embodiments, the compound has a deuterium at one or more positions.

In some embodiments, the compound is selected from (3R,11bS)-3-(2,2-dimethylpropyl)-10-methoxy-2-methyl-9-(3,3,3-trifluoropropoxy)-1H,2H,3H,4H,6H,7H, 11bH-piperazino[2,1-a]isoquinoline and pharmaceutically acceptable salts, solvates, and hydrates thereof. In some embodiments, the compound has a deuterium at one or more positions.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of VMAT2 inhibitors of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of VMAT2 inhibitors of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R.V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J.C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," *Verlag Helvetica Chimica Acta*, Zurich, 2002.

The VMAT2 inhibitors described herein may be prepared by known organic synthesis techniques, including the methods described in the Schemes hereafter and in more detail in the Examples.

Reaction Scheme 1

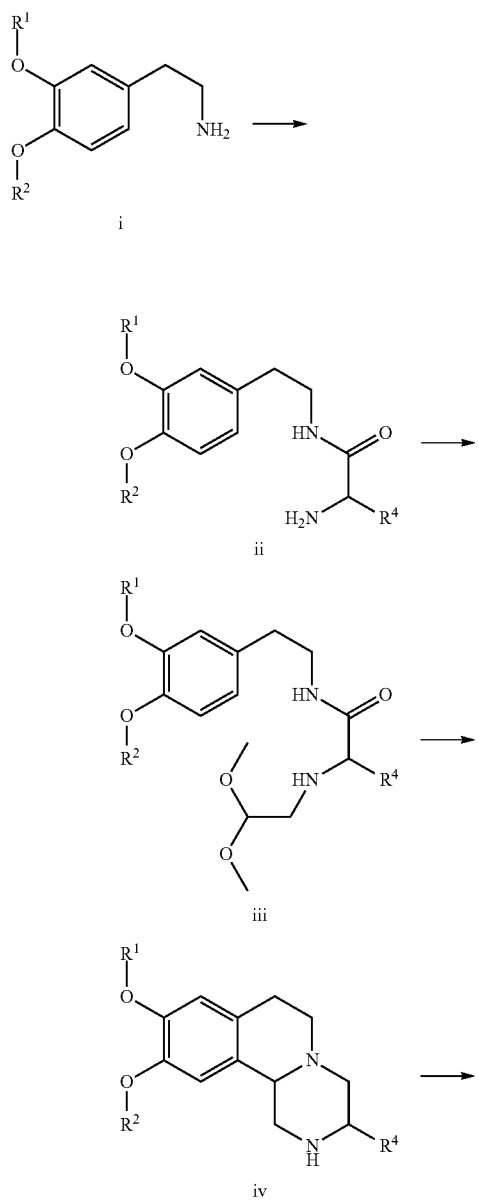

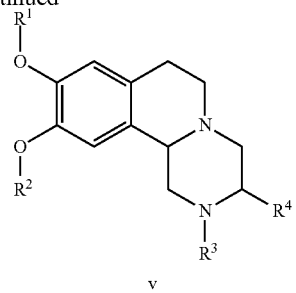

Amine i is coupled with a protected amino acid, followed by a deprotection to yield ii. Structure iii is formed by reductive deamination with a dimethoxy acetal. Structure iii is cyclized under acidic conditions followed by reduction of the amide carbonyl giving iv. Alkylation gives v.

Also provided is a method of preparing a compound of Formula v comprising alkylating a compound of Formula iv to yield a compound of Formula v.

In some embodiments, alkylating a compound of Formula iv comprises reacting a compound of Formula iv with a compound of formula $R^3$—X wherein X is a leaving group such as iodo. In some embodiments, the alkylating is performed in the presence of a base, such as potassium carbonate. In some embodiments, the alkylating is performed in a polar, aprotic solvent, such as DMF, THF, 1,4-dioxane, acetonitrile, DMSO, or mixtures thereof. In some embodiments, the polar, aprotic solvent is DMF. In some embodiments, at least one equivalent of the compound of formula $R^3$—X is used. In some embodiments, an excess of a compound of formula $R^3$—X is used.

In some embodiments, alklylating a compound of Formula iv comprises reacting a compound of Formula iv with di-tert-butyl dicarbonate in the presence of a base to yield the corresponding carboxylate which is then reduced with a reducing agent, e.g., with lithium aluminum hydride (LAH), to yield the compound of Formula v. In some embodiments, the base is an organic base, such as trimethylamine. In some embodiments, the alkylating is performed in a polar, aprotic solvent such as methylene chloride or tetrahydrofuran. In some embodiments, at least one equivalent of the di-tert-butyl dicarbonate is used. In some embodiments, an excess of the di-tert-butyl dicarbonate is used. In some embodiments, the reduction is performed in a polar, aprotic solvent such as tetrahydrofuran or ether. In some embodiments, an excess of the reducing agent is used.

Reaction Scheme 2

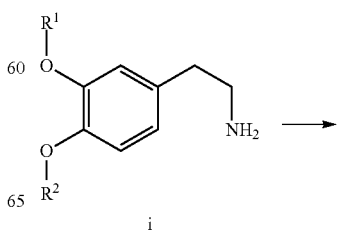

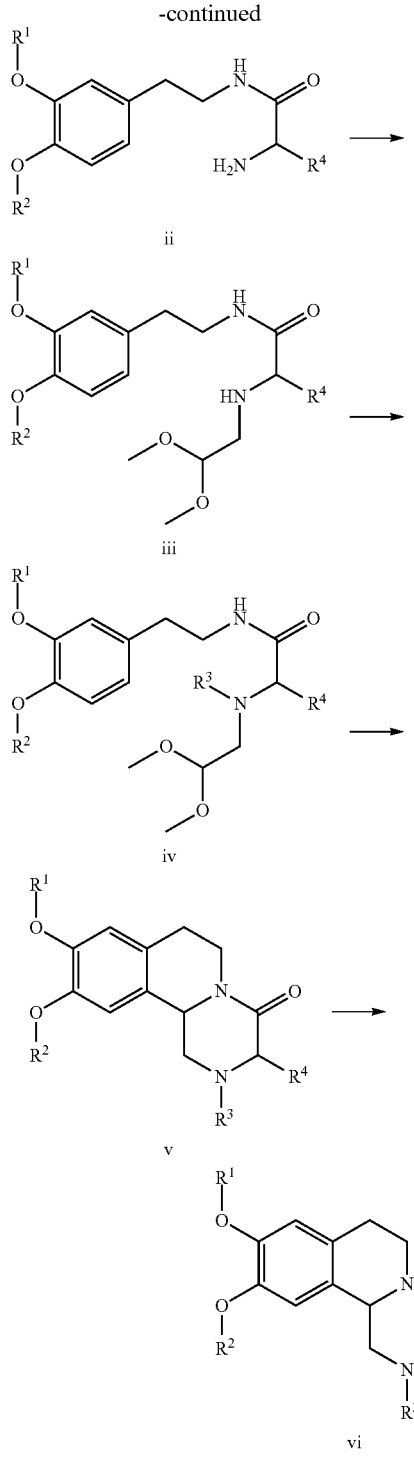

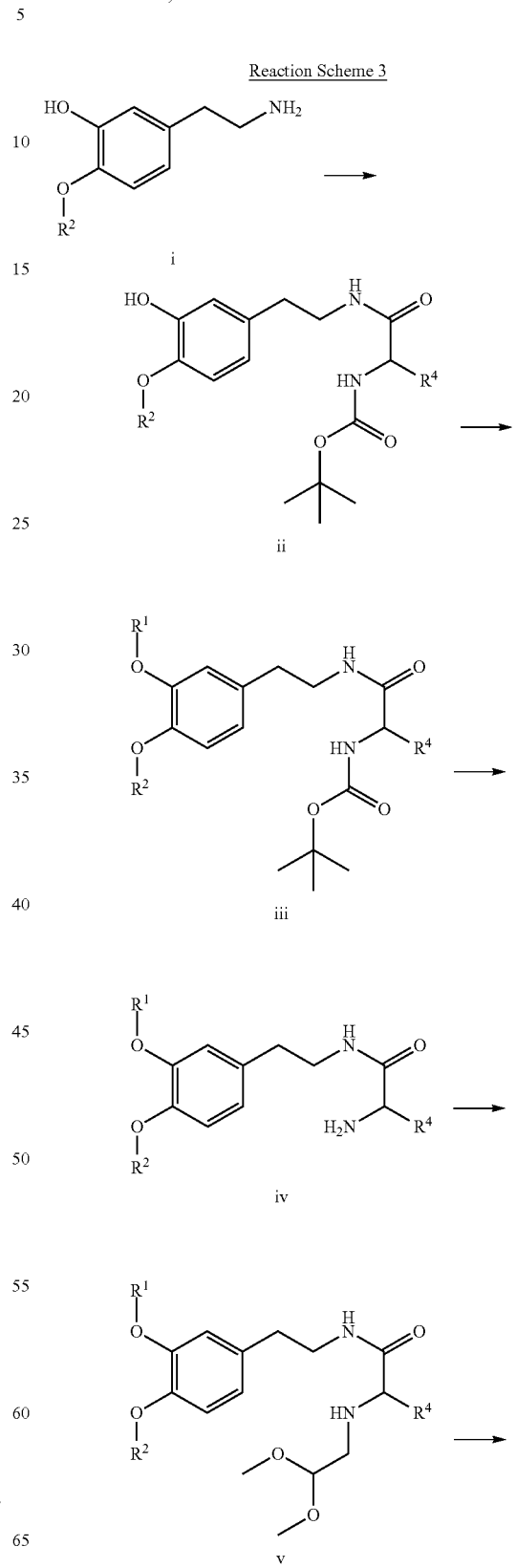

LAH or a diisobutylaluminum hydride reagent. In some embodiments, an excess of the reducing agent is used. In some embodiments, a polar, aprotic solvent is used. In some embodiments, the solvent is THF.

Amine i is coupled with a protected amino acid, followed by a deprotection to yield ii. Structure iii is formed by reductive deamination with a dimethoxy acetal. Structure iv is formed by reductive deamination with a paraformaldehyde. Structure iv is cyclized under acidic conditions giving v. Reduction of the amide carbonyl gives vi.

Also provided is a method of preparing a compound of Formula vi comprising reducing a compound of Formula v to yield a compound of Formula vi. In some embodiments, the reducing is performed using a reducing agent such as

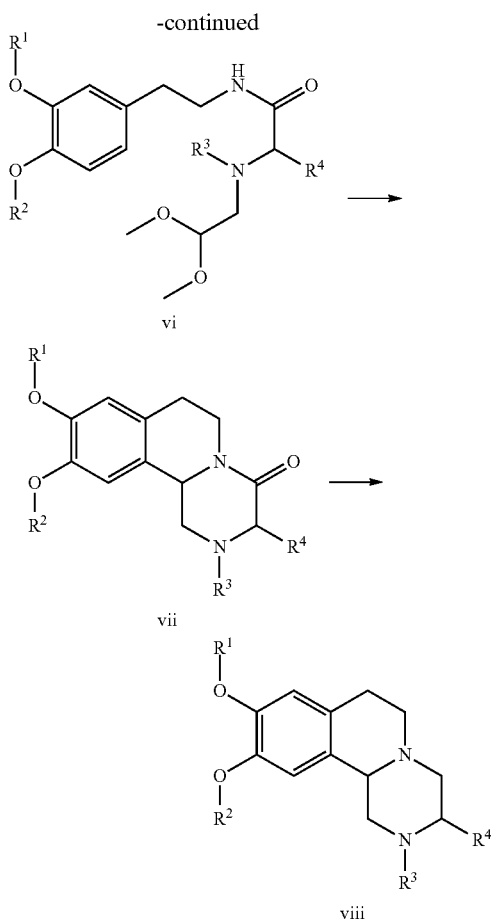

Amine i is coupled with a protected amino acid to yield ii. Alcohol ii is alkylated with R¹ to yield iii. Deprotection of iii yields structure iv. Structure v is formed by reductive deamination with a dimethoxy acetal. Structure vi is formed by reductive deamination with a paraformaldehyde. Structure vi is cyclized under acidic conditions giving vii. Reduction of the amide carbonyl gives viii.

Also provided is a method of preparing a compound of Formula viii comprising reducing a compound of Formula vii to yield a compound of Formula vi. In some embodiments, the reducing is performed using a reducing agent such as a dialkylborane, e.g., 9-borabicyclo[3.3.1]none (9-BBN) or a aminoborohydrides, e.g., lithium dimethylaminoborohydride. In some embodiments, an excess of the reducing agent is used. In some embodiments, a polar, aprotic solvent is used. In some embodiments, the solvent is THF or methyltetrahydrofuran.

Also provided is a VMAT2 inhibitor prepared by any of the methods described herein. Generally, those methods comprise the steps of cyclizing to form the tricyclic ring structure, reducing the carbonyl functionality, if present, and alkylating the nitrogen to introduce $R^3$, as shown in Reaction Scheme 1 below. In Reaction Schemes 2 and 3, $R^3$ is introduced, followed by cyclization and then reduction of the ring carbonyl. In some embodiments, the methods also comprise the step of resolving a diastereomeric mixture to yield a mixture which is enriched in the desired isomer. In some embodiments, the methods also optionally further comprise formation of a salt.

In some embodiments, the methods are safe, efficient, cost effective, and/or scalable. In some embodiments, the methods are suitable for the large scale or commercial product of the VMAT2 inhibitor.

In some embodiments, the VMAT2 inhibitors prepared by the methods provided herein have a purity of no less than about 95% by weight, no less than about 96% by weight, no less than about 97% by weight, no less than about 98% by weight, no less than about 98.5% by weight, no less than about 99% by weight, no less than about 99.5% by weight, no less than about 99.6% by weight, no less than about 99.7% by weight, no less than about 99.8% by weight, or no less than about 99.9% by weight.

In some embodiments, the overall yield of the methods provided herein is no less than about 30%, no less than about 40%, no less than about 50%, no less than about 55%, no less than about 60%, no less than about 65%, no less than about 70%, no less than about 75%, no less than about 80%, no less than about 85%, no less than about 90%, or no less than about 95%, wherein the yield is calculated based on starting material.

In certain embodiments, the weight loss on drying (LOD) of the VMAT2 inhibitors prepared by the methods provided herein is no greater than about 5% by weight, no greater than about 4% by weight, no greater than about 3% by weight, no greater than about 2% by weight, no greater than about 1% by weight, no greater than about 0.9% by weight, no greater than about 0.8% by weight, no greater than about 0.7% by weight, no greater than about 0.6% by weight, no greater than about 0.5% by weight, no greater than about 0.4% by weight, no greater than about 0.3% by weight, no greater than about 0.2% by weight, or no greater than about 0.1% by weight.

In certain embodiments, the total impurities in the VMAT2 inhibitors prepared by the methods provided herein are no greater than about 5% by weight, no greater than about 4% by weight, no greater than about 3% by weight, no greater than about 2.5% by weight, no greater than about 2% by weight, no greater than about 1.5% by weight, no greater than about 1% by weight, no greater than about 0.5% by weight, or no greater than about 0.1% by weight.

In certain embodiments, the VMAT2 inhibitor is enantiomerically enriched so that one enantiomer is present in an amount greater than 50%. In certain embodiments, the VMAT2 inhibitor is substantially free from other stereoisomers. As used herein, the phrase "substantially free from other stereoisomers" means that the composition contains ≤15%, such as ≤10%, e.g., ≤5%, or ≤1% of another stereoisomer(s). In certain embodiments, the impurity is detectable by HPLC (high performance liquid chromatography).

In certain embodiments, the impurity is a volatile organic compound. In certain embodiments, the impurity is an organic solvent. In certain embodiments, the impurity is DMF, tetrahydrofuran, or methylene chloride.

In certain embodiments, the impurity is a metal based impurity.

In certain embodiments, the impurity includes, but is not limited to, a compound of formula $R^3$—X wherein X is a leaving group such as iodo, a compound of formula i, ii, iii, and or iv of Reaction Scheme 1, a compound of formula i, ii, iii, iv, or v of Reaction Scheme 2, or a compound of formula i, ii, iii, iv, v, vi, or vii of Reaction Scheme 3.

Also provided is a process for preparing a composition comprising admixing a VMAT2 inhibitor as described herein and one or more pharmaceutically acceptable excipients and/or diluents.

The VMAT2 inhibitor described herein may reduce the supply of monoamines in the central nervous system by inhibiting the human monoamine transporter isoform 2 (VMAT2). As such, these VMAT2 inhibitor may have utility over a wide range of therapeutic applications, and may be used to treat a variety of disorders which are caused by or linked to inhibition of the human monoamine transporter isoform 2. These disorders include neurological and psychiatric disorders, especially hyperkinetic movement disorders, schizophrenia, and mood disorders.

Hyperkinetic movement disorders represent a category of neurological disorders that are characterized by unwanted and uncontrollable, or poorly controllable, involuntary movements. The phenomenology of these disorders is quite variable encompassing chorea, tremor, dystonia, myoclonus, tics, other dyskinesias, jerks and shakes. Hyperkinetic movement disorders include ataxia, chorea, dystonia, hemifacial spasm, Huntington's disease, chorea associated with Huntington's disease, myoclonus, restless leg syndrome, tardive dyskinesia, tics, Tourette's syndrome, and tremors.

Mood disorders represent a category of mental disorders in which the underlying problem primarily affects a person's persistent emotional state (their mood). Mood disorders include: major depressive disorder (also called major depression), bipolar disorder, persistent depressive disorder (long lasting low grade depression), cyclothymia (a mild form of bipolar disorder), catatonic depression, post-partum depression, mania, and seasonal affective disorder (SAD). Mood disorders include substance-induced mood disorders and mood disorders due to a medical condition, e.g., hypothyroidism or Parkinson's disease.

Bipolar disorder, also known as bipolar affective disorder or manic-depressive illness, is a mental disorder characterized by periods of elevated mood and periods of depression. The periods of elevated mood is known as mania or hypomania depending on the severity or whether psychosis is present. Symptoms of mania or a manic episode include a long period of feeling "high" or an overly happy or outgoing mood, extreme irritability, talking very fast, racing thoughts, jumping from one idea to another, being easily distracted, increasing activities, being overly restless, sleeping little, having an unrealistic belief in one's abilities, impulsive behavior, and engaging in pleasurable, high-risk behaviors. Symptoms of depression or a depressive episode include: an overly long period of sadness or hopelessness, loss of interest in activities, feeling tired, problems with concentration or memory, difficulty making decisions, being restless or irritable, change in eating or sleeping habits, and suicide ideation. Patients with bipolar disorder have a high risk of suicide and self-harm. The cause of bipolar disorder is not completely understood, but both genetic and environmental factors are thought to play a role. Environmental factors include long term stress and a history of child abuse.

Medications for treatment of the manic, psychotic, or depressive aspects of bipolar disorder generally include mood stabilizers, atypical antipsychotics, or antidepressants, in combination with psychotherapy. Sleep medications may also be used to help with sleep disturbances. For severe cases in which medication and psychotherapy does not work, electroconvulsive therapy may be used. Bipolar disorder usually is a lifelong illness and can worsen if left untreated. Long-term, continuous treatment is needed to control symptoms, and even with proper treatment mood changes can still occur. Patients frequently need to try several different medications before finding ones that help control symptoms. Given the unpleasant and potentially severe side effects associated with these medications, particularly anti-psychotic medications, a need exists to develop new therapeutics for treating mania in mood disorders and their related symptoms.

Schizophrenia affects approximately 1% of the adult population and reduces life expectancy by an average of 20 to 25 years through the impact of the disorder on self-care and physical health, as well as through suicide. At the present time the etiological mechanisms underlying schizophrenia are poorly understood. Schizophrenia is diagnosed clinically, based on characteristic symptoms of psychosis, disorganization and so called 'negative' symptoms (representing a reduced range of emotional expression, reduced production of speech and a lack of volition/motivation); duration of illness; impaired functioning; and the exclusion of other disorders such as autism and bipolar disorder. For clinicians, identifying which psychotic patients have schizophrenia requires clinical acumen and familiarity with the DSM-IV or ICD-10 diagnostic manuals [see, e.g., Corvin, *BMC Biol.* 2011; 9: 77].

Schizoaffective disorder is a mental health condition characterized primarily by symptoms of schizophrenia, such as hallucinations or delusions, and symptoms of a mood disorder, such as mania and depression. Diagnosis may be difficult as symptoms of schizophrenia and mood disorders are both present and many people are incorrectly diagnosed with schizophrenia or mood disorder. Treatment for schizoaffective disorder includes medications, typically antipsychotics and antidepressants and psychotherapy.

Antipsychotic drug therapy is a pillar in the treatment of schizophrenia. These antipsychotic drugs, also known as neuroleptics, generally cause a reduction of the 'positive' symptoms of schizophrenia, namely psychosis, thought disorders, and disorganized behavior. Antipsychotics generally have a lesser influence on cognition and on the 'negative' symptoms of the disease, which include lack of motivation and emotion, social withdrawal, lack of interest in everyday activities, and the reduced ability to plan or carry out activities.

Obsessive-compulsive disorder (OCD) is an anxiety disorder characterized by recurrent and persistent anxiety-provoking thoughts (obsessions) that lead to repetitive behaviors (compulsions) that focus on alleviating distress caused by obsessive thoughts. Patients may or may not recognize that the obsessions and compulsions are unreasonable, and these thoughts and behaviors can become time-consuming and impair function.

OCD is generally treated with psychotherapy, medication or both. Cognitive behavior therapy (CBT), which teaches a person different ways of thinking, behaving, and reacting to situations that help him or her to feel less anxious or fearful without having obsessive thoughts or acting compulsively (cognitive restructuring and exposure response prevention). However, CBT takes effort and practice to learn healthy ways to cope with anxiety. Medications may also be prescribed to treat OCD. The most commonly prescribed medications are anti-anxiety medications and anti-depressants. Anti-anxiety medications begin working right away, but should not be taken for long periods of time. Anti-depressants may take 10 to 12 weeks to start working and can cause side effects such as headache, nausea, sleep disturbance, and reduced libido. Atypical anti-psychotics may also be prescribed. It is not unusual for OCD patients to have to try several medications before finding one that controls OCD symptoms.

However, even when OCD is appropriately diagnosed and treated, many OCD patients are "treatment-resistant" or "treatment-refractory" and do not adequately respond to standard therapies. An estimated 10% to 40% of OCD patients are treatment-refractory (Bystritsky, Mol. Psychiatry 11:805-814). Treatment resistance generally refers to a lack of sufficient improvement despite multiple adequate and appropriate treatment trials. For mood disorders, it may be defined by failure to remit or respond clinically (50% reduction in symptoms) despite ≥2 adequate antidepressant trials or failure to respond clinically despite adequate medication trials across several neurotransmitter classes. Pallanti and Quercioli (Neuropsychopharmacol. Biol. Psychiatry 30:400-412) proposed categorizing obsessive-compulsive disorder treatment response into several stages along a spectrum, ranging from complete recovery (or remission) to full or partial response to non-response (or completely refractory). Whichever definition is used, patients with treatment resistance in anxiety disorders experience minimal restoration of function despite several appropriate treatment exposures. Factors that contribute to treatment resistance in OCD include, but are not limited to, disease severity, medical comorbidity, psychiatric comorbidity, treatment non-compliance, cultural factors, childhood stressors, long-term persistent stressors, life stage, and limitations of clinician/health system (Khalsa et al., Curr. Psychiatry, 2011, 10:45-52). Invasive therapies, including some that are irreversible, such as electroconvulsive therapy, vagal nerve stimulation, repetitive transcranial magnetic stimulation, and surgical methods, are reserved for patients with the strongest treatment resistance. More effective treatments are therefore needed to treat the symptoms associated with treatment refractory OCD.

Lesch-Nyhan syndrome is characterized by neurologic dysfunction, cognitive and behavioral disturbances, and uric acid overproduction and has a prevalence of 1:380,000. Patients with this syndrome suffer from cognitive deficits, movement disorders, and self-injurious behavior. The most common presenting feature of Lesch-Nyhan syndrome is developmental delay during the first year of life; hypotonia and delayed motor skills are usually evident by age 3-6 months. Children with Lesch-Nyhan syndrome typically fail to sit, crawl, and walk, and are ultimately confined to a wheelchair. Even with effective management of symptoms, most affected individuals survive only into their second or third decade.

Lesch-Nyhan syndrome is inherited in an X-linked recessive pattern and is caused by deficiency of the enzyme hypoxanthine-guanine phosphoribosyltransferase (HPRT) that catalyzes the conversion of hypoxanthine to inosine monophosphate (inosinic acid, IMP) and guanine to guanine monophosphate (guanylic acid, GMP) in the presence of phosphoribosyl pyrophosphate. To treat hyperuricemia and thereby reduce the risk for nephrolithiasis, urate nephropathy, gouty arthritis, and tophi, overproduction of uric acid is controlled with allopurinol, which blocks the metabolism of hypoxanthine and xanthine into uric acid catalyzed by xanthine oxidase.

No uniformly effective intervention for managing the neurobehavioral aspects of the disease exists. Self-injurious and other deleterious behaviors are typically managed by a combination of physical, behavioral, and medical treatments. Virtually all affected individuals require physical restraints to prevent self-injury. These individuals are restrained more than 75% of the time, often at their own request. No medication has been consistently effective in controlling the motor features of the disease. More effective treatments are therefore needed to manage the conditions associated with Lesch-Nyhan syndrome.

Agitation in Alzheimer's disease refers to a cluster of several behavioral symptoms associated with the disease. Agitation develops as the disease progresses and occurs in addition to cognitive loss. The cluster of symptoms includes anxiety, depression, irritability, and motor restlessness (such as pacing, wandering, constant movement). Other symptoms that may occur include sleep disturbances, delusions, hallucinations, compulsive behaviors, aggression, and general emotional distress. Agitation may occur in as many as half of all individuals with Alzheimer's disease. Agitation is associated with patients who have a poor quality of life, deteriorating family relationships and professional caregivers, ultimately leading to admission to a residential care facility.

Patients with Alzheimer's disease and who exhibit agitation have been treated with atypical antipsychotics (e.g., risperidone, olanzapine) and typical antipsychotics (e.g., haloperidol) with only modest success and with risk of serious side effects. Accordingly, a need exists to identify and develop more effective therapeutic agents for treating agitation in patients with Alzheimer's.

Fragile X syndrome (also called Martin-Bell syndrome) is a genetic condition that causes a range of developmental problems including learning disabilities and cognitive impairment. Usually, males are more severely affected by this disorder than females. Fragile X syndrome is inherited in an X-linked dominant pattern. Fragile X syndrome occurs in approximately 1 in 4,000 males and 1 in 8,000 females. This syndrome is caused by loss of the fragile X mental retardation protein (FMRP), generally due to transcriptional silencing from a CGG repeat expansion in the 5' untranslated region of the FMR1 gene (see, e.g., Verkerk et al., *Cell* 65:905-14 (1991)).

Affected individuals usually have delayed development of speech and language by the age of 2 years. Most males with Fragile X syndrome have mild to moderate intellectual disability, while about one-third of affected females are intellectually disabled. Children with Fragile X syndrome may also exhibit behavioral problems, including anxiety, attentional deficits, anxiety, and hyperactive behaviors, such as fidgeting or impulsive actions. Children with Fragile X syndrome and who have attentional deficits may be diagnosed with attention deficit disorder (ADD), which includes an impaired ability to maintain attention and difficulty focusing on specific tasks. About one-third of individuals with Fragile X syndrome have features of autism spectrum disorders that affect communication and social interaction, for example, anxiety and repetitive, stereotyped behaviors (i.e., stereotypies). Seizures occur in about 15 percent of males and about 5 percent of females with this syndrome.

The CGG repeat expansion in patients with Fragile X syndrome occurs more than 200 times. When the repeat expansion occurs to a lesser degree (i.e., between about 50-200 times), an FMR1 gene permutation occurs and FMRP is produced to some degree. FMR1 gene permutation may result in another genetic condition called Fragile X-associated tremor-ataxia syndrome (FXTAS). FXTAS is characterized by movement difficulties and cognition problems. FXTAS is a late-onset disorder, usually occurring after age 50; symptoms worsen with age. This condition also affects males more frequently and severely than females with about 1 in 3000 men affected.

Characteristics of FXTAS include problems with coordination and balance (ataxia) and intention tremor, which is trembling or shaking of a limb when the affected individual is trying to perform a voluntary movement, such as reaching for an object. Most often, intention tremors develop first, followed a few years later by ataxia. Not all persons with FXTAS have both features. Many affected individuals develop other movement problems, such as parkinsonism, which includes tremors when not moving (resting tremor), rigidity, and unusually slow movement (bradykinesia). In addition, affected individuals may have reduced sensation, numbness or tingling, pain, or muscle weakness in the lower limbs. Some people with FXTAS experience problems with the autonomic nervous system, leading to the inability to control the bladder or bowel.

Women who have a pre-mutation in their FMR1 gene are at higher risk for primary ovarian insufficiency (Fragile X-Associated Primary Ovarian Insufficiency) and are at higher risk for having children who have Fragile X syndrome. Fragile X-Associated Primary Ovarian Insufficiency is a cause of infertility and early menopause.

No uniformly effective intervention for managing the neurobehavioral aspects of Fragile X syndrome or FXTAS exists. More effective treatments are therefore needed to manage the conditions associated with these genetic diseases.

Autism spectrum disorder (ASD) is a range of complex neurodevelopment disorders, characterized by social impairments; communication difficulties; and restricted, repetitive, and stereotyped patterns of behavior (stereotypies). Autistic disorder, sometimes called autism or classical ASD, is the most severe form of ASD. Other conditions include a milder form known as Asperger syndrome, childhood disintegrative disorder, pervasive developmental disorder, which is not otherwise specified (usually referred to as PDD-NOS). Although ASD varies significantly in character and severity, it occurs in all ethnic and socioeconomic groups and affects every age group. Based on current data, experts estimate that about one of 70 children who are age eight will have an ASD. Males are four-five times more likely to have an ASD than females.

The hallmark feature of ASD is impaired social interaction. Many children with an ASD engage in repetitive movements, such as rocking and twirling, or exhibit self-abusive behavior, such as biting or head-banging.

No cures for ASDs are available. Therapies and behavioral interventions are designed to remedy specific symptoms and can bring about significant improvement. Doctors may prescribe medications for treatment of specific autism-related symptoms, such as anxiety, depression, or obsessive-compulsive disorder. Antipsychotic medications are used to treat severe behavioral problems, and seizures can be treated with one or more anticonvulsant drugs. Medication used to treat people with attention deficit disorder can be used effectively to help decrease impulsivity and hyperactivity. Given the side effects associated with these medications, particularly, antipsychotic medications, a need exists to develop new therapeutics for treating ASD and its related symptoms.

Depression is a common feature of mental illness, whatever its nature and origin. A person with a history of any serious psychiatric disorder has almost as high a chance of developing major depression as someone who has had major depression itself in the past. About 20% of the U.S. population reports at least one depressive symptom in a given month, and 12% report two or more in a year. Mood disorders represent a category of mental disorders in which the underlying problem primarily affects a person's persistent emotional state (their mood). Bipolar disorder is less common, occurring at a rate of 1% in the general population, but some believe the diagnosis is often overlooked because manic elation is too rarely reported as an illness. Bipolar disorder is an illness involving one or more episodes of serious mania and depression. Sometimes a person might only experience symptoms of mania. If a person only experiences feelings of sadness, this is considered depression. During episodes of bipolar disorder, a person's mood can swing from excessively "high" and/or irritable to sad and hopeless, with periods of a normal mood in between.

Major depressive disorder is one of the most common mental illnesses. Depression causes people to lose pleasure from daily life, can complicate other medical conditions, and can even be serious enough to lead to suicide. Depression can occur to anyone, at any age, and to people of any race or ethnic group. Depression is usually treated with medications, psychotherapy, or a combination of the two. Medications for major depressive disorder fall in multiple drug classes, including tricyclic antidepressants, monoamine oxidase inhibitors, selective serotonin reuptake inhibitors, and atypical antidepressants. However, most antidepressants require at least 4-6 weeks for onset of effectiveness, and many antidepressants have unpleasant side effects. Moreover, as many as two-thirds of patients with depression experience treatment failure with the first anti-depressant, and up to a third of patients with depression don't respond to several attempts at treatment. Given the unpleasant and potentially severe side effects associated with these medications, a need exists to develop new therapeutics for treating depression in mood disorders and their related symptoms.

Rett syndrome (RTT), originally termed cerebroatrophic hyperammonemia, is a rare genetic postnatal neurological disorder of the grey matter of the brain that affects both females and male patients, with predominance of female ones. Rett syndrome causes problems in brain function that are responsible for cognitive, sensory, emotional, motor, and autonomic function. Most frequent problems that occur include those involving learning, speech, sensory sensations, mood, movement, breathing, cardiac function, chewing, swallowing, and digestion. It is characterized by normal early growth and development followed by a slowing of development, loss of purposeful use of the hands, distinctive hand movements, slowed brain and head growth, problems with walking, seizures, and intellectual disability. In particular, repetitive stereotyped hand movements, such as wringing and/or repeatedly putting hands into the mouth, are usual symptoms. Apraxia—the inability to perform motor functions—is perhaps the most severely disabling feature of Rett syndrome, interfering with every body movement, including eye gaze and speech. Children with Rett syndrome often exhibit autistic-like behaviors in the early stages (http://www.ninds.nih.gov/disorders/rett/detail_rett.htm).

Nearly all cases of Rett syndrome are caused by a mutation in the methyl CpG binding protein 2, or MECP2 gene. The MECP2 gene contains instructions for the synthesis of a protein called methyl cytosine binding protein 2 (MeCP2), which is needed for brain development and acts as one of the many biochemical switches that can either increase gene expression or tell other genes when to turn off and stop producing their own unique proteins. Because the MECP2 gene does not function properly in individuals with Rett syndrome, insufficient amounts or structurally abnormal forms of the protein are produced and can cause other genes to be abnormally expressed. However, not everyone who has an MECP2 mutation has Rett syndrome. Although Rett syndrome is a genetic disorder, less than 1 percent of recorded cases are inherited or passed from one generation to the next. Most cases are spontaneous, which means the mutation occurs randomly. Rett syndrome is estimated to affect one in every 10,000 to 15,000 live female births and in all racial and ethnic groups worldwide.

Currently, there is no cure to Rett syndrome. Treatment for the disorder is symptomatic—focusing on the management of symptoms—and supportive, requiring a multidisciplinary approach. Bromocriptine and carbidopa-levodopa, which are dopamine agonists, have been tried as treatments for motor dysfunction in persons with Rett syndrome. However, benefits are neither substantial nor long lasting. Thus, a need exists to develop new therapeutics for treating Rett syndrome and its related symptoms.

Chorea-acanthocytosis (ChAc) is a neurological disorder that affects movements in many parts of the body. Chorea refers to the involuntary jerking movements made by people with this disorder. People with this condition also have abnormal star-shaped red blood cells (acanthocytosis). This disorder is one of a group of conditions called neuroacanthocytoses that involve neurological problems and abnormal red blood cells. Clinically is characterized by a Huntington disease-like phenotype with progressive neurological symptoms including movement disorders, psychiatric manifestations and cognitive disturbances. Chorea may also be associated with Huntington's disease, and the methods and compositions provided herein may be employed to treat the same.

Prevalence and incidence of chorea-acanthocytosis are not known, but it is estimated that there are around 1,000 cases worldwide. Onset is in early adulthood and the initial presentation is often subtle cognitive or psychiatric symptoms. During the course of the disease, most patients develop a characteristic phenotype including chorea. Most patients develop generalized chorea and some degree of parkinsonism. Impairment of memory and executive functions is frequent. Psychiatric manifestations are common and may present as schizophrenia-like psychosis or obsessive compulsive disorder (OCD). Chorea-acanthocytosis usually progresses slowly over 15-30 years, but sudden death, presumably caused by seizures or autonomic involvement, may occur.

Chorea-acanthocytosis is caused by various mutations in the VPS13A gene coding for chorein. No obvious genotype-phenotype correlations have been observed. This condition is inherited in an autosomal recessive pattern, which means both copies of the gene in each cell have mutations. The parents of an individual with an autosomal recessive condition each carry one copy of the mutated gene, but they typically do not show signs and symptoms of the condition. No curative or disease-modifying treatments are currently available and management is purely symptomatic. Thus, a need exists to develop new therapeutics for treating Chorea-acanthocytosis and its related symptoms.

Accordingly, in various embodiments as disclosed herein, methods are provided for treating a hyperkinetic movement disorder in a subject in need thereof by administering to the subject in need thereof a pharmaceutically effective amount of a VMAT2 inhibitor described herein, or a pharmaceutical composition comprising the same. In one embodiment, the hyperkinetic movement disorder is tardive dyskinesia, Tourette's syndrome, Huntington's disease, chorea associated with Huntington's disease, or tics. In other embodiments, the hyperkinetic movement disorder is ataxia, chorea, dystonia, hemifacial spasm, myoclonus, restless leg syndrome, or tremors.

In other embodiments, methods are provided for treating a neurological and/or psychiatric diseases and disorders in a subject in need thereof by administering to the subject in need thereof a pharmaceutically effective amount of a VMAT2 inhibitor described herein or a pharmaceutical composition comprising the same.

In one embodiment, the neurological and/or psychiatric disease or disorder is hyperkinetic movement disorder, mood disorder, bipolar disorder, schizophrenia, schizoaffective disorder, mania in mood disorder, depression in mood disorder, treatment-refractory obsessive compulsive disorder, neurological dysfunction associated with Lesch-Nyhan syndrome, agitation associated with Alzheimer's disease, Fragile X syndrome or Fragile X-associated tremor-ataxia syndrome, autism spectrum disorder, Rett syndrome, or chorea-acanthocytosis.

In some embodiments, the neurological or psychiatric disease or disorder is a hyperkinetic movement disorder.

In some embodiments, the hyperkinetic movement disorder is tardive dyskinesia.

In some embodiments, the hyperkinetic movement disorder is Tourette's syndrome.

In some embodiments, the hyperkinetic movement disorder is Huntington's disease.

In some embodiments, the hyperkinetic movement disorder is tics.

In some embodiments, the hyperkinetic movement disorder is chorea associated with Huntington's disease.

In some embodiments, the hyperkinetic movement disorder is ataxia, chorea, dystonia, hemifacial spasm, Huntington's disease, myoclonus, restless leg syndrome, or tremors.

In some embodiments, the neurological or psychiatric disease or disorder is restricted and repetitive behaviors associated with Autism spectrum disorder (ASD).

In some embodiments, the neurological or psychiatric disease or disorder is obsessions and compulsions in partial and non-responders (or completely refractory) with Obsessive-Compulsive Disorder (OCD). In some embodiments, the neurological or psychiatric disease or disorder is obsessions and compulsions in partial and non-responders (or completely refractory) with Obsessive-Compulsive Disorder (OCD) and the compounds described herein are administered as adjunctive therapy. In some embodiments, the compounds described here are administered as adjunctive therapy with the primary therapy being treatment with antidepressants.

In some embodiments, the neurological or psychiatric disease or disorder is Bipolar I Disorder. In some embodiments, the compound described herein is administered as monotherapy for the treatment of Bipolar I Disorder. In some embodiments, the compound described herein is administered as maintenance therapy for the treatment of Bipolar I Disorder. In some embodiments, the compound described herein is administered as monotherapy maintenance therapy for the treatment of Bipolar I Disorder.

In another embodiment, the VMAT2 inhibitors described herein may be hydrolyzed in the body of a mammal to compounds that may inhibit the human monoamine transporter isoform 2. As such, these VMAT2 inhibitors may have additional utility in altering the in vivo properties of the metabolite in a mammal such as the maximum concentration or duration of action.

In another embodiment, pharmaceutical compositions containing one or more monoamine re-uptake inhibitors (i.e., VMAT2 inhibitors) are disclosed. For the purposes of administration, the VMAT2 inhibitor described herein may be formulated as pharmaceutical compositions. Pharmaceutical compositions comprise one or more monoamine re-uptake inhibitor described herein and one or more pharmaceutically acceptable excipients and/or diluents. The VMAT2 inhibitor is present in the composition in an amount that is effective to treat a particular disorder—that is, in an amount sufficient to reduce the supply of monoamines in the central nervous system, and preferably with acceptable toxicity to the patient. Appropriate concentrations and dosages can be readily determined by one skilled in the art.

Characterizing any of the VMAT2 inhibitors described herein may be determined using methods described herein and in the art. For example, dopamine depletion may be determined using the locomotor activity (LMA) assay. Another in vivo animal model includes the conditioned avoidance response (CAR) test, which has been shown to be an effective and reliable preclinical model for assessing the antipsychotic activity of compounds.

Also provided is a VMAT2 inhibitor as described herein for production of a medication for use in the treatment of a neurological or psychiatric disease or disorder.

Also provided is a VMAT2 inhibitor as described herein or a pharmaceutical composition as described herein for use in a method of treatment of the human or animal body by therapy.

Also provided is a VMAT2 inhibitor as described herein or a pharmaceutical composition as described herein for use in a method for the treatment of a neurological or psychiatric disease or disorder in the human or animal body by therapy.

The present disclosure further provides for pharmaceutical compositions comprising one or more compounds described herein and one or more pharmaceutically acceptable excipients and/or diluents for use in the methods for treating neurological disorders and diseases, such as hyperkinetic movement disorders.

Pharmaceutically acceptable excipients and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a VMAT2 inhibitor, diluents, dispersing and surface active agents, binders, and lubricants. One skilled in this art may further formulate the VMAT2 inhibitor in an appropriate manner, and in accordance with accepted practices, such as those disclosed in *Remington's Pharmaceutical Sciences*, Gennaro, Ed., Mack Publishing Co., Easton, Pa. 1990.

The pharmaceutical compositions provided herein may be formulated as immediate or modified release dosage forms, including delayed-, sustained, pulsed-, controlled, targeted-, and programmed-release forms. The pharmaceutical compositions may also be formulated as a suspension, solid, semi-solid, or thixotropic liquid, for administration as an implanted depot.

The pharmaceutical compositions provided herein may be provided in unit dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The pharmaceutical compositions provided herein may be administered alone, or in combination with one or more other compounds provided herein, one or more other active ingredients. The pharmaceutical compositions provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art). The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pregelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Vee gum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as com starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, com oil, and soybean oil; zinc stearate; ethyl oleate; ethyl laureate; agar; starch; lycopodium; silica or silica gels, such as AEROSIL®200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant. Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation. The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems.

The pharmaceutical compositions provided herein may be provided as noneffervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide. Coloring and flavoring agents can be used in all of the above dosage forms. The pharmaceutical compositions provided herein may be formulated as immediate or modified release dosage forms, including delayed-, sustained, pulsed-, controlled-, targeted-, and programmed-release forms.

The pharmaceutical compositions provided herein may be co-formulated with other active ingredients which do not impair the desired therapeutic action, or with substances that supplement the desired action, such as antacids, proton pump inhibitors, and H2-receptor antagonists.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

Parenteral Administration

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science.

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl phydroxybenzates, thimerosal, benzalkonium chloride, benzethonium chloride, methyl- and propylparabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including alpha-cyclodextrin, beta-cyclodextrin, hydroxypropyl-beta-cyclodextrin, sulfobutylether-beta-cyclodextrin, and sulfobutylether 7-beta-cyclodextrin (CAPTISOL®, CyDex, Lenexa, Kans.).

The pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In certain embodiments, the pharmaceutical compositions are provided as ready-to-use sterile solutions. In certain embodiments, the pharmaceutical compositions are provided as sterile dry soluble products, including lyophilized powders and hypodermic tablets, to be reconstituted with a vehicle prior to use. In certain embodiments, the pharmaceutical compositions are provided as ready-to-use sterile suspensions. In certain embodiments, the pharmaceutical compositions are provided as sterile dry insoluble products to be reconstituted with a vehicle prior to use. In certain embodiments, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semisolid, or thixotropic liquid, for administration as an implanted depot. In certain embodiments, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Topical Administration

The pharmaceutical compositions provided herein may be administered topically to the skin, orifices, or mucosa. The topical administration, as used herein, include (intra)dermal, conjuctival, intracorneal, intraocular, ophthalmic, auricular, transdermal, nasal, vaginal, urethereal, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

The pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon bases, including such as lard, benzoinated lard, olive oil, cottonseed oil, and other oils, white petrolatum; emulsifiable or absorption bases, such as hydrophilic petrolatum, hydroxystearin sulfate, and anhydrous lanolin; water-removable bases, such as hydrophilic ointment; water-soluble ointment bases, including polyethylene glycols of varying molecular weight; emulsion bases, either water-in-oil (W/O) emulsions or oil-in-water (O/W) emulsions, including cetyl alcohol, glyceryl monostearate, lanolin, and stearic acid. These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as 50 micrometers or less, or 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as /-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile- or pulsed-, controlled-, accelerated- and fast-, targeted-, programmed-release, and gastric retention dosage forms.

The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

The pharmaceutical compositions provided herein in a modified release dosage form may be fabricated using a matrix controlled release device known to those skilled in the art.

In certain embodiments, the pharmaceutical compositions provided herein in a modified release dosage form is formulated using an erodible matrix device, which is water swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acidglycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In certain embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as camauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients in the compositions.

The pharmaceutical compositions provided herein in a modified release dosage form may be prepared by methods known to those skilled in the art, including direct compression, dry or wet granulation followed by compression, melt-granulation followed by compression.

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents waterswellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-tolunesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CAethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water, as disclosed in U.S. Pat. No. 5,798,119. Such hydrophobic but water-permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes. The delivery port(s) on the semipermeable membrane may be formed postcoating by mechanical or laser drilling. Delivery port(s) may also be formed in situ by erosion of a plug of water-soluble material or by rupture of a thinner portion of the membrane over an indentation in the core. In addition, delivery ports may be formed during coating process.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients as described herein to promote performance or processing of the formulation.

The osmotic controlled-release dosage forms can be prepared according to conventional methods and techniques known to those skilled in the art.

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), hydroxylethyl cellulose, and other pharmaceutically acceptable excipients.

The pharmaceutical compositions provided herein in a modified release dosage form may be fabricated a multiparticulate controlled release device, which comprises a multiplicity of particles, granules, or pellets, ranging from about 10 pm to about 3 mm, about 50 pm to about 2.5 mm, or from about 100 pm to 1 mm in diameter. Such multiparticulates may be made by the processes know to those skilled in the art, including wet- and dry-granulation, extrusion/spheronization, roller-compaction, melt-congealing, and by spray-coating seed cores.

Other excipients as described herein may be blended with the pharmaceutical compositions to aid in processing and forming the multiparticulates. The resulting particles may themselves constitute the multiparticulate device or may be coated by various filmforming materials, such as enteric polymers, water-swellable, and water-soluble polymers. The multiparticulates can be further processed as a capsule or a tablet.

Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems.

Systemic Delivery

In another embodiment, a method is provided herein for treating disorders of the central or peripheral nervous system. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the VMAT2 inhibitors described herein can be prepared in aqueous injection solutions which may contain, in addition to the VMAT2 inhibitor, buffers, antioxidants, bacteriostats, and other additives commonly employed in such solutions.

Dosages

In the treatment, prevention, or amelioration of one or more symptoms of tic disorders or other conditions, disorders or diseases associated with VMAT2 inhibition, an appropriate dosage level generally is about 0.001 to 100 mg per kg patient body weight per day (mg/kg per day), about 0.01 to about 80 mg/kg per day, about 0.1 to about 50 mg/kg per day, about 0.5 to about 25 mg/kg per day, or about 1 to about 20 mg/kg per day, which may be administered in single or multiple doses. Within this range the dosage may be 0.005 to 0.05, 0.05 to 0.5, or 0.5 to 5.0, 1 to 15, 1 to 20, or 1 to 50 mg/kg per day. In certain embodiments, the dosage level is about 0.001 to 100 mg/kg per day.

In certain embodiments, the dosage level is about from 25 to 100 mg/kg per day. In certain embodiments, the dosage level is about 0.01 to about 40 mg/kg per day. In certain embodiments, the dosage level is about 0.1 to about 80 mg/kg per day. In certain embodiments, the dosage level is about 0.1 to about 50 mg/kg per day. In certain embodiments, the dosage level is about 0.1 to about 40 mg/kg per day. In certain embodiments, the dosage level is about 0.5 to about 80 mg/kg per day. In certain embodiments, the dosage level is about 0.5 to about 40 mg/kg per day. In certain embodiments, the dosage level is about 0.5 to about 25 mg/kg per day. In certain embodiments, the dosage level is about 1 to about 80 mg/kg per day. In certain embodiments, the dosage level is about 1 to about 75 mg/kg per day. In certain embodiments, the dosage level is about 1 to about 50 mg/kg per day. In certain embodiments, the dosage level is about 1 to about 40 mg/kg per day. In certain embodiments, the dosage level is about 1 to about 25 mg/kg per day.

In certain embodiments, the dosage level is about from 5.0 to 150 mg per day, and in certain embodiments from 10 to 100 mg per day. In certain embodiments, the dosage level is about 80 mg per day. In certain embodiments, the dosage level is about 40 mg per day.

For oral administration, the pharmaceutical compositions can be provided in the form of tablets containing 1.0 to 1,000 mg of the active ingredient, particularly about 1, about 5, about 10, about 15, about 20, about 25, about 30, about 40, about 45, about 50, about 75, about 80, about 100, about 150, about 200, about 250, about 300, about 400, about 500, about 600, about 750, about 800, about 900, and about 1,000 mg of the active ingredient for the symptomatic adjustment of the dosage to the patient to be treated. In certain embodiments, the pharmaceutical compositions can be provided in the form of tablets containing about 100 mg of the active ingredient. In certain embodiments, the pharmaceutical compositions can be provided in the form of tablets containing about 80 mg of the active ingredient. In certain embodiments, the pharmaceutical compositions can be provided in the form of tablets containing about 75 mg of the active ingredient. In certain embodiments, the pharmaceutical compositions can be provided in the form of tablets containing about 50 mg of the active ingredient. In certain embodiments, the pharmaceutical compositions can be provided in the form of tablets containing about 40 mg of the active ingredient. In certain embodiments, the pharmaceutical compositions can be provided in the form of tablets containing about 25 mg of the active ingredient. The compositions may be administered on a regimen of 1 to 4 times per day, including once, twice, three times, and four times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds provided herein may also be combined or used in combination with other agents useful in the treatment, prevention, or amelioration of one or more symptoms of the diseases or conditions for which the compounds provided herein are useful.

Such other agents, or drugs, may be administered, by a route and in an amount commonly used thereof, simultaneously or sequentially with the compounds provided herein. When compounds provided herein are used contemporaneously with one or more other drugs, a pharmaceutical composition containing such other drugs in addition to the compounds provided herein may be utilized, but is not required. Accordingly, the pharmaceutical compositions provided herein include those that also contain one or more other active ingredients or therapeutic agents, in addition to the compounds provided herein.

The weight ratio of the compounds provided herein to the second active ingredient may be varied, and will depend upon the effective dose of each ingredient. Generally, an effective dose of each will be used. Thus, for example, when the compounds provided herein are used in combination with the second drug, or a pharmaceutical composition containing such other drug, the weight ratio of the particulates to the second drug may range from about 1,000:1 to about 1:1,000, or about 200:1 to about 1:200.

Combinations of the particulates provided herein and other active ingredients will generally also be within the aforementioned range, but in each case, an effective dose of each active ingredient should be used.

Examples of embodiments of the present disclosure are provided in the following examples. The following examples are presented only by way of illustration and to assist one of ordinary skill in using the disclosure. The examples are not intended in any way to otherwise limit the scope of the disclosure.

EXAMPLES

Analytical Method—Ultra-High Performance Liquid Chromatography (UPLC-MS)

Platform: Agilent 1260 series UPLC: equipped with an auto-sampler, an UV detector (220 nM and 254 nM), column thermostat, a MS detector (electrospray);

Column: Waters XBridge BEH C18 XP, 2.5 micron, 3×50 mm;

Mobile phase: A=water, 0.025% TFA; B=acetonitrile, 0.025% TFA;

Flow rate: 1.5 mL/min;

Gradient: 10% B/90% A to 90% B/10% A over 1.5 min, then hold 0.3 min, return to initial conditions for 0.5 min; total run time 2.5 min;

For purpose of abbreviation, some nitrogen atoms and/or oxygen atoms are depicted in the following Examples absent their accompanying hydrogen atoms, such as monovalent "—N" in place of "—NH$_2$" and "—O" in place of "—OH", and divalent "—N—" in place of "—NH—". One skilled in this field will radially recognize and appreciate the meaning of such abbreviated designations.

Example 1

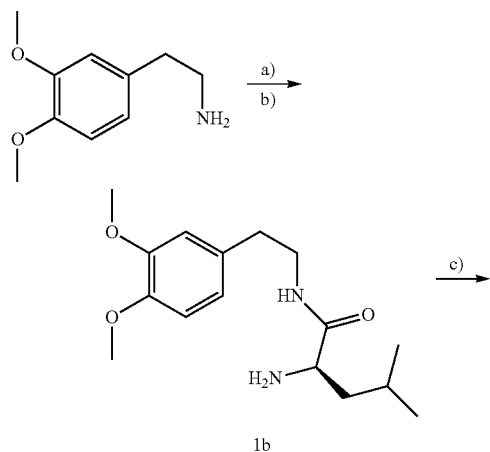

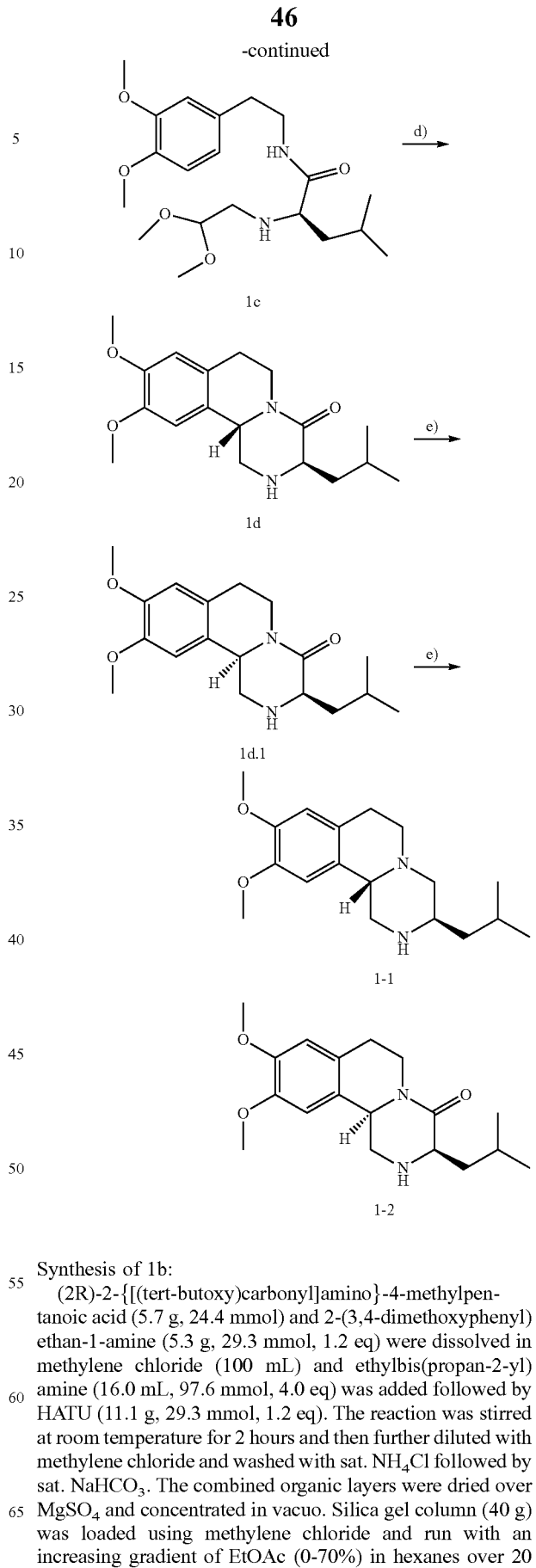

Synthesis of 1b:

(2R)-2-{[(tert-butoxy)carbonyl]amino}-4-methylpentanoic acid (5.7 g, 24.4 mmol) and 2-(3,4-dimethoxyphenyl)ethan-1-amine (5.3 g, 29.3 mmol, 1.2 eq) were dissolved in methylene chloride (100 mL) and ethylbis(propan-2-yl)amine (16.0 mL, 97.6 mmol, 4.0 eq) was added followed by HATU (11.1 g, 29.3 mmol, 1.2 eq). The reaction was stirred at room temperature for 2 hours and then further diluted with methylene chloride and washed with sat. NH$_4$Cl followed by sat. NaHCO$_3$. The combined organic layers were dried over MgSO$_4$ and concentrated in vacuo. Silica gel column (40 g) was loaded using methylene chloride and run with an increasing gradient of EtOAc (0-70%) in hexanes over 20 min to provide tert-butyl N-[(1R)-1-{[2-(3,4-dimethoxyphenyl)ethyl]carbamoyl}-3-methylbutyl]carbamate 1a (9.7 g, 24.4 mmol) in quantitative yield. Tert-butyl N-[(1R)-1-{[2-(3,4-dimethoxyphenyl)ethyl]carbamoyl}-3-methylbutyl]carbamate 1a (6.5 g, 16.0 mmol) was dissolved in methylene chloride (100 mL) and trifluoracetic acid (20 mL) was added. Once the reaction was complete, the mixture was concentrated, redissolved in methylene chloride (100 mL) and made basic with sat. NaHCO₃. The combined organic layers were dried over MgSO₄ and concentrated in vacuo to provide (2R)-2-amino-N-[2-(3,4-dimethoxyphenyl)ethyl]-4-methylpentanamide 1b (4.6 g, 16.0 mmol) as a yellow oil in quantitative yield.

Synthesis of 1c:

(2R)-2-amino-N—[2-(3,4-dimethoxyphenyl)ethyl]-4-methylpentanamide 1b (4.6 g, 16.0 mmol) was dissolved in methanol (100 mL) and 2,2-dimethoxyacetaldehyde (60 wt. % in water) (3.2 mL, 18.0 mmol, 1.1 eq) was added. Acetic acid was added until neutral, then catalytic 10% palladium on carbon was added and the reaction mixture was purged with hydrogen and stirred over the weekend. The mixture was filtered through celite and concentrated in vacuo. Silica gel column (40 g) was loaded using methylene chloride and run with an increasing gradient of methanol (0-10%) in methylene chloride over 20 min to provide (2R)-2-[(2,2-dimethoxyethyl)amino]-N—[2-(3,4-dimethoxyphenyl)ethyl]-4-methylpentanamide 1c as a yellow oil (5.8 g, 15.0 mmol) in a 94% yield.

Synthesis of 1d and 1d.1:

Concentrated sulfuric acid (10 mL) was cooled to 0° C. and (2R)-2-[(2,2-dimethoxyethyl)amino]-N-[2-(3,4-dimethoxyphenyl)ethyl]-4-methylpentanamide (5.8 g, 15.0 mmol) dissolved in methanol (10 mL) was added dropwise. The reaction was warmed to room temp and stirred overnight. Starting material was observed so the reaction was heated to 60° C. for 2 hours and reaction was complete. The reaction mixture was cooled by addition of ice then made basic with 10% NaOH. The methanol was removed in vacuo and the compound was extracted with methylene chloride (3×100 mL). The combined organic layers were dried over MgSO₄ and concentrated in vacuo. Silica gel column (80 g) was loaded using methylene chloride and run with an increasing gradient of methanol (0-5%) in methylene chloride over 40 min to provide (3R,1bS)-9,10-dimethoxy-3-(2-methylpropyl)-1H,2H,3H,4H,6H,7H,11bH-piperazino[2,1-a]isoquinolin-4-one 1d (1.7 g, 5.3 mmol) and (3R,11bR)-9,10-dimethoxy-3-(2-methylpropyl)-1H,2H,3H,4H,6H,7H,11bH-piperazino[2,1-a]isoquinolin-4-one 1d.1 (2.1 g, 6.6 mmol).

Synthesis of 1-1 and 1-2:

(3R,1bS)-9,10-dimethoxy-3-(2-methylpropyl)-1H,2H,3H,4H,6H,7H,11bH-piperazino[2,1-a]isoquinolin-4-one 1d (0.6 g, 1.9 mmol) was dissolved in anhydrous THF (4 mL) and 2M LAH (2.9 ml, 5.6 mmol, 3 eq) was added. The reaction mixture was quenched with methanol (1 mL) and concentrated in vacuo. The mixture was redissolved in methylene chloride (10 mL) and extracted from brine. The combined organic layers were dried over MgSO₄ and concentrated in vacuo to provide (3R,11bS)-9,10-dimethoxy-3-(2-methylpropyl)-1H,2H,3H,4H,6H,7H,11bH-piperazino[2,1-a]isoquinoline 1-1 (0.5 g, 1.64 mmol) in 87% yield.

(3R,11bR)-9,10-dimethoxy-3-(2-methylpropyl)-1H,2H,3H,4H,6H,7H,11bH-piperazino[2,1-a]isoquinoline 1-2 was also made using this procedure.

Example 2

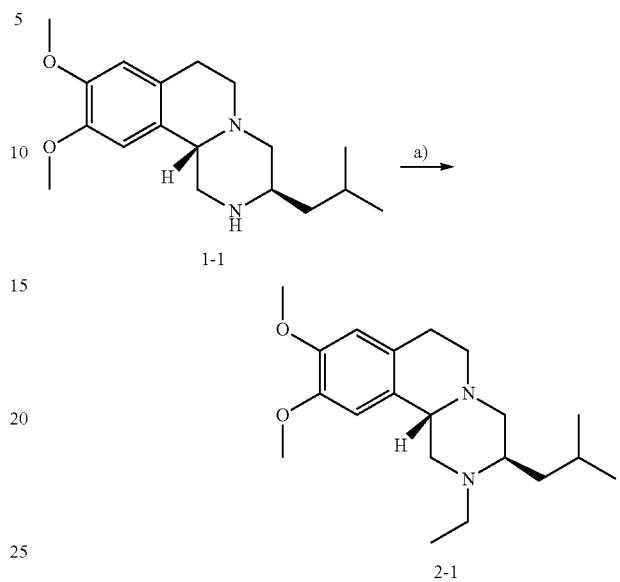

Synthesis of 2-1:

(3R,11bS)-9,10-dimethoxy-3-(2-methylpropyl)-1H,2H,3H,4H,6H,7H,11bH-piperazino[2,1-a]isoquinoline 1-1 (10 mg, 0.03 mmol) was dissolved in DMF (0.5 mL) and K₂CO₃ (14 mg, 0.1 mmol, 3 eq) was added followed by ethyl iodide (2.6 μL, 0.3 mmol, 1 eq). The reaction was complete after 2 hours then filtered and diluted to a total volume of 1 mL using MeOH and submitted directly for preparative chromatography yielding (3R,11b S)-2-ethyl-9,10-dimethoxy-3-(2-methylpropyl)-1H,2H,3H,4H,6H,7H,11bH-piperazino[2,1-a]isoquinoline 2-1.

Table 2 below provides the observed (Obs) ion m/z ratio for 2-1 and other representative compounds that were made according to the procedure as described in this example.

TABLE 2

| Cpd. No. | —R³ | Compound Name | Obs Ion (m/z) |
|---|---|---|---|
| 2-1 | —CH₂CH₃ | (3R,11bS)-2-ethyl-9,10-dimethoxy-3-(2-methylpropyl)-1H,2H,3H,4H,6H,7H,11bH-piperazino[2,1-a]isoquinoline | 333.1 |
| 2-2 | —CH₃ | (3R,11bS)-9,10-dimethoxy-2-methyl-3-(2-methylpropyl)-1H,2H,3H,4H,6H,7H,11bH-piperazino[2,1-a]isoquinoline | 319.1 |

TABLE 2-continued

| 2-3 | —CH₂CH(CH₃)₂ | (3R,11bS)-9,10-dimethoxy-2,3-bis(2-methylpropyl)-1H,2H,3H,4H,6H,7H,11bH-piperazino[2,1-a]isoquinoline | 361.1 |

Example 3

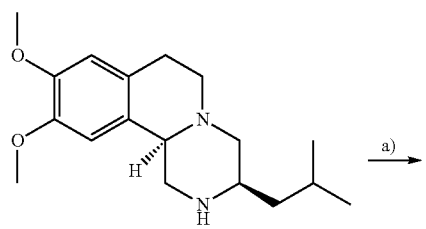

1-2 a)→

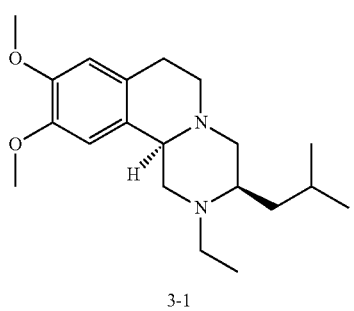

3-1

Synthesis of 3-1:

(3R,11bR)-9,10-dimethoxy-3-(2-methylpropyl)-1H,2H,3H,4H,6H,7H,11bH-piperazino[2,1-a]isoquinoline 1-2 (10 mg, 0.03 mmol) was dissolved in DMF (0.5 mL) and K₂CO₃ (14 mg, 0.1 mmol, 3 eq) was added followed by ethyl iodide (2.6 μL, 0.3 mmol, 1 eq). The reaction was complete after 2 hours then filtered and diluted to a total volume of 1 mL using MeOH and submitted directly for preparative chromatography yielding (3R,11bR)-2-ethyl-9,10-dimethoxy-3-(2-methylpropyl)-1H,2H,3H,4H,6H,7H,11bH-piperazino[2,1-a]isoquinoline 3-1.

Table 3 below provides the observed (Obs) ion m/z ratio for 3-1 and other representative compounds that were made according to the procedure as described in this example.

TABLE 3

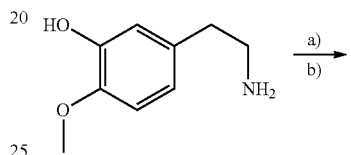

| Cpd. No. | —R³ | Compound Name | Obs Ion (m/z) |
|---|---|---|---|
| 3-1 | —CH₂CH₃ | (3R,11bR)-2-ethyl-9,10-dimethoxy-3-(2-methylpropyl)-1H,2H,3H,4H,6H,7H,11bH-piperazino[2,1-a]isoquinoline | 333.1 |
| 3-2 | —CH₃ | (3R,11bR)-9,10-dimethoxy-2-methyl-3-(2-methylpropyl)-1H,2H,3H,4H,6H,7H,11bH-piperazino[2,1-a]isoquinoline | 319.1 |
| 3-3 | —CH₂CH(CH₃)₂ | (3R,11bR)-9,10-dimethoxy-2,3-bis(2-methylpropyl)-1H,2H,3H,4H,6H,7H,11bH-piperazino[2,1-a]isoquinoline | 361.1 |

Example 4

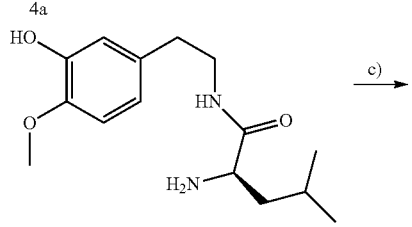

4a a)
b)

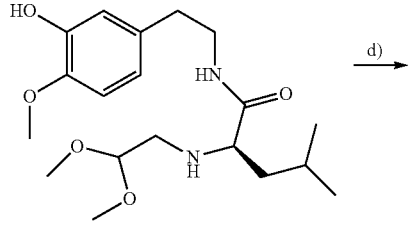

4b c)→

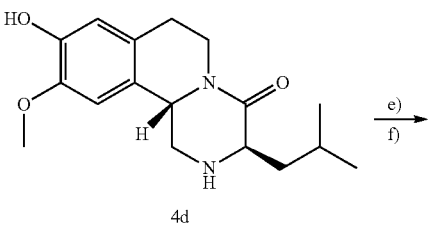

4c d)→

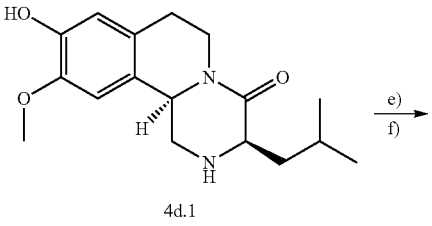

4d e)
f)→

4d.1 e)
f)→

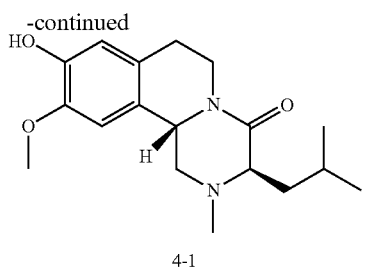

4-1

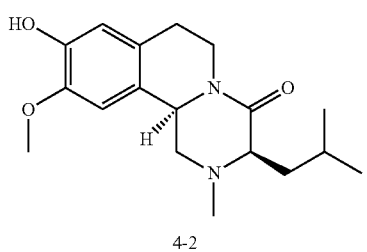

4-2

Synthesis of 4b:

(2R)-2-{[(tert-butoxy)carbonyl]amino}-4-methylpentanoic acid (3.0 g, 13.0 mmol, 1.2 eq) and 5-(2-aminoethyl)-2-methoxyphenol hydrochloride (2.2 g, 11.0 mmol) were dissolved in methylene chloride (50 mL) and triethylamine (4.5 mL, 33 mmol, 3.0 eq) was added followed by HATU (4.9 g, 13.0 mmol, 1.2 eq). The reaction was stirred at room temperature overnight and then further diluted with methylene chloride and washed with sat. NH$_4$Cl followed by sat. NaHCO$_3$. The combined organic layers were dried over MgSO$_4$ and concentrated in vacuo. Silica gel column (40 g) was loaded using methylene chloride and run with an increasing gradient of EtOAc (0-100%) in hexanes over 20 min to provide tert-butyl N-[(1R)-1-{[2-(3-hydroxy-4-methoxyphenyl)ethyl]carbamoyl}-3-methylbutyl]-carbamate (3.9 g, 10.4 mmol) in 95% yield. This intermediate was dissolved in methylene chloride (50 mL) and trifluoracetic acid (10 ml) was added. Once the reaction was complete, the mixture was concentrated, redissolved in methylene chloride (100 mL) and made basic with sat. NaHCO$_3$. The combined organic layers were dried over MgSO$_4$ and concentrated in vacuo to provide (2R)-2-amino-N—[2-(3-hydroxy-4-methoxyphenyl)ethyl]-4-methylpentanamide 4b (2.9 g, 10.4 mmol) as a yellow oil in quantitative yield.

Synthesis of 4c:

Intermediate 4b (2.9 g, 10.4 mmol) was dissolved in methanol (20 mL) and 2,2-dimethoxyacetaldehyde (60 wt. % in water, 2.0 mL, 11.5 mmol, 1.1 eq) was added. Acetic acid was added until neutral then catalytic 10% palladium on carbon was added and the reaction mixture was purged with hydrogen and stirred overnight. The mixture was filtered through celite and concentrated in vacuo. Silica gel column (40 g) was loaded using methylene chloride and run with an increasing gradient of methanol (0-10%) in methylene chloride over 20 min to provide (2R)-2-[(2,2-dimethoxyethyl)amino]-N—[2-(3-hydroxy-4-methoxyphenyl)ethyl]-4-methylpentanamide 4c as a yellow oil (3.9 g, 10.4 mmol) in a quantitative yield.

Synthesis of 4d and 4d.1:

Concentrated sulfuric acid (15 ml) was cooled to 0° C. and 4c (3.9 g, 10.7 mmol) dissolved in methanol (10 mL) was added dropwise. The reaction was warmed to room temp and stirred over the weekend. The reaction mixture was cooled by addition of ice then made just basic with 10% NaOH. The methanol was removed in vacuo and the compound was extracted with methylene chloride (3×100 mL). The combined organic layers were dried over MgSO$_4$ and concentrated in vacuo. Silica gel column (80 g) was loaded using methylene chloride and run with an increasing gradient of methanol (0-5%) in methylene chloride over 40 min to provide (3R,1bS)-9-hydroxy-10-methoxy-3-(2-methylpropyl)-1H,2H,3H,4H,6H,7H,11bH-piperazino[2,1-a]isoquinolin-4-one 4d (0.96 g, 3.2 mmol) and (3R,11bR)-9-hydroxy-10-methoxy-3-(2-methylpropyl)-1H,2H,3H,4H,6H,7H,11bH-piperazino[2,1-a]isoquinolin-4-one 4d.1 (1.1 g, 3.6 mmol).

Synthesis of 4-1 and 4-2:

Intermediate 4d (0.33 g, 1.1 mmol) was dissolved in methylene chloride (5 mL) and triethylamine (0.18 mL, 1.3 mmol, 1.2 eq) added followed by di-tert-butyl dicarbonate (0.28 g, 1.3 mmol, 1.2 eq). The reaction stirred overnight then concentrated in vacuo. Silica gel column (24 g) was loaded using methylene chloride and run with an increasing gradient of ethyl acetate (0-65%) in hexanes over 15 min to provide tert-butyl (3R,11bS)-9-hydroxy-10-methoxy-3-(2-methylpropyl)-4-oxo-1H,2H,3H,4H,6H,7H,11bH-piperazino[2,1-a]isoquinoline-2-carboxylate (0.44 g, 1.1 mmol) in quantitative yield. This intermediate (0.62 g, 1.53 mmol) was dissolved in anhydrous THF (10 mL) and 2M LAH (3.8 ml, 7.7 mmol, 5 eq) was added. The reaction mixture was stirred at room temperature for 2 hr then heated to 70° C. overnight. The mixture was quenched with water (1 mL) and diluted with EtOAc (20 mL). The product was extracted with EtOAc (3×25 ml) from Rochelle's salt (10 mL). The combined organic layers were dried over MgSO$_4$ and concentrated in vacuo to provide (3R,11bS)-10-methoxy-2-methyl-3-(2-methylpropyl)-1H,2H,3H,4H,6H,7H,11bH-piperazino[2,1-a]isoquinolin-9-ol 4-1 (0.45 g, 1.48 mmol) in 96% yield.

(3R,11bR)-10-methoxy-2-methyl-3-(2-methylpropyl)-1H,2H,3H,4H,6H,7H,11bH-piperazino[2,1-a]isoquinolin-9-ol 4-2 was also made using this procedure.

Example 5

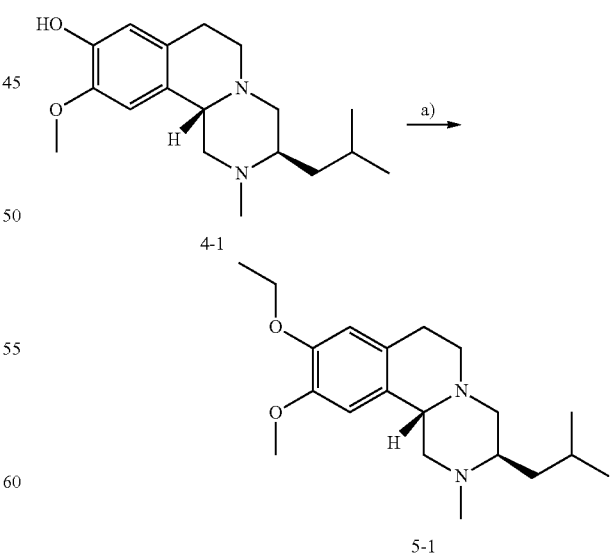

Synthesis of 5-1:

(3R,11bS)-10-methoxy-2-methyl-3-(2-methylpropyl)-1H,2H,3H,4H,6H,7H,11bH-piperazino-[2,1-a]isoquinolin- 9-ol 4-1 (8.0 mg, 0.026 mmol) was dissolved in acetone (0.5 mL) and Cs$_2$CO$_3$ (25.0 mg, 0.078 mmol, 3 equiv.) was added followed by bromoethane (2.0 µl, 0.029 mmol, 1.1 equiv). The reaction mixture was heated to 50° C. overnight. The crude mixture was filtered, diluted to 1 mL with MeOH, and submitted directly for preparative chromatography yielding (3R,11bS)-9-ethoxy-10-methoxy-2-methyl-3-(2-methylpropyl)-1H,2H,3H,4H,6H,7H,11bH-piperazino[2,1-a]-isoquinoline 5-1.

Table 5 below provides the observed (Obs) ion m/z ratio for 5-1 and other representative compounds that were made according to the procedure as described in this example.

TABLE 5

| Cpd. No. | —R¹ | Compound Name | Obs Ion (m/z) |
|---|---|---|---|
| 5-1 | —CH$_2$CH$_3$ | (3R,11bS)-9-ethoxy-10-methoxy-2-methyl-3-(2-methylpropyl)-1H,2H,3H,4H,6H,7H,11bH-piperazino[2,1-a]isoquinoline | 333.25 |
| 5-2 | —CH(CH$_3$)$_2$ | (3R,11bS)-10-methoxy-2-methyl-3-(2-methylpropyl)-9-(propan-2-yloxy)-1H,2H,3H,4H,6H,7H,11bH-piperazino[2,1-a]isoquinoline | 347.1 |
| 5-3 | —CH$_2$CH$_2$CH$_2$F | (3R,11bS)-9-(3-fluoropropoxy)-10-methoxy-2-methyl-3-(2-methylpropyl)-1H,2H,3H,4H,6H,7H,11bH-piperazino[2,1-a]isoquinoline | 365.1 |
| 5-4 | —CH$_2$CH$_2$F | (3R,11bS)-9-(2-fluoroethoxy)-10-methoxy-2-methyl-3-(2-methylpropyl)-1H,2H,3H,4H,6H,7H,11bH-piperazino[2,1-a]isoquinoline | 351.1 |
| 5-5 | -cyclopropyl | (3R,11bS)-9-cyclopropoxy-10-methoxy-2-methyl-3-(2-methylpropyl)-1H,2H,3H,4H,6H,7H,11bH-piperazino[2,1-a]isoquinoline | 345.1 |
| 5-6 | —CH$_2$CH$_2$CH$_3$ | (3R,11bS)-10-methoxy-2-methyl-3-(2-methylpropyl)-9-propoxy-1H,2H,3H,4H,6H,7H,11bH-piperazino[2,1-a]isoquinoline | 347.1 |
| 5-7 | -cyclopentyl | (3R,11bS)-9-(cyclopentyloxy)-10-methoxy-2-methyl-3-(2-methylpropyl)-1H,2H,3H,4H,6H,7H,11bH-piperazino[2,1-a]isoquinoline | 373.1 |
| 5-8 | —CH$_2$(CH=CH$_2$) | (3R,11bS)-10-methoxy-2-methyl-3-(2-methylpropyl)-9-(prop-2-en-1-yloxy)-1H,2H,3H,4H,6H,7H,11bH-piperazino[2,1-a]isoquinoline | 345.2 |
| 5-9 | —CH$_2$CH(CH$_3$)$_2$ | (3R,11bS)-10-methoxy-2-methyl-9-(2-methylpropoxy)-3-(2-methylpropyl)-1H,2H,3H,4H,6H,7H,11bH-piperazino[2,1-a]isoquinoline | 361.1 |
| 5-10 | —CH$_2$CH$_2$OCH$_3$ | (3R,11bS)-10-methoxy-9-(2-methoxyethoxy)-2-methyl-3-(2-methylpropyl)-1H,2H,3H,4H,6H,7H,11bH-piperazino[2,1-a]isoquinoline | 363.1 |
| 5-11 | -CH$_2$-cyclobutyl | (3R,11bS)-9-(cyclobutylmethoxy)-10-methoxy-2-methyl-3-(2-methylpropyl)-1H,2H,3H,4H,6H,7H,11bH-piperazino[2,1-a]isoquinoline | 373.1 |

TABLE 5-continued

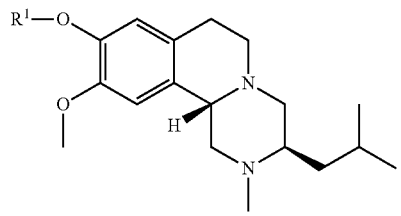

| Cpd. No. | —R¹ | Compound Name | Obs Ion (m/z) |
|---|---|---|---|
| 5-12 | —CH₂CH₂CH₂CN | 4-{[(3R,11bS)-10-methoxy-2-methyl-3-(2-methylpropyl)-1H,2H,3H,4H,6H,7H,11bH-piperazino[2,1-a]isoquinolin-9-yl]oxy}butanenitrile | 372.1 |
| 5-13 | —CH₂CH₂CH₂CF₃ | (3R,11bS)-10-methoxy-2-methyl-3-(2-methylpropyl)-9-(4,4,4-trifluorobutoxy)-1H,2H,3H,4H,6H,7H,11bH-piperazino[2,1-a]isoquinoline | 415.2 |
| 5-14 | —CH₂CH₂CH₂CH₂F | (3R,11bS)-9-(4-fluorobutoxy)-10-methoxy-2-methyl-3-(2-methylpropyl)-1H,2H,3H,4H,6H,7H,11bH-piperazino[2,1-a]isoquinoline | 379.1 |
| 5-15 | cyclopropylmethyl | (3R,11bS)-9-(cyclopropylmethoxy)-10-methoxy-2-methyl-3-(2-methylpropyl)-1H,2H,3H,4H,6H,7H,11bH-piperazino[2,1-a]isoquinoline | 359.1 |
| 5-16 | -cyclobutyl | (3R,11bS)-9-cyclobutoxy-10-methoxy-2-methyl-3-(2-methylpropyl)-1H,2H,3H,4H,6H,7H,11bH-piperazino[2,1-a]isoquinoline | 359.1 |
| 5-17 | —CH₂CF₃ | (3R,11bS)-10-methoxy-2-methyl-3-(2-methylpropyl)-9-(2,2,2-trifluoroethoxy)-1H,2H,3H,4H,6H,7H,11bH-piperazino[2,1-a]isoquinoline | 387.2 |
| 5-18 | (2,2-difluorocyclopropyl)methyl | (3R,11bS)-9-[(2,2-difluorocyclopropyl)methoxy]-10-methoxy-2-methyl-3-(2-methylpropyl)-1H,2H,3H,4H,6H,7H,11bH-piperazino[2,1-a]isoquinoline | 395.1 |
| 5-19 | —CH₂CH₂CF₃ | (3R,11bS)-10-methoxy-2-methyl-3-(2-methylpropyl)-9-(3,3,3-trifluoropropoxy)-1H,2H,3H,4H,6H,7H,11bH-piperazino[2,1-a]isoquinoline | 401.2 |

Example 6

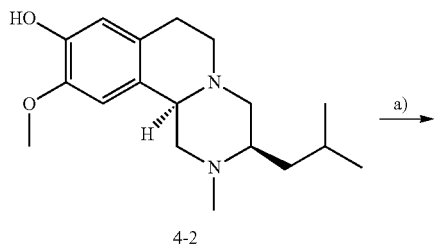

4-2 a)→

-continued

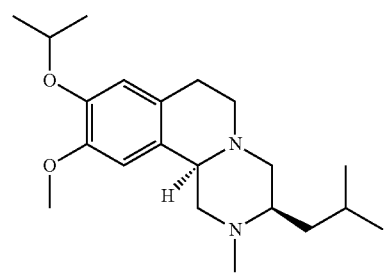

6-1

Synthesis of 6-1:

(3R,11bR)-10-methoxy-2-methyl-3-(2-methylpropyl)-1H,2H,3H,4H,6H,7H,11bH-piperazino[2,1-a]isoquinolin-9-ol 4-2 (10.0 mg, 0.033 mmol) was dissolved in acetone (0.5 mL) and $Cs_2CO_3$ (32.0 mg, 0.099 mmol, 3 equiv.) was added followed by 2-bromopropane (4.7 μl, 0.050 mmol, 1.5 equiv). The reaction mixture was heated to 50° C. overnight. The crude mixture was filtered, diluted to 1 ml with MeOH, and submitted directly for preparative chromatography yielding (3R,11bR)-10-methoxy-2-methyl-3-(2-methylpropyl)-9-(propan-2-yloxy)-1H,2H,3H,4H,6H,7H,11bH-piperazino[2,1-a]isoquinoline 6-1.

Table 6 below provides the observed (Obs) ion m/z ratio for 6-1 and other representative compounds that were made according to the procedure as described in this example.

TABLE 6

| Cpd. No. | —R¹ | Compound Name | Obs Ion (m/z) |
|---|---|---|---|
| 6-1 | —CH(CH₃)₂ | (3R,11bR)-10-methoxy-2-methyl-3-(2-methylpropyl)-9-(propan-2-yloxy)-1H,2H,3H,4H,6H,7H,11bH-piperazino[2,1-a]isoquinoline | 347.1 |
| 6-2 | —CH₂CH₂CH₂F | (3R,11bR)-9-(3-fluoropropoxy)-10-methoxy-2-methyl-3-(2-methylpropyl)-1H,2H,3H,4H,6H,7H,11bH-piperazino[2,1-a]isoquinoline | 365.1 |
| 6-3 | —CH₂CH₂F | (3R,11bR)-9-(2-fluoroethoxy)-10-methoxy-2-methyl-3-(2-methylpropyl)-1H,2H,3H,4H,6H,7H,11bH-piperazino[2,1-a]isoquinoline | 351.1 |
| 6-4 | -cyclopropyl | (3R,11bR)-9-cyclopropoxy-10-methoxy-2-methyl-3-(2-methylpropyl)-1H,2H,3H,4H,6H,7H,11bH-piperazino[2,1-a]isoquinoline | 345.1 |

Example 7

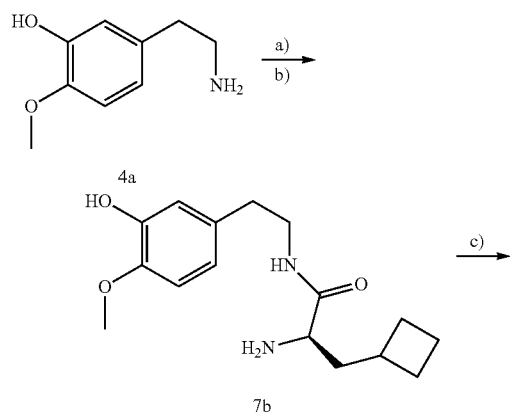

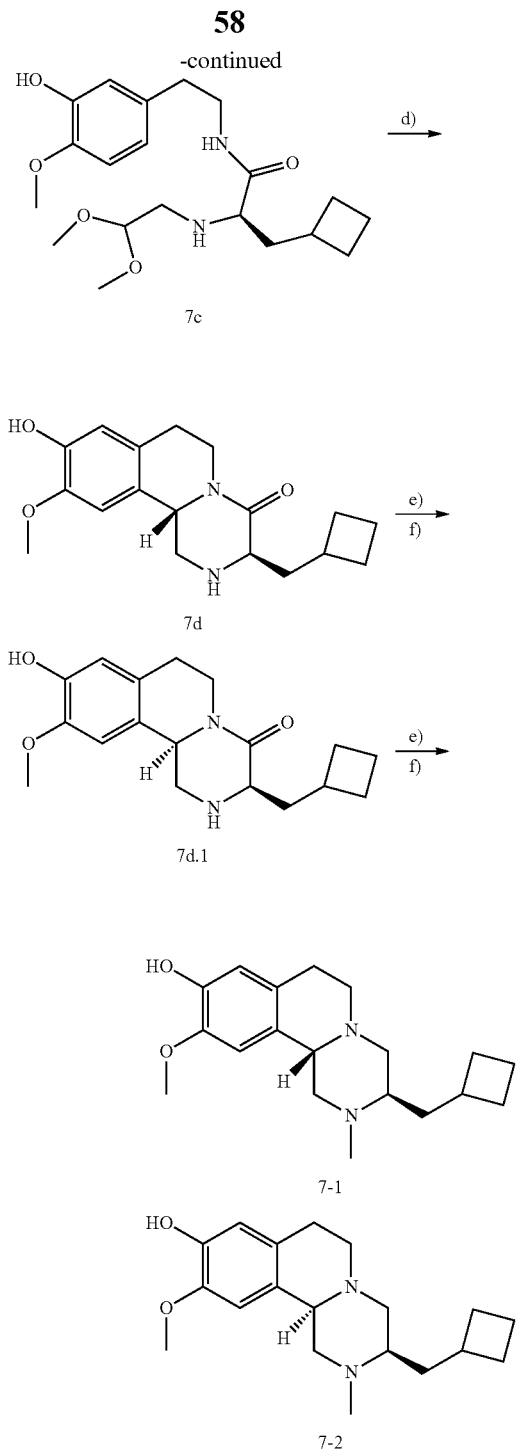

Synthesis of 7b:

(2R)-2-{[(tert-butoxy)carbonyl]amino}-3-cyclobutylpropanoic acid (0.86 g, 3.54 mmol, 1.0 eq,) and 5-(2-aminoethyl)-2-methoxyphenol hydrochloride (0.72 g, 3.54 mmol) were dissolved in methylene chloride (20 mL) and triethylamine (2.0 mL, 14.2 mmol, 4.0 eq) was added followed by HATU (1.6 g, 4.24 mmol, 1.2 eq). The reaction was stirred at room temperature overnight and then further diluted with methylene chloride and washed with sat. NH₄Cl followed by sat. NaHCO₃. The combined organic layers were dried over MgSO₄ and concentrated in vacuo. Silica gel column (24 g) was loaded using methylene chloride and run with an increasing gradient of EtOAc (0-100%) in hexanes over 20 min to provide tert-butyl (R)-(3-cyclobutyl-1-((3-hydroxy-4-methoxyphenethyl)amino)-1-oxopropan-2-yl)carbamate (1.0 g, 2.57 mmol) in 73% yield. This product (1.0 g, 2.57 mmol) was dissolved in methylene chloride (20 mL) and trifluoracetic acid (3 mL) added. Once the reaction was complete, the mixture was concentrated and redissolved in methylene chloride (50 mL) and made basic with sat. NaHCO$_3$. The combined organic layers were dried over MgSO$_4$ and concentrated in vacuo to provide (2R)-2-amino-3-cyclobutyl-N—[2-(3-hydroxy-4-methoxyphenyl)ethyl]propanamide 7b (0.68 g, 2.33 mmol) as a yellow oil in 91% yield.

Synthesis of 7c:

Intermediate 7b (0.68 g, 2.33 mmol) was dissolved in methanol (10 mL) and 2,2-dimethoxyacetaldehyde (60 wt. % in water) (0.42 mL, 2.33 mmol, 1.0 eq) was added. Acetic acid was added until neutral then catalytic 10% palladium on carbon was added and the reaction mixture was purged with hydrogen and stirred overnight. The mixture was filtered through celite, and concentrated in vacuo. Silica gel column (24 g) was loaded using methylene chloride and run with an increasing gradient of methanol (0-10%) in methylene chloride over 20 min to provide (2R)-3-cyclobutyl-2-[(2,2-dimethoxyethyl)amino]-N—[2-(3-hydroxy-4-methoxyphenyl)ethyl]propanamide 7c as a yellow oil (0.80 g, 2.1 mmol) in a 90% yield.

Synthesis of 7d and 7d.1:

Concentrated sulfuric acid (5 mL) was cooled to 0° C. and 7c (0.80 g, 2.1 mmol) dissolved in methanol (3 mL) was added dropwise. The reaction was warmed to room temp and stirred overnight. The reaction mixture was cooled by addition of ice then made just basic with 10% NaOH. The methanol was removed in vacuo and the compound was extracted with methylene chloride (3×50 mL). The combined organic layers were dried over MgSO$_4$ and concentrated in vacuo. Silica gel column (40 g) was loaded using methylene chloride and run with an increasing gradient of methanol (0-5%) in methylene chloride over 40 min to provide (3R,1bS)-3-(cyclobutylmethyl)-9-hydroxy-10-methoxy-1,2,3,6,7,11b-hexahydro-4H-pyrazino[2,1-a]isoquinolin-4-one 7d (0.28 g, 0.88 mmol) and (3R,1 bR)-3-(cyclobutylmethyl)-9-hydroxy-10-methoxy-1,2,3,6,7,11b-hexahydro-4H-pyrazino[2,1-a]isoquinolin-4-one 7d.1 (0.25 g, 0.79 mmol).

Synthesis of 7-1 and 7-2:

Intermediate 7d (0.28 g, 0.88 mmol) was dissolved in methylene chloride (5 mL) and triethylamine (0.18 mL, 1.3 mmol, 1.5 eq) added followed by di-tert-butyl dicarbonate (0.12 g, 0.97 mmol, 1.1 eq). The reaction stirred overnight then concentrated in vacuo. Silica gel column (12 g) was loaded using methylene chloride and run with an increasing gradient of ethyl acetate (0-65%) in hexanes over 15 min to provide tert-butyl (3R,11 bS)-3-(cyclobutylmethyl)-9-hydroxy-10-methoxy-4-oxo-1H,2H,3H,4H,6H,7H,11bH-piperazino[2,1-a]isoquinoline-2-carboxylate (0.28 g, 0.67 mmol) in 76% yield. This product (0.28 g, 0.67 mmol) was dissolved in anhydrous THF (5 mL) and 2M LAH (1.7 mL 3.4 mmol, 5 eq) was added. The reaction mixture was stirred at room temperature for 2 hr then heated to 70° C. overnight. The mixture was quenched with water (1 mL) and diluted with EtOAc (20 mL). The product was extracted with EtOAc (3×25 mL) from Rochelle's salt (10 mL). The combined organic layers were dried over MgSO$_4$ and concentrated in vacuo to provide (3R,11bS)-3-(cyclobutylmethyl)-10-methoxy-2-methyl-1H,2H,3H,4H,6H,7H, 11bH-piperazino[2,1-a]isoquinolin-9-ol 7-1 (0.17 g, 1.48 mmol) in 80% yield.

(3R,11bR)-(cyclobutylmethyl)-10-methoxy-2-methyl-1H,2H,3H,4H,6H,7H,11bH-piperazino[2,1-a]isoquinolin-9-ol 7-2 was also made using this procedure.

Example 8

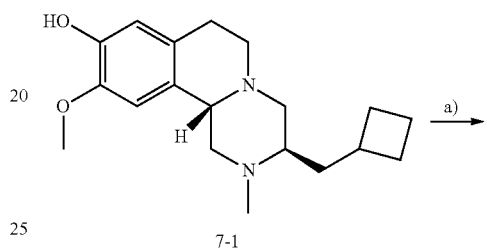

7-1

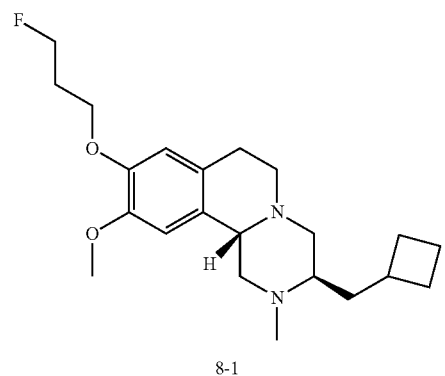

8-1

Synthesis of 8-1:

Product 7-1 (8.0 mg, 0.026 mmol) was dissolved in acetone (0.5 mL) and Cs$_2$CO$_3$ (25.0 mg, 0.078 mmol, 3 equiv.) was added followed by 1-bromo-3-fluoropropane (11 mg, 0.075 mmol, 3.0 equiv). The reaction mixture was heated to 50° C. for one hour. The crude mixture was filtered, diluted to 1 mL with MeOH, and submitted directly for preparative chromatography yielding (3R,11bS)-3-(cyclobutylmethyl)-9-(3-fluoropropoxy)-10-methoxy-2-methyl-1H,2H,3H,4H,6H,7H,11bH-piperazino[2,1-a]isoquinoline 8-1.

Table 8 below provides the observed (Obs) ion m/z ratio for 8-1 and other representative compounds that were made according to the procedure as described in this example.

TABLE 8

[Structure shown with R¹—O— substituent on piperazino[2,1-a]isoquinoline core with cyclobutylmethyl and N-methyl groups]

| Cpd. No. | —R¹ | Compound Name | Obs Ion (m/z) |
|---|---|---|---|
| 8-1 | —CH₂CH₂CH₂F | (3R,11bS)-3-(cyclobutylmethyl)-9-(3-fluoropropoxy)-10-methoxy-2-methyl-1H,2H,3H,4H,6H,7H,11bH-piperazino[2,1-a]isoquinoline | 377.10 |
| 8-2 | —CH₂CF₃ | (3R,11bS)-3-(cyclobutylmethyl)-10-methoxy-2-methyl-9-(2,2,2-trifluoroethoxy)-1H,2H,3H,4H,6H,7H,11bH-piperazino[2,1-a]isoquinoline | 399.1 |
| 8-3 | [CH₂-difluorocyclopropyl group] | (3R,11bS)-3-(cyclobutylmethyl)-9-[(2,2-difluorocyclopropyl)methoxy]-10-methoxy-2-methyl-1H,2H,3H,4H,6H,7H,11bH-piperazino[2,1-a]isoquinoline | 407.1 |
| 8-4 | —CH₂CH₂F | (3R,11bS)-3-(cyclobutylmethyl)-9-(2-fluoroethoxy)-10-methoxy-2-methyl-1H,2H,3H,4H,6H,7H,11bH-piperazino[2,1-a]isoquinoline | 363.1 |
| 8-5 | [CH₂-cyclopropyl group] | (3R,11bS)-3-(cyclobutylmethyl)-9-(cyclopropylmethoxy)-10-methoxy-2-methyl-1H,2H,3H,4H,6H,7H,11bH-piperazino[2,1-a]isoquinoline | 371.1 |
| 8-6 | [CH₂-cyclobutyl group] | (3R,11bS)-9-(cyclobutylmethoxy)-3-(cyclobutylmethyl)-10-methoxy-2-methyl-1H,2H,3H,4H,6H,7H,11bH-piperazino[2,1-a]isoquinoline | 385.1 |
| 8-7 | —CH₂CH₂CH₂CF₃ | (3R,11bS)-3-(cyclobutylmethyl)-10-methoxy-2-methyl-9-(4,4,4-trifluorobutoxy)-1H,2H,3H,4H,6H,7H,11bH-piperazino[2,1-a]isoquinoline | 427.1 |
| 8-8 | —CH₂CH₂CH₂CH₂F | (3R,11bS)-3-(cyclobutylmethyl)-9-(4-fluorobutoxy)-10-methoxy-2-methyl-1H,2H,3H,4H,6H,7H,11bH-piperazino[2,1-a]isoquinoline | 391.1 |

Example 9

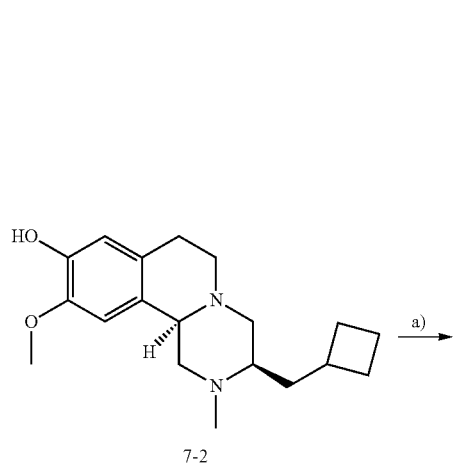

7-2 a)

-continued

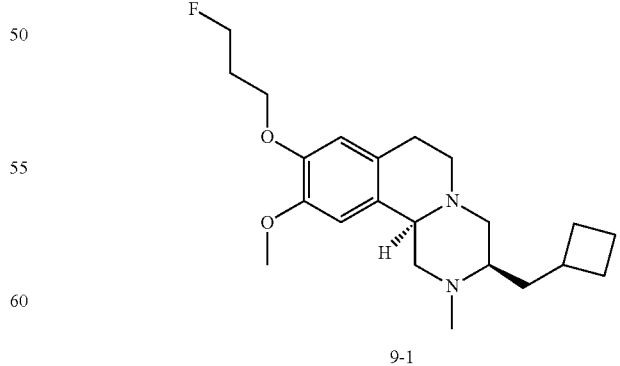

9-1

Synthesis of 9-1:
(3R,11bR)-3-(cyclobutylmethyl)-10-methoxy-2-methyl-1H,2H,3H,4H,6H,7H,11bH-piperazino[2,1-a]isoquinolin-9- ol 7-2 (8.0 mg, 0.026 mmol) was dissolved in acetone (0.5 mL) and Cs$_2$CO$_3$ (25.0 mg, 0.078 mmol, 3 equiv.) was added followed by 1-bromo-3-fluoropropane (11 mg, 0.075 mmol, 3.0 equiv). The reaction mixture was heated to 50° C. for one hour. The crude mixture was filtered, diluted to 1 mL with MeOH, and submitted directly for preparative chromatography yielding (3R,11bR)-3-(cyclobutylmethyl)-9-(3-fluoropropoxy)-10-methoxy-2-methyl-1H,2H,3H,4H,6H,7H,11bH-piperazino[2,1-a]isoquinoline 9-1 (observed ion m/z ratio 377.1).

Example 10

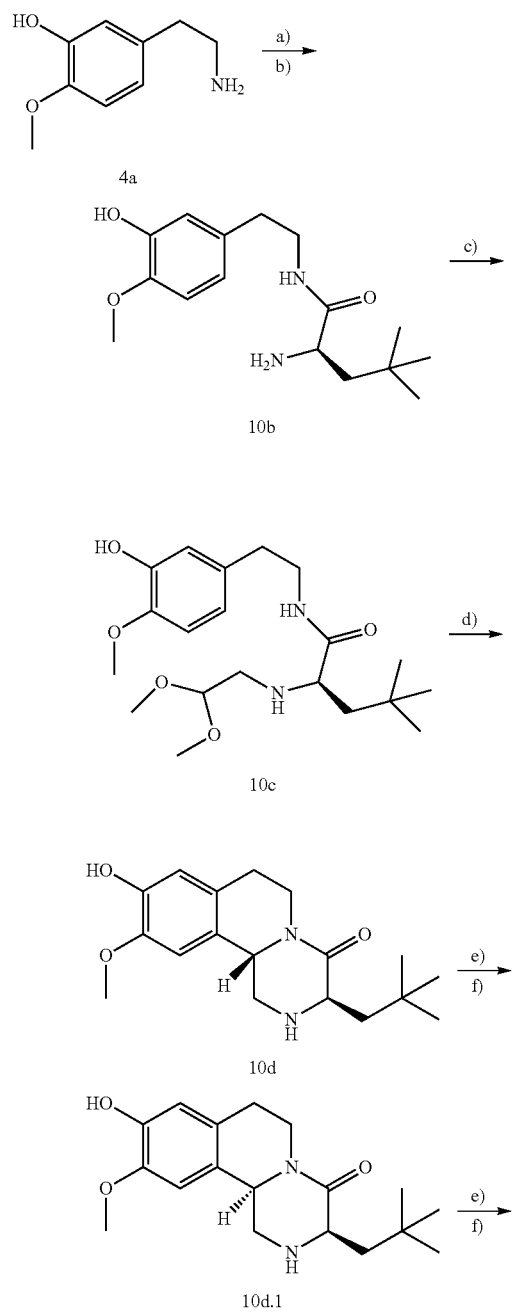

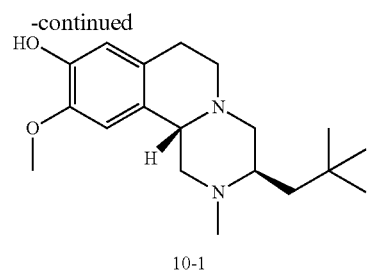

10-1

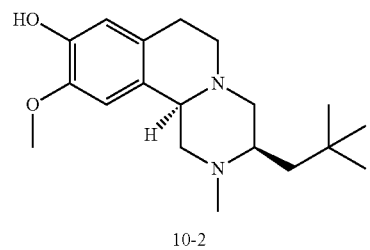

10-2

Synthesis of 10b:

(2R)-2-{[(tert-butoxy)carbonyl]amino}-4,4-dimethylpentanoic acid (0.77 g, 3.14 mmol, 1.0 eq,) and 5-(2-aminoethyl)-2-methoxyphenol hydrochloride (0.50 g, 2.99 mmol) were dissolved in methylene chloride (20 mL) and triethylamine (1.7 mL, 12 mmol, 4.0 eq) was added followed by HATU (1.4 g, 3.6 mmol, 1.2 eq). The reaction was stirred at room temperature overnight and then further diluted with methylene chloride and washed with sat. NH$_4$Cl followed by sat. NaHCO$_3$. The combined organic layers were dried over MgSO$_4$ and concentrated in vacuo. Silica gel column (24 g) was loaded using methylene chloride and run with an increasing gradient of EtOAc (0-100%) in hexanes over 20 min to provide tert-butyl (R)-(1-((3-hydroxy-4-methoxyphenethyl)amino)-4,4-dimethyl-1-oxopentan-2-yl)carbamate (1.2 g, 3.0 mmol) in quantitative yield. This product (1.2 g, 3.0 mmol) was dissolved in methylene chloride (20 mL) and trifluoroacetic acid (3 mL) was added. Once the reaction was complete, the mixture was concentrated and redissolved in methylene chloride (50 mL) and made basic with sat. NaHCO$_3$. The combined organic layers were dried over MgSO$_4$ and concentrated in vacuo to provide (2R)-2-amino-N—[2-(3-hydroxy-4-methoxyphenyl)ethyl]-4,4-dimethylpentanamide 10b (0.60 g, 2.04 mmol) as a yellow oil in 68% yield.

Synthesis of 10c:

Intermediate 10b (0.60 g, 2.04 mmol) was dissolved in methanol (10 mL) and 2,2-dimethoxyacetaldehyde (60 wt. % in water) (0.40 mL, 2.04 mmol, 1.0 eq) was added. Acetic acid was added until neutral then catalytic 10% palladium on carbon was added and the reaction mixture was purged with hydrogen and stirred overnight. The mixture was filtered through celite, and concentrated in vacuo. Silica gel column (24 g) was loaded using methylene chloride and run with an increasing gradient of methanol (0-10%) in methylene chloride over 20 min to provide (2R)-2-[(2,2-dimethoxyethyl)amino]-N—[2-(3-hydroxy-4-methoxyphenyl)ethyl]-4,4-dimethylpentanamide 10c as a yellow oil (0.79 g, 2.04 mmol) in a quantitative yield.

Synthesis of 10d and 10d.1:

Concentrated sulfuric acid (5 mL) was cooled to 0° C. and 10c (0.80 g, 2.1 mmol) dissolved in methanol (3 mL) was added dropwise. The reaction was warmed to room temp and stirred overnight. The reaction mixture was cooled by addition of ice then made just basic with 10% NaOH. The methanol was removed in vacuo and the compound was extracted with methylene chloride (3×50 mL). The combined organic layers were dried over MgSO$_4$ and concentrated in vacuo. Silica gel column (40 g) was loaded using methylene chloride and run with an increasing gradient of methanol (0-5%) in methylene chloride over 40 min to provide (3R,11bS)-3-(2,2-dimethylpropyl)-9-hydroxy-10-methoxy-1H,2H,3H,4H,6H,7H,11bH-piperazino[2,1-a]isoquinolin-4-one 10d (0.15 g, 0.47 mmol) and (3R,11bR)-3-(2,2-dimethylpropyl)-9-hydroxy-10-methoxy-1H,2H,3H, 4H,6H,7H,11bH-piperazino[2,1-a]isoquinolin-4-one 10d.1 (0.21 g, 0.65 mmol).

Synthesis of 10-1 and 10-2:

Intermediate 10d (0.15 g, 0.47 mmol) was dissolved in methylene chloride (5 mL) and triethylamine (0.08 mL, 0.56 mmol, 1.2 eq) added followed by di-tert-butyl dicarbonate (0.11 g, 0.51 mmol, 1.1 eq). The reaction stirred overnight then concentrated in vacuo. Silica gel column (12 g) was loaded using methylene chloride and run with an increasing gradient of ethyl acetate (0-70%) in hexanes over 15 min to provide tert-butyl (3R,11 bS)-3-(2,2-dimethylpropyl)-9-hydroxy-10-methoxy-4-oxo-1H,2H,3H,4H,6H,7H,11bH-piperazino[2,1-a]isoquinoline-2-carboxylate (0.14 g, 0.33 mmol) in 71% yield. This product (0.14 g, 0.33 mmol) was dissolved in anhydrous THF (5 mL) and 2M LAH (0.84 mL, 1.7 mmol, 5 eq) was added. The reaction mixture was stirred at room temperature for 2 hr then heated to 70° C. overnight. The mixture was quenched with water (1 mL) and diluted with EtOAc (20 mL). The product was extracted with EtOAc (3×25 mL) from Rochelle's salt (10 mL). The combined organic layers were dried over MgSO$_4$ and concentrated in vacuo to provide (3R,1 bS)-3-(2,2-dimethylpropyl)-10-methoxy-2-methyl-1H,2H,3H,4H,6H,7H,11bH-piperazino[2,1-a]isoquinolin-9-ol 10-1 (0.09 g, 0.3 mmol) in 90% yield.

(3R,11 bR)-3-(2,2-dimethylpropyl)-10-methoxy-2-methyl-1H,2H,3H,4H,6H,7H,11bH-piperazino[2,1-a]isoquinolin-9-ol 10-2 was also made using this procedure.

Example 11

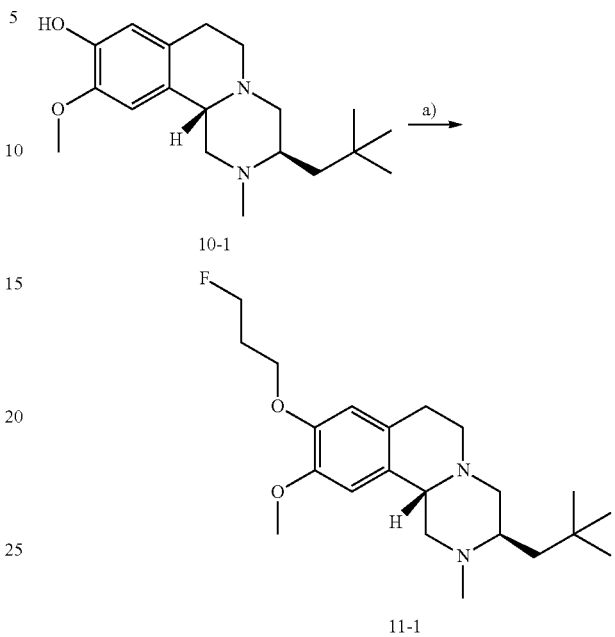

Synthesis of 11-1:

Product 10-1 (8.0 mg, 0.025 mmol) was dissolved in acetone (0.5 mL) and Cs$_2$CO$_3$ (21.0 mg, 0.063 mmol, 2.5 equiv.) was added followed by 1-bromo-3-fluoropropane (5.4 mg, 0.038 mmol, 1.5 equiv). The reaction mixture was heated to 50° C. for one hour. The crude mixture was filtered, diluted to 1 mL with MeOH, and submitted directly for preparative chromatography (3R,1bS)-3-(2,2-dimethylpropyl)-9-(3-fluoropropoxy)-10-methoxy-2-methyl-1H,2H,3H,4H,6H,7H,11bH-piperazino[2,1-a]isoquinoline 11-1.

Table 11 below provides the observed (Obs) ion m/z ratio for 11-1 and other representative compounds that were made according to the procedure as described in this example.

TABLE 11

| Cpd. No. | —R$^1$ | Compound Name | Obs Ion (m/z) |
|---|---|---|---|
| 11-1 | —CH$_2$CH$_2$CH$_2$F | (3R,11bS)-3-(2,2-dimethylpropyl)-9-(3-fluoropropoxy)-10-methoxy-2-methyl-1H,2H,3H,4H,6H,7H,11bH-piperazino[2,1-a]isoquinoline | 379.1 |
| 11-2 | —CH$_3$ | (3R,11bS)-3-(2,2-dimethylpropyl)-9,10-dimethoxy-2-methyl-1H,2H,3H,4H,6H,7H,11bH-piperazino[2,1-a]isoquinoline | 333.1 |

TABLE 11-continued

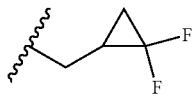

| Cpd. No. | —R¹ | Compound Name | Obs Ion (m/z) |
|---|---|---|---|
| 11-3 | —CH₂CF₃ | (3R,11bS)-3-(2,2-dimethylpropyl)-10-methoxy-2-methyl-9-(2,2,2-trifluoroethoxy)-1H,2H,3H,4H,6H,7H,11bH-piperazino[2,1-a]isoquinoline | 401.4 |
| 11-4 | 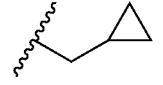 | (3R,11bS)-9-[(2,2-difluorocyclopropyl)methoxy]-3-(2,2-dimethylpropyl)-10-methoxy-2-methyl-1H,2H,3H,4H,6H,7H,11bH-piperazino[2,1-a]isoquinoline | 409.1 |
| 11-5 | —CH₂CH₂CF₃ | (3R,11bS)-3-(2,2-dimethylpropyl)-10-methoxy-2-methyl-9-(3,3,3-trifluoropropoxy)-1H,2H,3H,4H,6H,7H,11bH-piperazino[2,1-a]isoquinoline | 415.1 |
| 11-6 | —CH₂CH₂F | (3R,11bS)-3-(2,2-dimethylpropyl)-9-(2-fluoroethoxy)-10-methoxy-2-methyl-1H,2H,3H,4H,6H,7H,11bH-piperazino[2,1-a]isoquinoline | 365.1 |
| 11-7 | 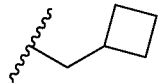 [SMILES: *CC1CCC1] | (3R,11bS)-9-(cyclopropylmethoxy)-3-(2,2-dimethylpropyl)-10-methoxy-2-methyl-1H,2H,3H,4H,6H,7H,11bH-piperazino[2,1-a]isoquinoline | 373.1 |
| 11-8 | | (3R,11bS)-9-(cyclobutylmethoxy)-3-(2,2-dimethylpropyl)-10-methoxy-2-methyl-1H,2H,3H,4H,6H,7H,11bH-piperazino[2,1-a]isoquinoline | 387.1 |
| 11-9 | —CH₂CH₂CH₂CF₃ | (3R,11bS)-3-(2,2-dimethylpropyl)-10-methoxy-2-methyl-9-(4,4,4-trifluorobutoxy)-1H,2H,3H,4H,6H,7H,11bH-piperazino[2,1-a]isoquinoline | 429.1 |
| 11-10 | —CH₂CH₂CH₂CH₂F | (3R,11bS)-3-(2,2-dimethylpropyl)-9-(4-fluorobutoxy)-10-methoxy-2-methyl-1H,2H,3H,4H,6H,7H,11bH-piperazino[2,1-a]isoquinoline | 393.1 |
| 11-11 | —CH₂CH₂OCH₃ | (3R,11bS)-3-(2,2-dimethylpropyl)-10-methoxy-9-(2-methoxyethoxy)-2-methyl-1H,2H,3H,4H,6H,7H,11bH-piperazino[2,1-a]isoquinoline | 377.1 |
| 11-12 | —CH₂CH₃ | (3R,11bS)-3-(2,2-dimethylpropyl)-9-ethoxy-10-methoxy-2-methyl-1H,2H,3H,4H,6H,7H,11bH-piperazino[2,1-a]isoquinoline | 347.1 |
| 11-13 | —CH(CH₃)₂ | (3R,11bS)-3-(2,2-dimethylpropyl)-10-methoxy-2-methyl-9-(propan-2-yloxy)-1H,2H,3H,4H,6H,7H,11bH-piperazino[2,1-a]isoquinoline | 361.1 |
| 11-14 | —CD₂CD₃ | (3R,11bS)-3-(2,2-dimethylpropyl)-9-(ethoxy-d₅)-10-methoxy-2-methyl-1H,2H,3H,4H,6H,7H,11bH-piperazino[2,1-a]isoquinoline | 352.1 |
| 11-15 | —CD₃ | (3R,11bS)-3-(2,2-dimethylpropyl)-9,10-bis(methoxy-d₃)-2-methyl-1H,2H,3H,4H,6H,7H,11bH-piperazino[2,1-a]isoquinoline | |

Additionally, Compounds 11-2 and 11-3 were prepared according to General Schemes 2 and 3, respectively.

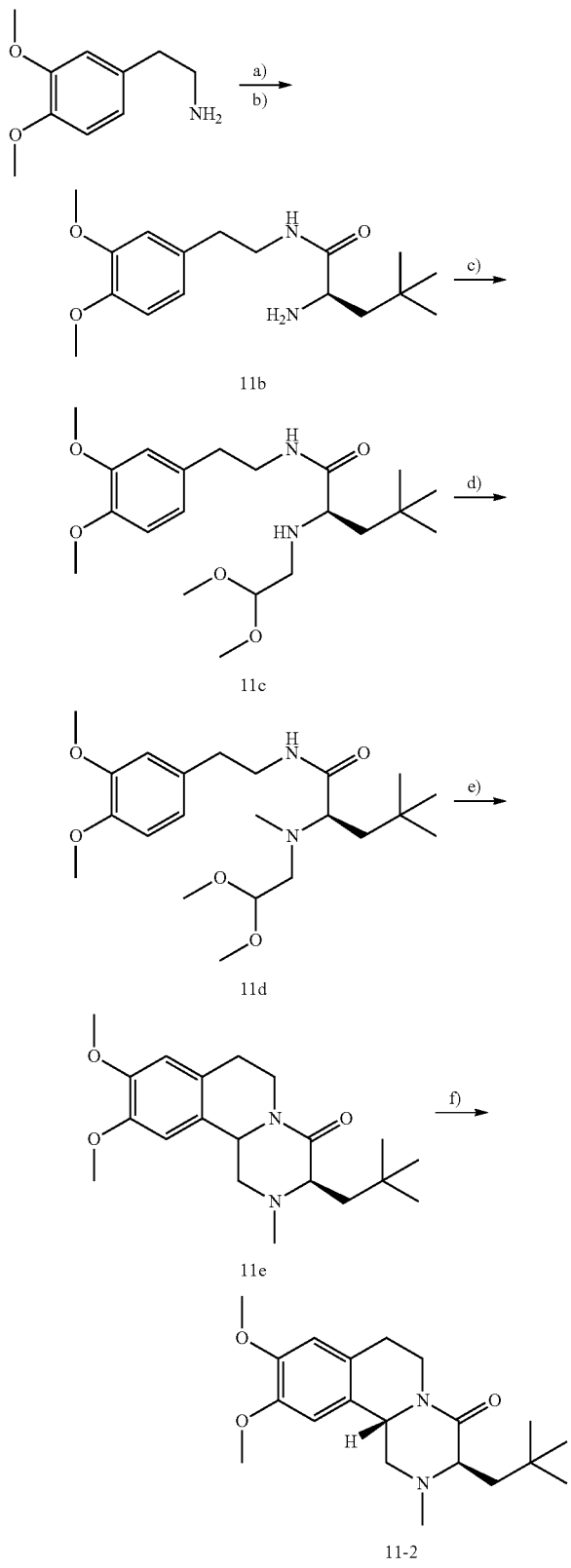

Synthesis of 11b:

2-(3,4-Dimethoxyphenyl)ethan-1-amine ([40 g, 221 mmol]) was dissolved in DCM ([400 mL]). The solution was cooled and (R)-2-((tert-butoxycarbonyl)amino)-4,4-dimethylpentanoic acid ([59.6 g, 243 mmol, 1.1 eq.]) was added. DMAP (7.3 g, 60 mmol, 0.27 eq.) was added, followed by EDAC (74.1 g, 386 mmol, 1.75 eq.) in portions, producing a heterogeneous mixture. The mixture was warmed to room temperature and stirred until completion. Upon completion the reaction was quenched with citric acid. The phases were separated and the aqueous phase was back-extracted with DCM. The pooled organics were washed with brine and distilled to provide tert-butyl (R)-(1-((3,4-dimethoxyphenethyl)amino)-4,4-dimethyl-1-oxopentan-2-yl)carbamate 11a. 11a (90 g, 221 mmol) was dissolved in DCM (315 mL). The solution was cooled prior to the addition of trifluoroacetic acid (135 mL). The reaction was warmed to room temperature and stirred until completion. Upon completion, the reaction was cooled, diluted with water and DCM before being quenched with sodium hydroxide. The phases were separated and the aqueous phase was back-extracted with DCM. The pooled organics were washed with brine and distilled into THF to provide (R)-2-amino-N-(3,4-dimethoxyphenethyl)-4,4-dimethylpentanamide 11b.

Synthesis of 11c:

11b (66 g, 214 mmol) was dissolved in THF (528 mL). Acetic acid (64.3 g, 1070 mmol, 5 eq.) and 2,2-Dimethoxyacetaldehyde, 60% in water, (39 g, 225 mmol, 1.05 eq.) were added and stirred at room temperature for 1 hour. The reaction was cooled prior to the portionwise addition of sodium cyanoborohydride (26.9 g, 428 mmol, 2 eq.). Upon completion, the reaction was diluted with water and quenched with sodium hydroxide. The THF was stripped and replaced with EtOAc. The phases were separated and the aqueous phase was back-extracted with EtOAc. The pooled organics are washed with brine and distilled into MeOH to provide (R)-2-((2,2-dimethoxyethyl)amino)-N-(3,4-dimethoxyphenethyl)-4,4-dimethylpentanamide 11c.

Synthesis of 11d:

11c (84.9 g, 214 mmol) was dissolved in MeOH (1.25 L). Paraformaldehyde (38.6 g, 1285 mmol, 6 eq.) and acetic acid (84.9 g, 1413 mmol, 6.6 eq.) were added. Sodium cyanoborohydride (33.6 g, 535 mmol, 2.5 eq.) was added in portions at room temperature. The reaction was slowly heated to control an exotherm. Upon completion, the reaction was diluted with water and quenched with sodium hydroxide. The MeOH was stripped and replaced with EtOAc. The phases were separated and the aqueous phase was back-extracted with EtOAc. The pooled organics were washed with brine and solvent exchanged into DCM to provide (R)-2-((2,2-dimethoxyethyl)(methyl)amino)-N-(3,4-dimethoxyphenethyl)-4,4-dimethylpentanamide 11d.

Synthesis of 11e Diastereomer Mix:

Concentrated sulfuric acid (11.9 g, 122 mmol, 5 eq.) was dissolved/suspended in DCM (50 mL) and cooled. 11d (10 g, 24.4 mmol) was dissolved in DCM (25 mL) and added rapidly to the acid solution with vigorous stirring. Upon completion, the reaction was diluted with water and quenched with ammonium hydroxide. The phases were separated and the aqueous phase was back-extracted with DCM. The pooled organics are washed with brine and solvent exchanged into THF to provide (3R)-9,10-dimethoxy-2-methyl-3-neopentyl-1,2,3,6,7,11b-hexahydro-4H-pyrazino[2,1-a]isoquinolin-4-one 11e.

Synthesis of 11-2 Diastereomer Mix:

11e (8.45 g, 24.4 mmol) was dissolved in anhydrous THF (101 mL) and cooled. Lithium aluminum hydride, 2M, (36.6 mL, 73.2 mmol, 3 eq.) was added and the reaction was heated. Upon completion, the LAH was quenched in the manner of Feiser. The precipitated aluminum salts were filtered and washed. The filtrate was stripped of THF and replaced with methyl-t-butyl ether. The phases were separated and the aqueous phase was back-extracted with MTBE. The pooled organics were washed with brine and solvent exchanged into MeOH to provide (3R)-3-(2,2-dimethylpropyl)-9,10-dimethoxy-2-methyl-1H,2H,3H,4H,6H,7H,11bH-piperazino[2,1-a]isoquinoline 11-2 diastereomer mix.

Synthesis of 11-2 Diphosphate:

11-2 diastereomer mix (20 g, 60.2 mmol) was dissolved in MeOH (160 mL). The solution was filtered and heated to 50° C. Phosphoric acid (7.25 g, 1.05 eq.) was added. Solution was heated to 60° C. and a second equivalent of phosphoric acid was added over 1 hour (7.25 g, 1.05 eq.) and stirred at 60° C. for 10 minutes before cooling to 20° C. over 4 hours. The suspension was filtered and the solids were washed with MeOH. Solids were dried in a vacuum oven for 3 days at 50° C. to provide 11-2, (3R,1bS)-9,10-dimethoxy-2-methyl-3-neopentyl-1,3,4,6,7,11b-hexahydro-2H-pyrazino[2,1-a]isoquinoline, also known as (3R,11bS)-3-(2,2-dimethylpropyl)-9,10-dimethoxy-2-methyl-1H,2,3H,34H,6H,7H,1 bH-piperazino[2,1-a]isoquinoline, as the diphosphate salt.

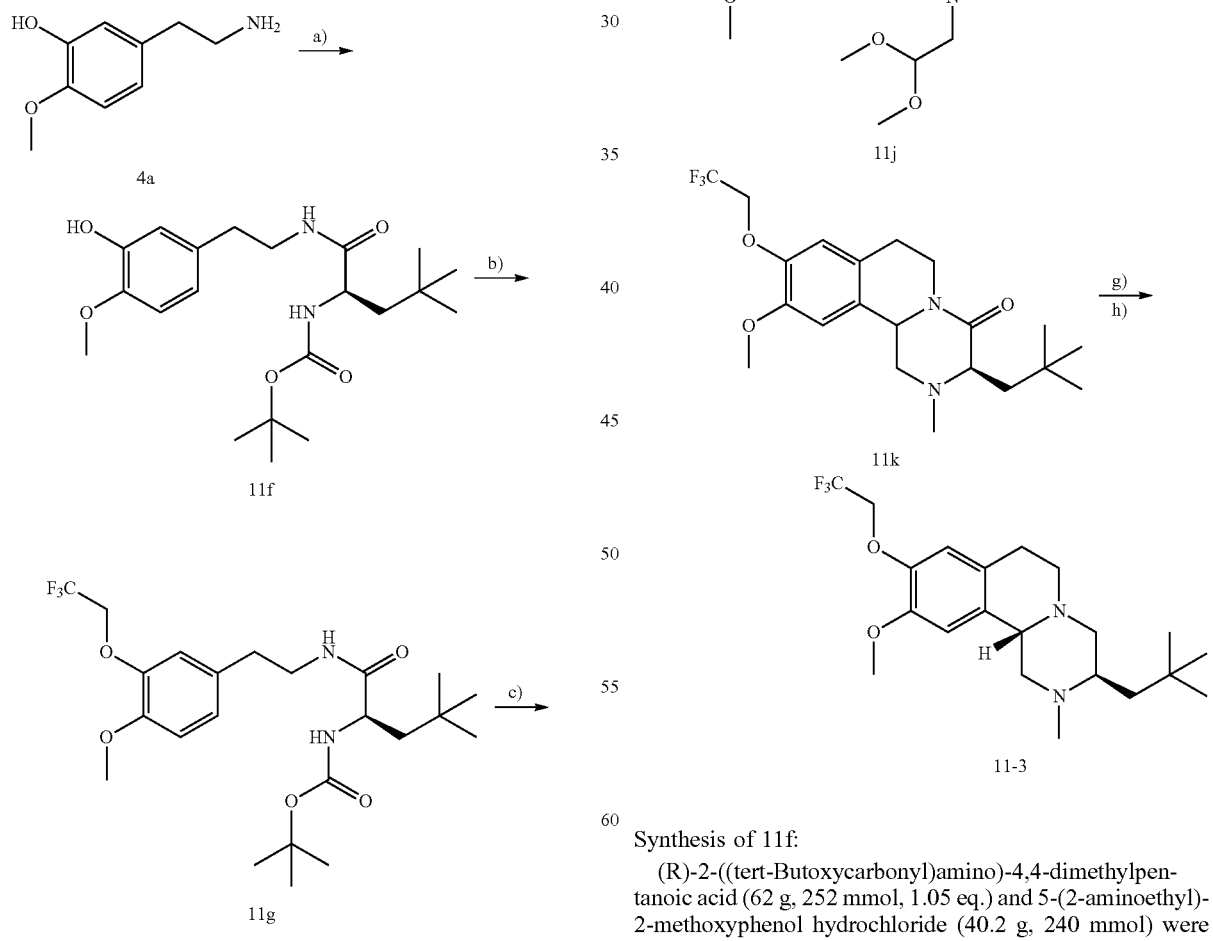
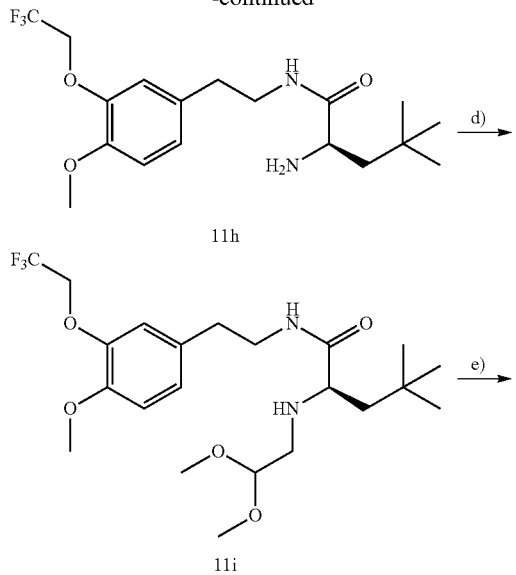
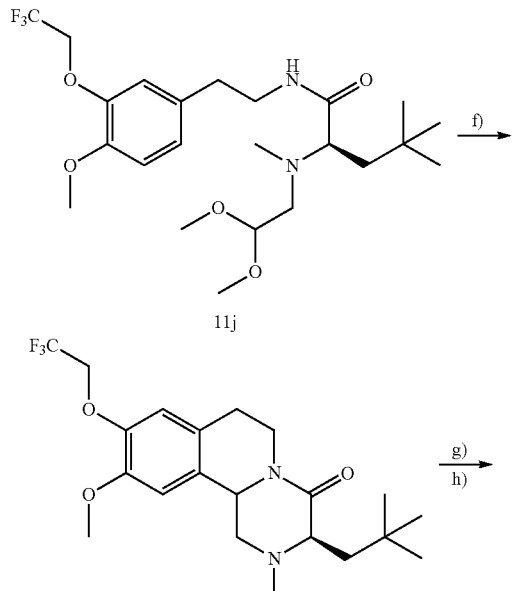
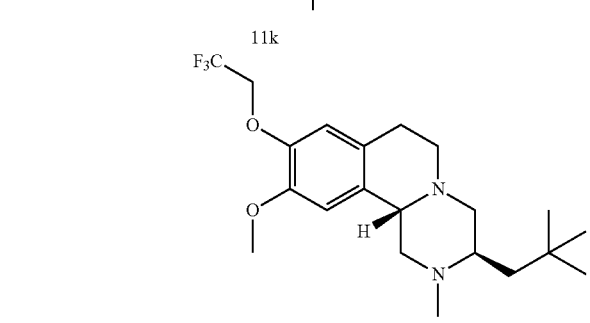

Synthesis of 11f:

(R)-2-((tert-Butoxycarbonyl)amino)-4,4-dimethylpentanoic acid (62 g, 252 mmol, 1.05 eq.) and 5-(2-aminoethyl)-2-methoxyphenol hydrochloride (40.2 g, 240 mmol) were dissolved in DMF (400 mL) and the mixture was cooled to 0° C. HATU (96 g, 252 mmol, 1.05 eq.) was added followed by addition of DIEA (93.2 g, 721 mmol, 3.0 eq.) over 10 minutes. The mixture was stirred at 0° C. for 60 minutes and then added to water (1000 mL) and EtOAc (1000 mL). The mixture was transferred to a separation funnel, separated and the aqueous extracted with EtOAc. The pooled organics were washed with brine and water and then dried over MgSO$_4$ and concentrated in vacuo to provide tert-butyl (R)-(1-((3-hydroxy-4-methoxyphenethyl)amino)-4,4-dimethyl-1-oxopentan-2-yl)carbamate 1 f as a viscous oil.

Synthesis of 11 g:

Compound 1f (90 g, 228 mmol) and K$_2$CO$_3$ (94.5 g, 684 mmol, 3.0 eq.) were dissolved in acetone (630 mL) and 2,2,2-trifluoroethyl triflate (79.4 g, 342 mmol, 1.5 eq.) was slowly added. The reaction was warmed to 50° C. and stirred for 5 hours. After cooling to room temperature, the mixture was diluted with water (450 mL). The mixture was concentrated to remove the acetone and EtOAc (450 mL) was added. The phases were separated and the aqueous layer was extracted with EtOAc. The pooled organics were washed with brine and water and then dried over MgSO$_4$ and concentrated in vacuo to provide tert-butyl (R)-(1-((4-methoxy-3-(2,2,2-trifluoroethoxy)phenethyl)amino)-4,4-dimethyl-1-oxopentan-2-yl)carbamate 11 g as a viscous oil.

Synthesis of 11h:

Compound 11g (96.5 g, 203 mmol) was dissolved in DCM (290 mL) and cooled to 0° C. followed by addition of TFA (193 mL). The mixture was stirred for 10 minutes and then warmed to room temperature and stirred for 6 hours. The reaction was then cooled to 0° C. and diluted with water and DCM. A 50% w/w NaOH solution was added under vigorous stirring until a pH of 13 was reached. The layers were separated and the organic was washed with brine and concentrated in vacuo to provide (R)-2-amino-N-(4-methoxy-3-(2,2,2-trifluoroethoxy)phenethyl)-4,4-dimethylpentanamide 11h as a viscous oil.

Synthesis of 11i:

Compound 11h (5.0 g, 13.3 mmol) was dissolved in MTBE (35 mL) and the reaction mixture was purged with nitrogen and cooled to 0° C. Acetic acid (4.0 g, 66.4 mmol, 5.0 eq.) was added at and maintained at 0° C. 2,2-Dimethoxyacetaldehyde, 60% in water, (4.61 g, 26.6 mmol, 2.0 eq.) was added and the reaction mixture was purged with nitrogen. The reaction was stirred for 90 minutes at 0° C. NaBH$_4$ (1.0 g, 26.6 mmol, 2.0 eq.) was added portion-wise over 10 minutes and then the reaction mixture stirred at 0° C. for 60 minutes. Water (25 mL) was added. A 4M solution of K$_2$CO$_3$ was added until a pH of 11 was reached. The layers were separated. The organic was washed with brine and concentrated in vacuo to provide (R)-2-((2,2-dimethoxyethyl)amino)-N-(4-methoxy-3-(2,2,2-trifluoroethoxy)phenethyl)-4,4-dimethylpentanamide 11i.

Synthesis of 11j:

Compound 11i (6.2 g, 13.3 mmol) was dissolved in MTBE (18 mL) and and EtOH (9 mL), purged with nitrogen, and cooled to 0° C. Acetic acid (4.0 g, 66.4 mmol, 5.0 eq.) and formalin (5.4 g, 66.4 mmol, 5.0 eq.) were added and stirred for 90 minutes at 0° C. Na(AcO)$_3$BH (8.5 g, 40.0 mmol, 3.0 eq.) was added portion-wise over 5 minutes and stirred at 0° C. for 30 minutes. At 0° C., water (25 mL) was added, followed by a 4M solution of K$_2$CO$_3$ until a pH of 11. The layers were separated. The organic was washed with brine and concentrated in vacuo to provide (R)-2-((2,2-dimethoxyethyl)(methyl)amino)-N-(4-methoxy-3-(2,2,2-trifluoroethoxy)phenethyl)-4,4-dimethylpentanamide 11j.

Synthesis of 11k:

Compound 11j (22.9 g, 49.3 mmol) was dissolved in DCM (57 mL) and added over 2 minutes to −30° C. solution of H$_2$SO$_4$ (24.2 g, 247 mmol, 5.0 eq.) in DCM (115 mL). The reaction mixture warmed to 0° C. during the addition and then stirred for 30 minutes. At 0° C., water (69 mL) was added then NH$_4$OH was added under vigorous stirring until a pH of 10 was reached. The phases were separated and the organic layer was washed with brine and then dried over MgSO$_4$ and concentrated in vacuo to provide (3R)-10-methoxy-2-methyl-3-neopentyl-9-(2,2,2-trifluoroethoxy)-1,2,3,6,7,11b-hexahydro-4H-pyrazino[2,1-a]isoquinolin-4-one 11k.

Synthesis of 11-3 Diastereomer Mix:

Compound 11k (12.5 g, 30.2 mmol) was dissolved in 2-methyltetrahydrofuran (87.5 mL) and 9-BBN (14.7 g, 2 eq. of the dimer solid) was added portion-wise. The reaction mixture was heated to 50° C. for 2 hours. The reaction mixture was then cooled to room temperature and heptane (87.5 mL) and HCl (1N, 62.5 mL) were added to reach a pH of about 2. The reaction mixture was stirred for 60 minutes and the phases were separated. The organic phase was washed with 37.5 mL of 1N HCl. The combined aqueous phases were charged with MTBE (62.5 mL) and 2M K$_2$CO$_3$ (62.5 mL) to reach a pH of 9-10. The mixture was stirred for 30 minutes and the phases were separated. The aqueous layer was washed with MTBE (62.5 mL). The pooled organics were washed with brine and concentrated in vacuo to provide 11-3 and its diastereomer as a mixture.

Synthesis of 11-3 L-DBTA Salt:

The diastereomer mixture containing 11-3 (5.12 g, 12.8 mmol) was dissolved in acetonitrile (30 mL) and dibenzoyl-L-tartaric acid (L-DBTA, 4.59 g, 1.0 eq.) was added. The reaction mixture was heated to 50° C. Water (12.5 mL) was added maintaining the temperature at 40-50° C. The mixture was cooled to room temperature over 3 hours. The mixture was filtered and then washed with 6:2.5 acetonitrile:water to provide an L-DBTA salt of (3R,11 bS)-10-methoxy-2-methyl-3-neopentyl-9-(2,2,2-trifluoroethoxy)-1,3,4,6,7,11 b-hexahydro-2H-pyrazino[2,1-a]isoquinoline 11-3 L-DBTA salt.

Synthesis of 11-3 and 11-3 di-HCl Salt:

L-DBTA salt of (3R,1bS)-10-methoxy-2-methyl-3-neopentyl-9-(2,2,2-trifluoroethoxy)-1,3,4,6,7,11 b-hexahydro-2H-pyrazino[2,1-a]isoquinoline 11-3 L-DBTA salt (30.0 g, 39.5 mmol) was suspended in water (300 mL) and isopropyl acetate (300 mL). NaOH was added (50% aqueous solution) until the pH was 13. Phases were separated and the organic washed with brine (90 mL). The organic layer was concentrated resulting in 15.9 g of 11-3 as the free base which was dissolved in ethyl acetate (80 mL). The solution was filtered and water was added (6.4 mL). The solution was heated to 35° C. and 37% HCl (3.4 mL, 1.05 eq.), was added over 5 minutes. A second charge of HCl (3.4 mL, 1.05 eq.) was added over 5 min. The mixture was cooled to 30° C. and seeded. The slurry was stirred for 90 minutes before being slowly cooled to room temperature. Solids were filtered and washed with ethyl acetate (16 mL). Wet cake was dried in vacuum oven at 50° C. to provide (3R,11bS)-10-methoxy-2-methyl-3-neopentyl-9-(2,2,2-trifluoroethoxy)-1,3,4,6,7,11 b-hexahydro-2H-pyrazino[2,1-a]isoquinoline as the dihydrochloride salt 11-3 di-HCl salt.

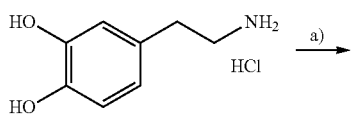

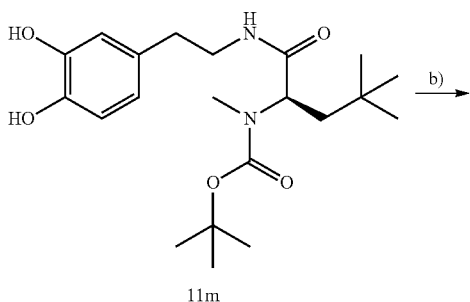

11m

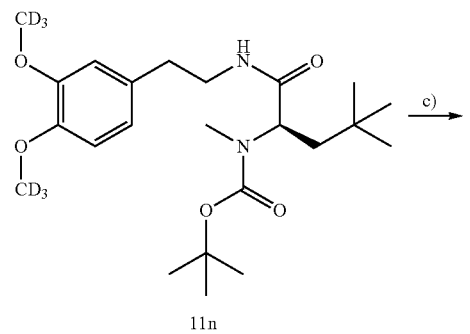

11n

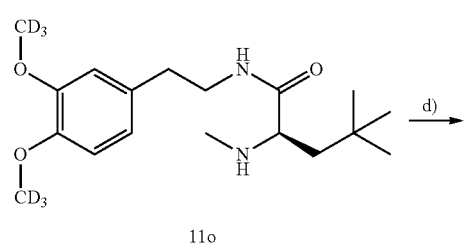

11o

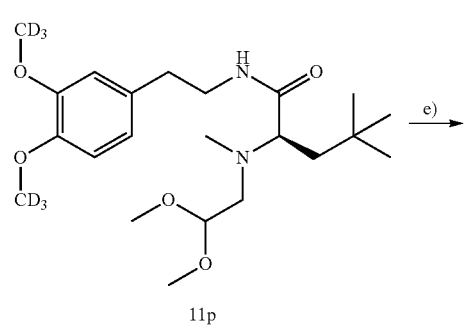

11p

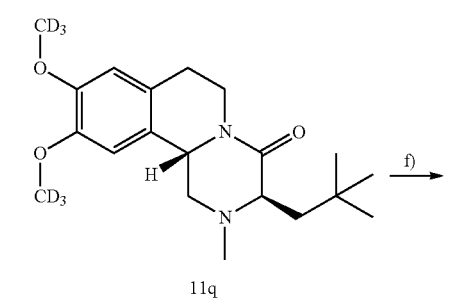

11q

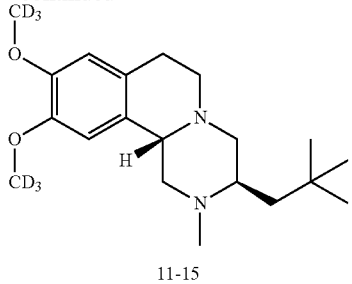

11-15

Synthesis of 11m:

Dopamine hydrochloride (15 g, 79.1 mmol) and 2-[[(1,1-dimethylethoxy)carbonyl]methylamino]-4,4-dimethyl-(2R)-pentanoic acid (21.5 g, 83.1 mmol, 1.05 eq.) were dissolved in DMF (150 mL) and cooled to 0° C. HATU (31.6 g, 83.1 mmol, 1.05 eq.) was added followed by addition of DIEA (30.7 g, 237 mmol, 3.0 eq.). The mixture was stirred at 0° C. for 2 hours and then added to water (300 mL) and EtOAc (300 mL). The mixture was transferred to a separation funnel, separated and the aqueous extracted with EtOAc. The pooled organics were washed with brine and water and concentrated in vacuo to provide tert-butyl (R)-(1-((3,4-dihydroxyphenethyl)amino)-4,4-dimethyl-1-oxopentan-2-yl)(methyl)carbamate 11m as a viscous oil.

Synthesis of 11n:

Compound 11m (31.2 g, 79.1 mmol) was dissolved in acetone (218 mL). $K_2CO_3$ (32.8 g, 237 mmol, 3.0 eq.) was added followed by iodomethane-$d_3$ (25.2 g, 174 mmol, 2.2 eq.). The reaction was warmed to 50° C. and stirred for 26 hours. After cooling to room temperature, the mixture was diluted with water (220 mL). The mixture was concentrated to remove acetone. EtOAc (156 mL) was added. The phases were separated and the aqueous layer was extracted with EtOAc. The pooled organics were washed with brine, dried over $MgSO_4$ and concentrated in vacuo to provide tert-butyl (R)-(1-((3,4-bis(methoxy-$d_3$)phenethyl)amino)-4,4-dimethyl-1-oxopentan-2-yl)(methyl)carbamate 11n as a viscous oil.

Synthesis of 11o:

Compound 1n (17.0 g, 39.7 mmol) was dissolved in DCM (60 mL) and cooled to 0° C. followed by addition of TFA (34 mL). The mixture was stirred for 10 minutes and then warmed to room temperature and stirred for 21 hours. The reaction was then cooled to 0° C. and diluted with water and DCM. A 50% w/w NaOH solution was added under vigorous stirring until a pH of 13 was reached. The layers were separated and the aqueous layer was extracted with DCM. The pooled organics were washed with brine and concentrated in vacuo to provide (R)—N-(3,4-bis(methoxy-$d_3$)phenethyl)-4,4-dimethyl-2-(methylamino)pentanamide 11o as a viscous oil.

Synthesis of 11p:

11o (13.0 g, 39.6 mmol) was dissolved in THF (104 mL). Acetic acid (11.4 mL, 200 mmol, 5 eq.) and 2,2-Dimethoxyacetaldehyde, 60% in water, (10.3 g, 59.4 mmol, 1.5 eq.) were added and stirred at room temperature for 2 hours. The reaction was cooled prior to the portionwise addition of sodium cyanoborohydride (5.2 g, 83.4 mmol, 2 eq.). Two more concurrent additions of 2,2-Dimethoxyacetaldehyde and sodium cyanoborohydride (0.4 eq. and 0.3 eq.) was required for completion of the reaction. Upon completion, the reaction was cooled to 0° C., diluted with water and quenched with 10% sodium hydroxide till a pH>10. The THF was stripped and replaced with EtOAc. The phases were separated and the aqueous phase was back-extracted with EtOAc. The pooled organics were washed with brine and concentrated in vacuo to provide (R)—N-(3,4-bis(methoxy-d$_3$)phenethyl)-2-((2,2-dimethoxyethyl)(methyl)amino)-4,4-dimethylpentanamide 11p.

Synthesis of 11q:

Concentrated sulfuric acid (10.6 mL, 199 mmol, 5 eq.) was dissolved/suspended in DCM (83 mL) and cooled to −20° C. 11p (16.5 g, 39.6 mmol) was dissolved in DCM (41 mL) and added rapidly to the acid solution with vigorous stirring keeping the reaction less than 0° C. Upon completion, the reaction was diluted with water (50 mL) and quenched with ammonium hydroxide to pH 9. The phases were separated and the aqueous phase was back-extracted with DCM. The pooled organics are washed with brine and concentrated in vacuo to provide a mix of diastereomers. Separation of the diastereomers was accomplished with normal phase silica column chromatography with hexane and ethyl acetate elution to provide (3R,1 b S)-9,10-bis(methoxy-d$_3$)-2-methyl-3-neopentyl-1,2,3,6,7,11 b-hexahydro-4H-pyrazino[2,1-a]isoquinolin-4-one 11q.

Synthesis of 11-15:

11q (6.9 g, 19.6 mmol) was dissolved in anhydrous THF (103 mL) and cooled to 0° C. Lithium aluminum hydride, 2.4M, (32.5 mL, 78 mmol, 4 eq.) was slowly added and the reaction was heated to 40° C. over 2 hours. Upon completion, the LAH was quenched in the manner of Feiser. The precipitated aluminum salts were filtered and washed with THF. The filtrate was stripped of THF and replaced with methyl-t-butyl ether. The phases were separated and the aqueous phase was back-extracted with MTBE. The pooled organics were washed with brine and concentrated in vacuo to provide (3R,11bS)-3-(2,2-dimethylpropyl)-9,10-bis(methoxy-d$_3$)-2-methyl-1H,2H,3H,4H,6H,7H,11bH-piperazino[2,1-a]isoquinoline also known as (3R,1bS)-9,10-bis(methoxy-d$_3$)-2-methyl-3-neopentyl-1,3,4,6,7,11b-hexahydro-2H-pyrazino[2,1-a]isoquinoline 11-15.

Example 12

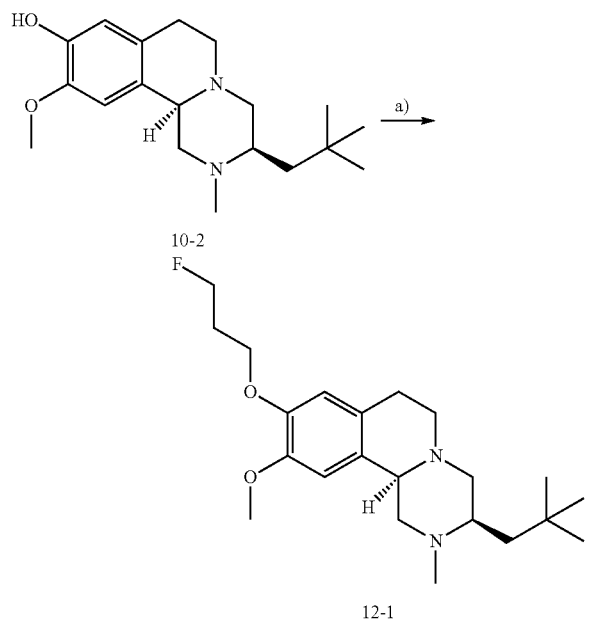

Synthesis of 12-1:

Product 10-2 (8.0 mg, 0.025 mmol) was dissolved in acetone (0.5 mL) and Cs$_2$CO$_3$ (21.0 mg, 0.063 mmol, 2.5 equiv.) was added followed by 1-bromo-3-fluoropropane (5.4 mg, 0.038 mmol, 1.5 equiv). The reaction mixture was heated to 50° C. for one hour. The crude mixture was filtered, diluted to 1 mL with MeOH, and submitted directly for preparative chromatography yielding (3R,11bR)-3-(2,2-dimethylpropyl)-9-(3-fluoropropoxy)-10-methoxy-2-methyl-1H,2H,3H,4H,6H,7H,11bH-piperazino[2,1-a]isoquinoline 12-1.

Table 12 below provides the observed (Obs) ion m/z ratio for 12-1 and other representative compounds that were made according to the procedure as described in this example.

TABLE 12

| Cpd. No. | —R$^1$ | Compound Name | Obs Ion (m/z) |
| --- | --- | --- | --- |
| 12-1 | —CH$_2$CH$_2$CH$_2$F | (3R,11bR)-3-(2,2-dimethylpropyl)-9-(3-fluoropropoxy)-10-methoxy-2-methyl-1H,2H,3H,4H,6H,7H,11bH-piperazino[2,1-a]isoquinoline | 379.1 |
| 12-2 | —CH$_3$ | (3R,11bR)-3-(2,2-dimethylpropyl)-9,10-dimethoxy-2-methyl-1H,2H,3H,4H,6H,7H,11bH-piperazino[2,1-a]isoquinoline | 333.1 |

Example 13

Vmat2 Inhibitor-Induced Reduction of Locomotor Activity

The effect of Vmat2 inhibitors on dopamine depletion is measured using the locomotor activity (LMA) assay. Following a pre-treatment time 60 minutes, male Sprague-Dawley rats (200-250 g) are placed in a clear cage surrounded by photocell detectors (San Diego Instruments). Rat locomotor activity is detected by breaks in the photocell beams and activity is defined as the number of beam breaks in 30 min. Data is analyzed by one-way analysis of variance (ANOVA; SigmaStat version 3.0.1, SPSS, Chicago, Ill.) followed by the Student Newman Keuls post-hoc test for significance.

Example 14

Conditioned Avoidance Response Assay of Antipsychotic Activity

The conditioned avoidance response (CAR) test has been shown to be an effective and reliable preclinical model for assessing the antipsychotic activity of compounds. In the CAR paradigm, a rat is trained in a two chamber shuttle box to respond to a conditioned stimulus (auditory) by negative reinforcement. If the animal fails to move to the other chamber upon presentation of an auditory stimulus, a mild foot shock is applied to the side where the rat is located. The rat learns to avoid the mild foot shock by moving to the other chamber upon initiation of the auditory signal, termed a conditioned avoidance response. Crossing to the other chamber during administration of the shock is termed an escape response. If a rat fails to move to the other chamber even upon administration of the foot shock, the rat is considered to have an escape failure. Numerous studies have shown that typical and atypical antipsychotic drugs selectively suppress CAR, thus making it an ideal assay to screen potential antipsychotic compounds (see, e.g., Wadenberg et al., *Biobehav. Rev.* (1999) 23: 851-62).

Male Wistar rats are trained every day for 3 to 4 weeks. In the training session, rats are placed in the CAR two-way shuttle box and the training period of 20 trials ensued. A trial consisted of a 10-sec presentation of an 80 dB white noise followed by a scrambled 0.6 mA foot shock lasting up to 20 sec. The inter-trial interval ranged from 20-60 sec. The rat learn to avoid shock by moving from one compartment to the other when the conditioned stimulus is presented (a conditioned avoidance response). A rat is deemed sufficiently trained if it avoided the shock when presented with the conditioned stimulus at least 19 times out of the 20 trials. Rats that do not pass these criteria are not used.

On test day, trained animals are acclimated in the test room for 30 minutes prior to testing. They were then dosed with compound and are placed in the CAR two-way shuttle box. In the test, 20 trials are performed on each rat. In each trial the conditioned stimulus is applied (10-sec presentation of 80 dB white noise), followed by the foot shock (a scrambled 0.6 mA foot shock lasting up to 20 sec). If the animal moves to the other chamber on presentation of the conditioned stimulus, it is scored as a conditioned avoidance response. If it moved upon presentation of the foot shock, it is scored as an escape. If it fails to move upon presentation of the foot shock, it is scored as an escape failure. Antipsychotic efficacy is evident by an increase in the number of escapes. Data are analyzed by analysis of variance (ANOVA) followed by post-hoc comparisons with the Bonferroni Test when appropriate. An effect is considered significant if $p<0.05$. Outliers defined as two standard deviations above or below the mean are detected and are removed from all analysis.

Example 15

Methods for Determining Vmat2 Inhibitory Activity of a Compound

Examples of techniques for determining the capability of a compound to inhibit VMAT2 are provided below. The procedure is adapted from that described previously (see, e.g., Near, (1986), *Mol. Pharmacol.* 30: 252-57; Teng, et al., *J. Neurochem.* 71, 258-65, 1998). Homogenates from human platelets or Sprague-Dawley rat forebrain were prepared by homogenization and then washed by centrifugation as described previously (see, e.g., Hoare et al., (2003) *Peptides* 24:1881-97). In a total volume of 0.2 mL in low-binding 96-well plates (Corning #3605), twelve concentrations of test compound were competed against 6 nM $^3$H-dihydrotetrabenezine (American Radiolabeled Chemicals, Kd 2.6 nM) on rat forebrain homogenate (100 µg membrane protein per well) or human platelet homogenate (50 µg membrane protein per well) in VMAT2 binding buffer (Dulbecco's phosphate buffered saline, 1 mM EDTA, pH 7.4). Following incubation at 25° C. for two hours, bound radioligand was collected by rapid filtration onto GF/B glass fiber filters using a Unifilter-96 Harvester (PerkinElmer). Filter plates were pre-treated for 10 minutes with 0.1% polyethylenimine, and following harvesting the filter plates were washed with 800 µl VMAT2 binding buffer. Bound radioligand was quantified by scintillation counting using a Topcount NXT (PerkinElmer).

The human Ki's for the compounds listed in Table 15-1 were determined using a slightly modified procedure shown below (see data in column under the heading "Ki nM"). In a total volume of 0.15 mL in low-binding 96-well plates (Corning #3605), twelve concentrations of test compound were competed against 10 nM $^3$H-dihydrotetrabenezine (American Radiolabeled Chemicals, Kd 2.6 nM) on rat forebrain homogenate (100 µg membrane protein per well) or human platelet homogenate (15 µg membrane protein per well) in VMAT2 binding buffer (Dulbecco's phosphate buffered saline, 1 mM EDTA, pH 7.4). Following incubation at 25° C. for 90 minutes, bound radioligand was collected by rapid filtration onto GF/B glass fiber filters using a Unifilter-96 Harvester (PerkinElmer). Filter plates were pre-treated with 0.1% polyethylenimine and allowed to dry overnight, and following harvesting the filter plates were washed with 800 µl VMAT2 binding buffer. Bound radioligand was quantified by scintillation counting using a Topcount NXT (PerkinElmer). In Table 15-1, compounds having a $K_i$ of less than 10 nM are identified as "+++", compounds having a $K_i$ of from 10 nM to 500 nM are identified as "++", and compounds having a $K_i$ greater than 500 nM are identified as "+" (NT=not tested).

TABLE 15-1

| Cpd. No. | VMAT2 $K_i$ |
|---|---|
| 2-1 | ++ |
| 2-2 | ++ |
| 2-3 | + |
| 2-4 | NT |
| 3-1 | + |
| 3-2 | + |
| 3-3 | + |
| 5-1 | +++ |
| 5-2 | ++ |
| 5-3 | ++ |
| 5-4 | ++ |
| 5-5 | ++ |
| 5-6 | +++ |
| 5-7 | +++ |
| 5-8 | +++ |
| 5-9 | +++ |
| 5-10 | ++ |
| 5-11 | +++ |
| 5-12 | ++ |
| 5-13 | +++ |
| 5-14 | +++ |
| 5-15 | +++ |
| 5-16 | +++ |
| 5-17 | +++ |
| 5-18 | +++ |
| 5-19 | +++ |
| 6-1 | + |
| 6-2 | + |
| 6-3 | + |
| 6-4 | + |
| 8-1 | ++ |
| 8-2 | +++ |
| 8-3 | ++ |
| 8-4 | ++ |
| 8-5 | ++ |
| 8-6 | +++ |
| 8-7 | ++ |
| 8-8 | ++ |
| 9-1 | + |
| 11-1 | +++ |
| 11-2 | +++ |

TABLE 15-1-continued

| Cpd. No. | VMAT2 $K_i$ |
|---|---|
| 11-3 | +++ |
| 11-4 | +++ |
| 11-5 | +++ |
| 11-6 | +++ |
| 11-7 | +++ |
| 11-8 | +++ |
| 11-9 | +++ |
| 11-10 | +++ |
| 11-11 | ++ |
| 11-12 | +++ |
| 11-13 | +++ |
| 11-14 | +++ |
| 11-15 | NT |
| 12-1 | ++ |
| 12-2 | + |

Another technique that may be routinely performed to determine the capability of a compound to inhibit VMAT2 is provided below. The following procedure is adapted from a previously described method (see Teng, et al., *J. Neurochem.* 71, 258-65, 1998).

Preparation of rat striatal vesicles: Rat *striata* from three rats are pooled and homogenized in 0.32 M sucrose. The homogenate is then centrifuged at 2,000×g for 10 min at 4° C. and the resulting supernatant is centrifuged at 10,000×g for 30 min at 4° C. The resulting pellet containing the enriched synaptosomal fraction (2 mL) is subjected to osmotic shock by addition of 7 mL of distilled $H_2O$, and subsequently the suspension is homogenized. The osmolarity is restored by the addition of 0.9 mL of 0.25 M HEPES and 0.9 mL of 1.0 M neutral L-(+)-tartaric acid dipotassium salt buffer (pH 7.5), followed by a 20 min centrifugation (20,000×g at 4° C.). The supernatant is then centrifuged for 60 min (55,000×g at 4° C.) and the resulting supernatant is centrifuged for 45 min (100,000×g at 4° C.). The resulting pellet is resuspended in 25 mM HEPES, 100 mM L-(+)-tartaric acid dipotassium salt, 5 mM $MgCl_2$, 10 mM NaCl, 0.05 mM EGTA, pH 7.5 to a protein concentration of 1-2 mg/mL and stored at −80° C. for up to 3 weeks without appreciable loss of binding activity. Immediately before use, the final pellet is resuspended in binding buffer (25 mM HEPES, 100 mM L-(+)-tartaric acid dipotassium salt, 5 mM $MgCl_2$, 10 mM NaCl, 0.05 mM EGTA, 0.1 mM EDTA, 1.7 mM ascorbic acid, pH 7.4).

[$^3$H]-dihydrotetrabenazine (DHTBZ) Binding: Aliquots of the vesicle suspension (0.16 mL, 15 μg of protein/mL) are incubated with competitor compounds (ranging from $10^{-6}$ to $10^{-12}$ M) and 2 nM [$^3$H]-dihydrotetrabenazine (HTBZ; specific activity: 20 Ci/mmol, American Radiolabeled Chemicals, Inc.) for 1 h at room temperature in a total volume of 0.5 mL. The reaction is terminated by rapid filtration of the samples onto Whatman GF/F filters using a Brandel cell harvester. Nonspecific binding is determined using 20 μM tetrabenazine (TBZ). Filters are previously soaked for 2 h with ice-cold polyethyleneimine (0.5%). After the filters are washed three times with the ice-cold buffer, they are placed into scintillation vials with 10 mL scintillation cocktail. Bound radioactivity is determined by scintillation spectrometry.

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference in their entirety. This application also claims the benefit of U.S. Provisional Patent Application No. 62/487,413, filed Apr. 19, 2017 and U.S. Provisional Patent Application No. 62/652,837, filed Apr. 4, 2018, and are incorporated herein by reference in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A compound of Formula (I) or a pharmaceutically acceptable salt, solvate, or hydrate thereof:

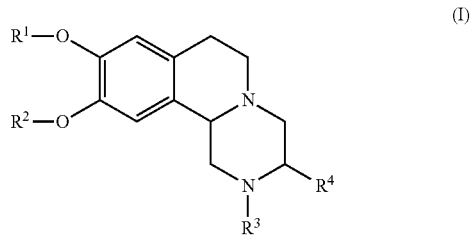

(I)

wherein:
$R^1$ and $R^2$ are independently lower alkyl, lower cycloalkyl, or lower cycloalkylalkyl, wherein each lower alkyl, lower cycloalkyl, and lower cycloalkylalkyl is independently unsubstituted or substituted with one or more halo, cyano, or loweralkoxy;
$R^3$ is lower alkyl; and
$R^4$ is lower alkyl or lower cycloalkylalkyl.

2. The compound of claim 1, selected from a compound of Formula (II) or a pharmaceutically acceptable salt, solvate, or hydrate thereof:

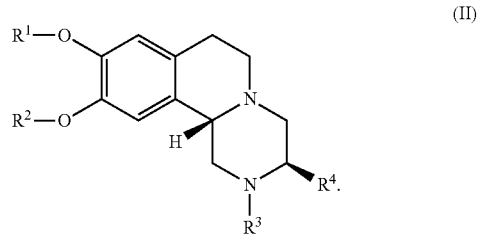

(II)

3. The compound of claim 1, wherein $R^2$ is $C_{1-4}$ saturated alkyl.

4. The compound of claim 3, wherein $R^2$ is methyl.

5. The compound of claim 2, wherein $R^3$ is methyl, ethyl, n-propyl, iso-propyl, iso-butyl, or neo-pentyl.

6. The compound of claim 5, wherein $R^3$ is methyl.

7. The compound of claim 2, wherein $R^4$ is $C_{1-6}$ saturated alkyl.

8. The compound of claim 2, wherein $R^4$ is iso-butyl, neo-pentyl, —$CH_2$-cyclopropyl, or —$CH_2$-cyclobutyl.

9. The compound of claim 1, selected from a compound of Formula (V) or a pharmaceutically acceptable salt, solvate, or hydrate thereof:

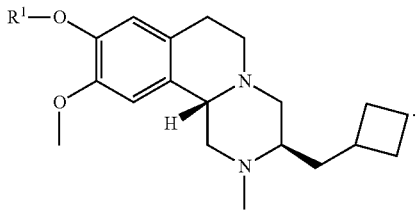
(V)

10. The compound of claim 1, selected from a compound of Formula (VI) or a pharmaceutically acceptable salt, solvate, or hydrate thereof:

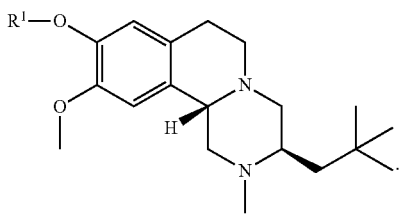
(VI)

11. The compound of claim 2, wherein $R^1$ is lower alkyl or lower cycloalkyl, wherein each lower alkyl and lower cycloalkyl is independently unsubstituted or substituted with one or more halo, cyano, or lower alkoxy.

12. The compound of claim 2, wherein $R^1$ is methyl, ethyl, n-propyl, iso-propyl, iso-butyl, neo-pentyl, —(CH$_2$)$_3$CH$_2$F, —(CH$_2$)$_2$CH$_2$F, —CH$_2$CH$_2$F, —(CH$_2$)$_4$CF$_3$, —(CH$_2$)$_3$CF$_3$, —(CH$_2$)$_2$CF$_3$, —CH$_2$CF$_3$, cyclopropyl, cyclobutyl, —CH$_2$-cyclopropyl, —CH$_2$-cyclobutyl, or —CH$_2$-cyclopentyl.

13. The compound of claim 2, wherein $R^1$ is $C_{1-4}$ saturated alkyl substituted with $C_{1-4}$ saturated alkoxy, $R^1$ is $C_{1-4}$ saturated alkyl substituted with a cyano group, or $R^1$ is lower cycloalkylalkyl substituted with halo.

14. The compound of claim 13, wherein $R^1$ is —CH$_2$CH$_2$OCH$_3$ or $R^1$ is —CH$_2$CH$_2$CH$_2$CN.

15. The compound of claim 13, wherein $R^1$ is:

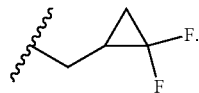 [SMILES: *CC1CC1(F)F]

16. The compound of claim 1, selected from

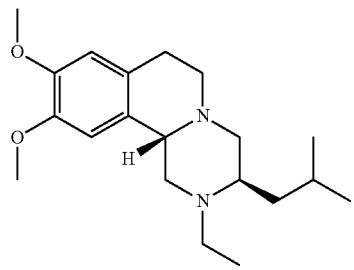

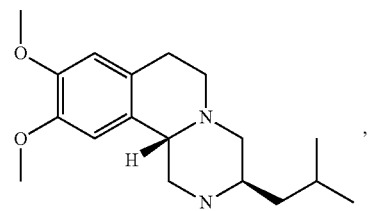

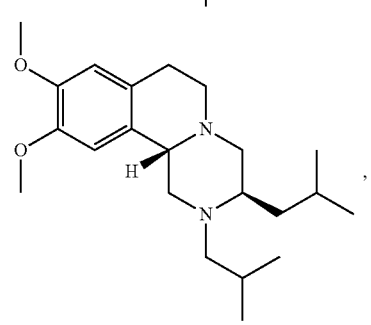

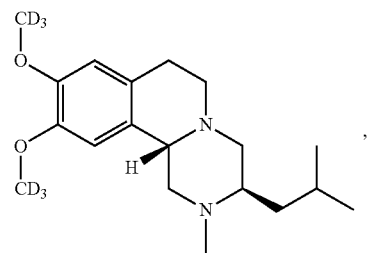

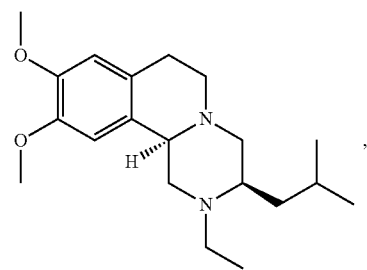

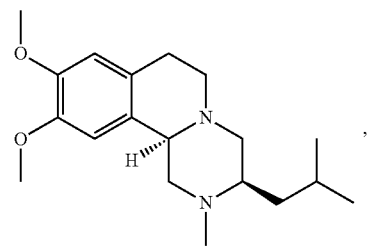

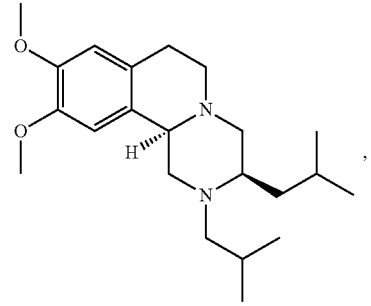

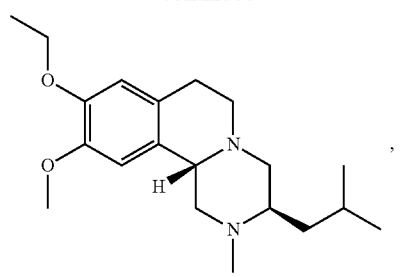
,
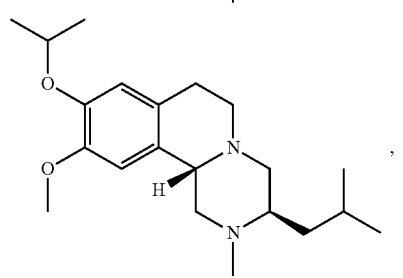
,
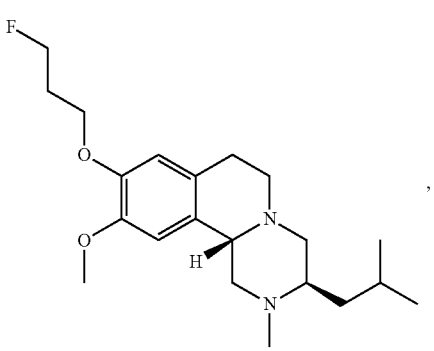
,
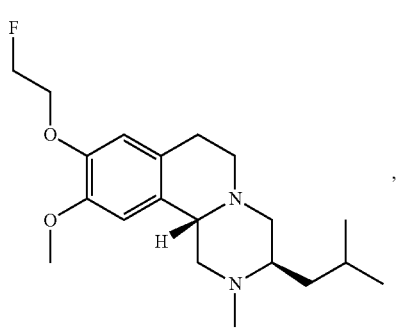
,
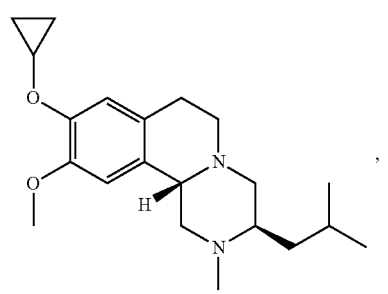
,
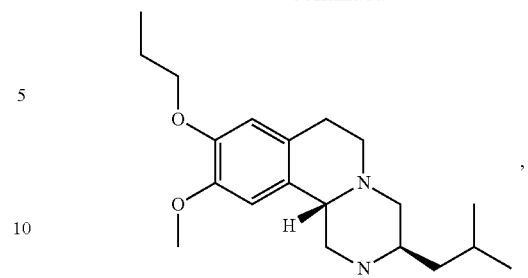
,
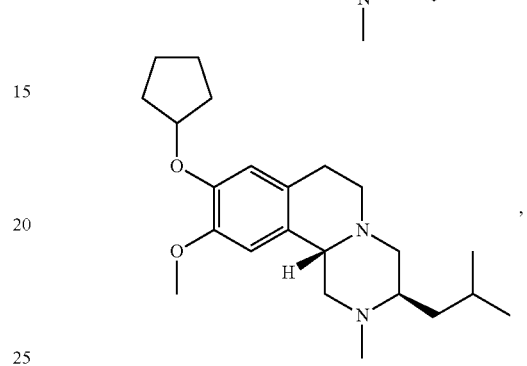
, 87
-continued
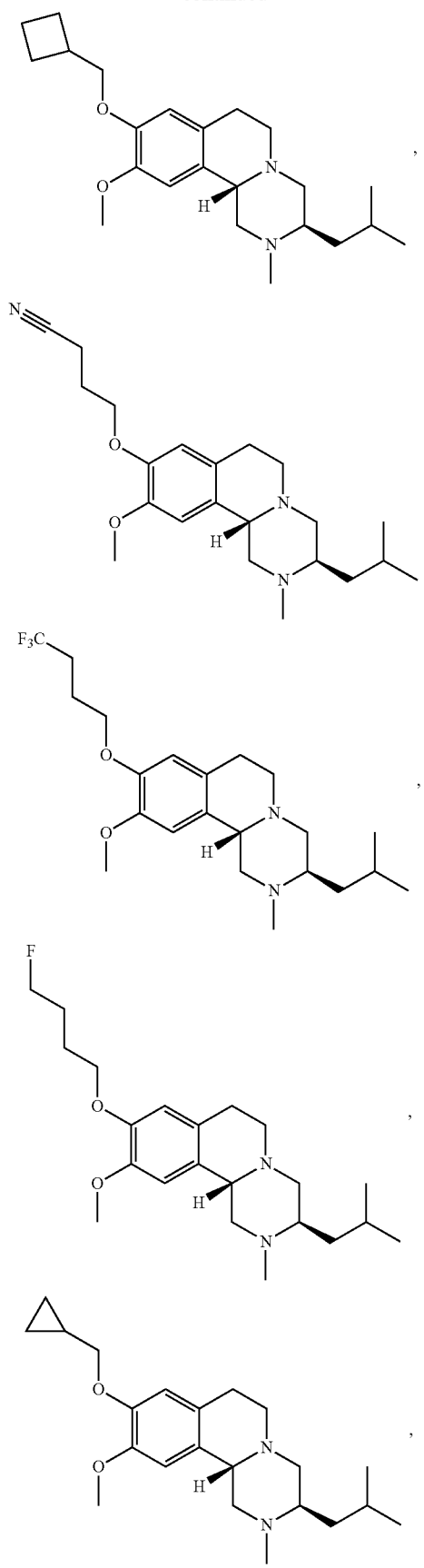
88
-continued
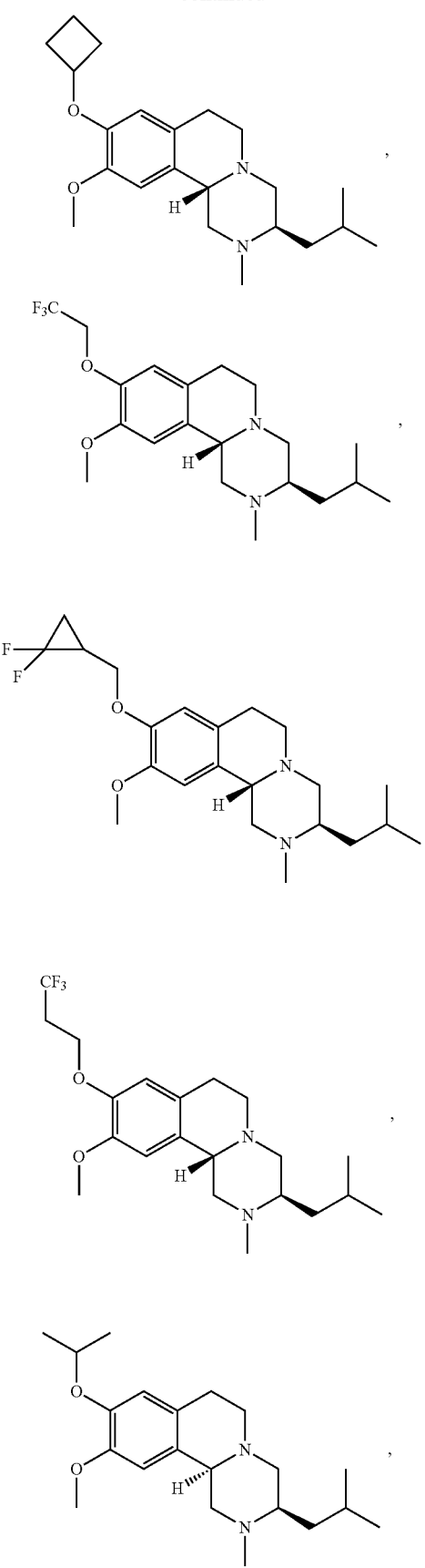

89
-continued
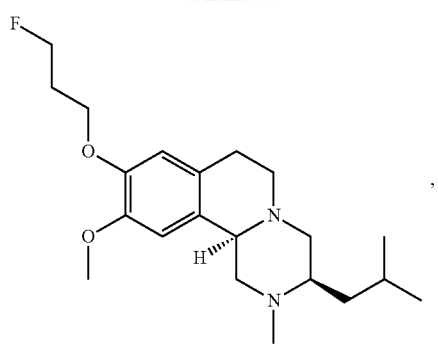
,
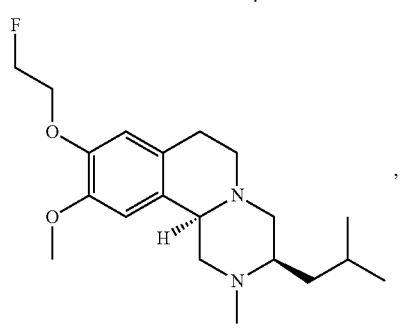
,
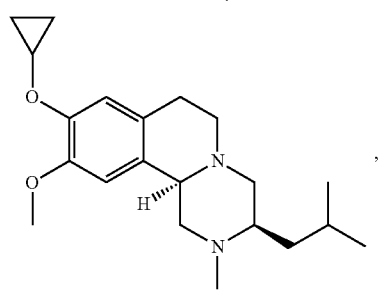
,
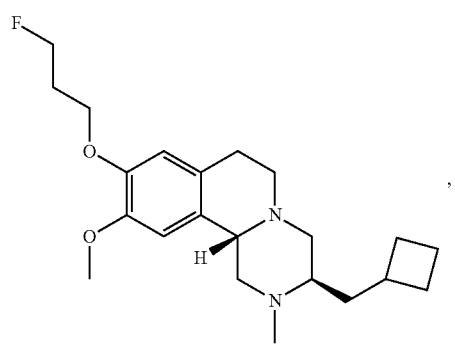
,
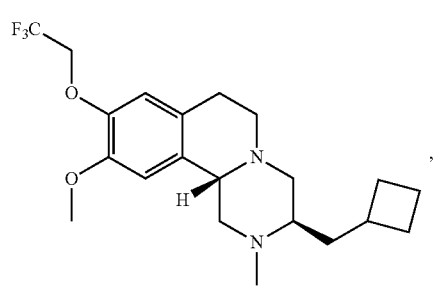
,
90
-continued
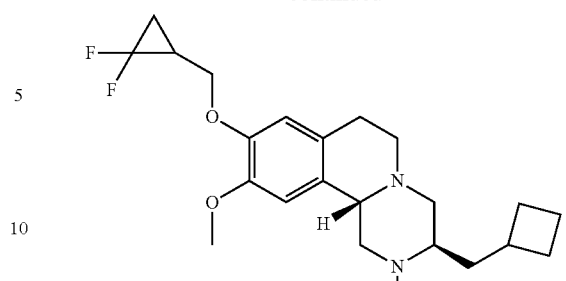
,
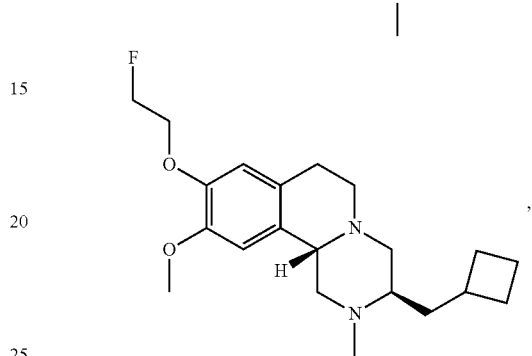
,
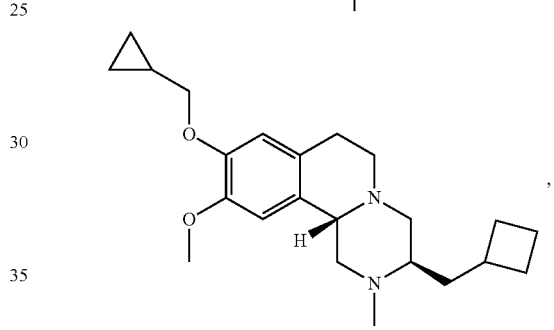
,
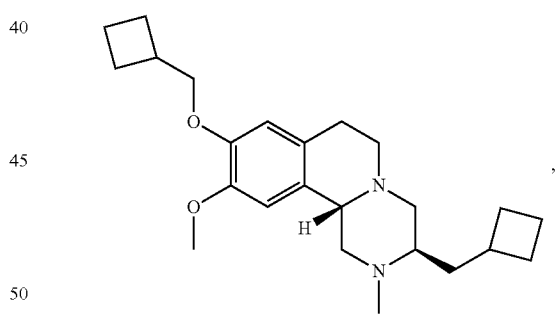
,
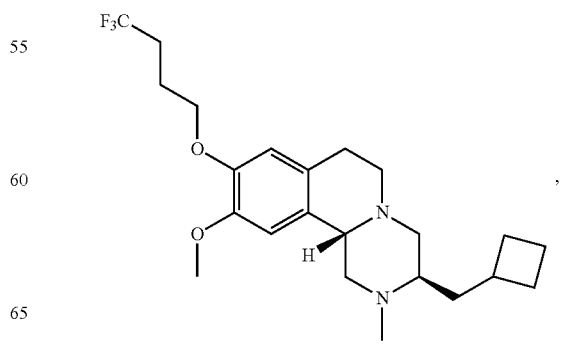
,

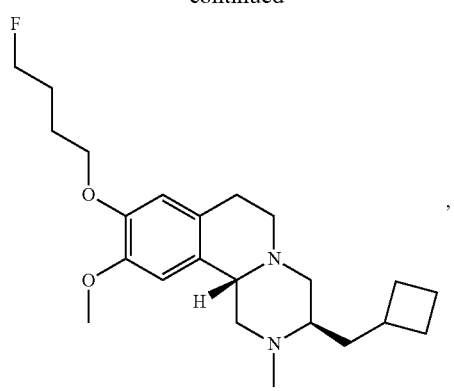
,
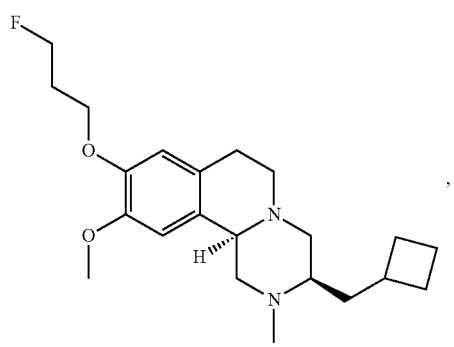
,
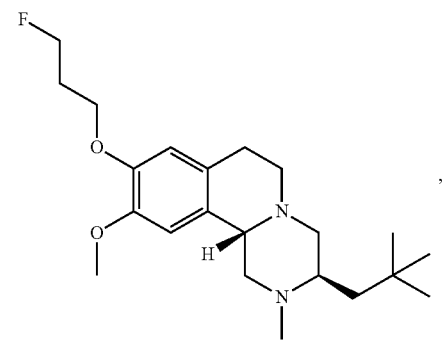
,
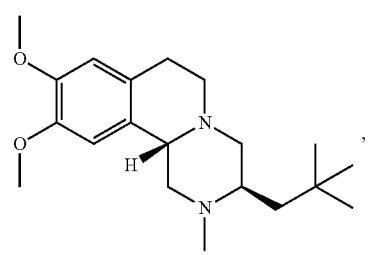
,
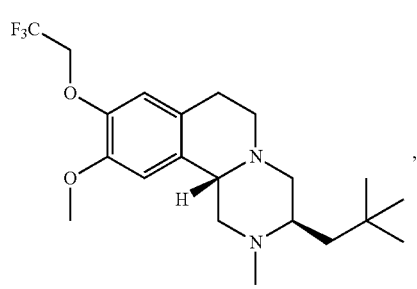
,
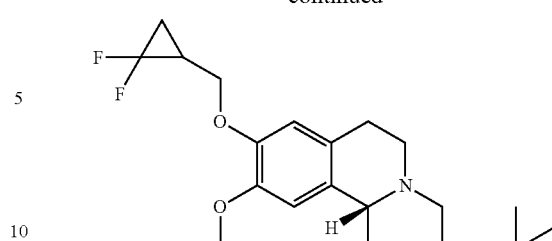
,
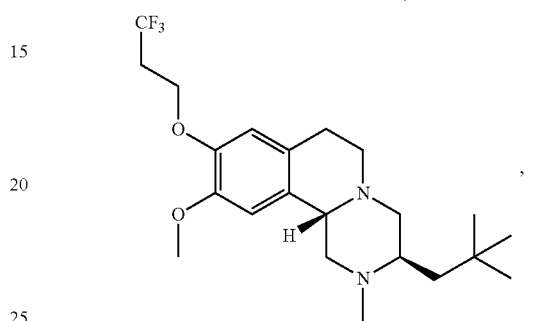
,
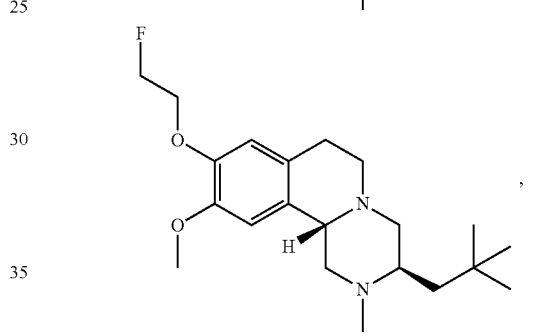
,
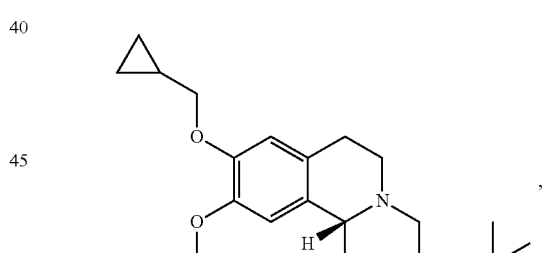
,
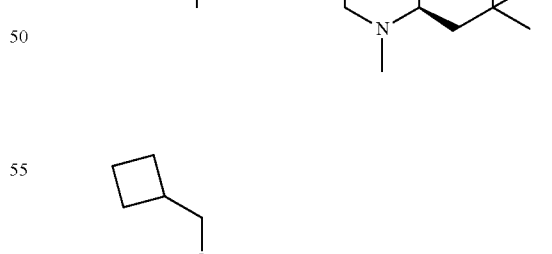
,
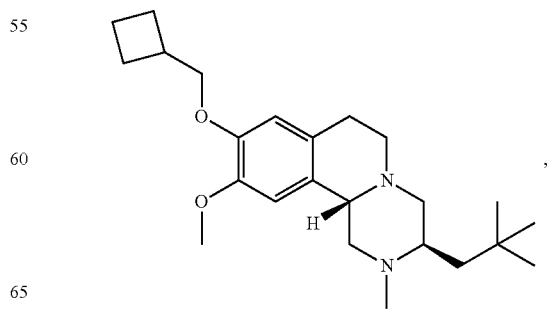
, 93
-continued
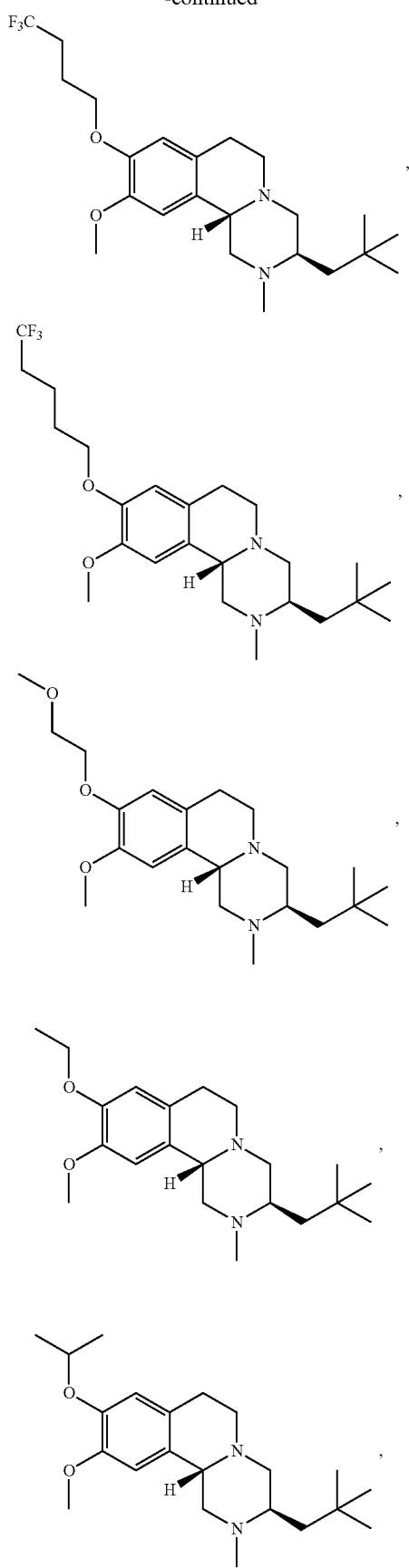
94
-continued
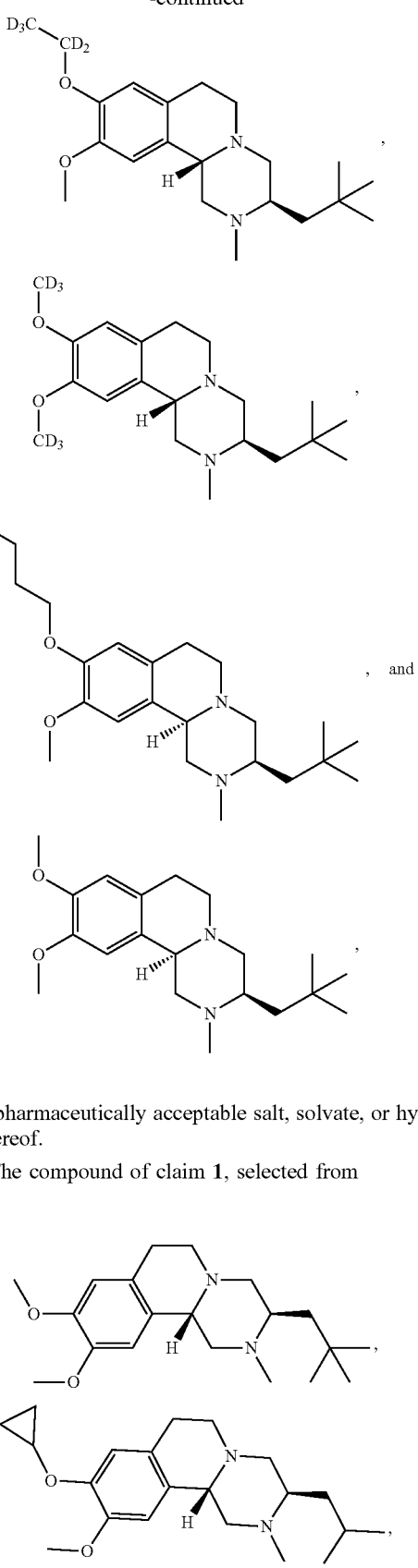
or a pharmaceutically acceptable salt, solvate, or hydrate thereof.
17. The compound of claim 1, selected from
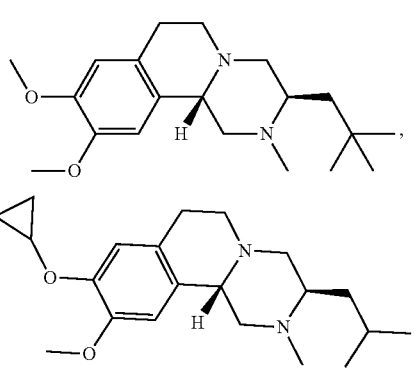

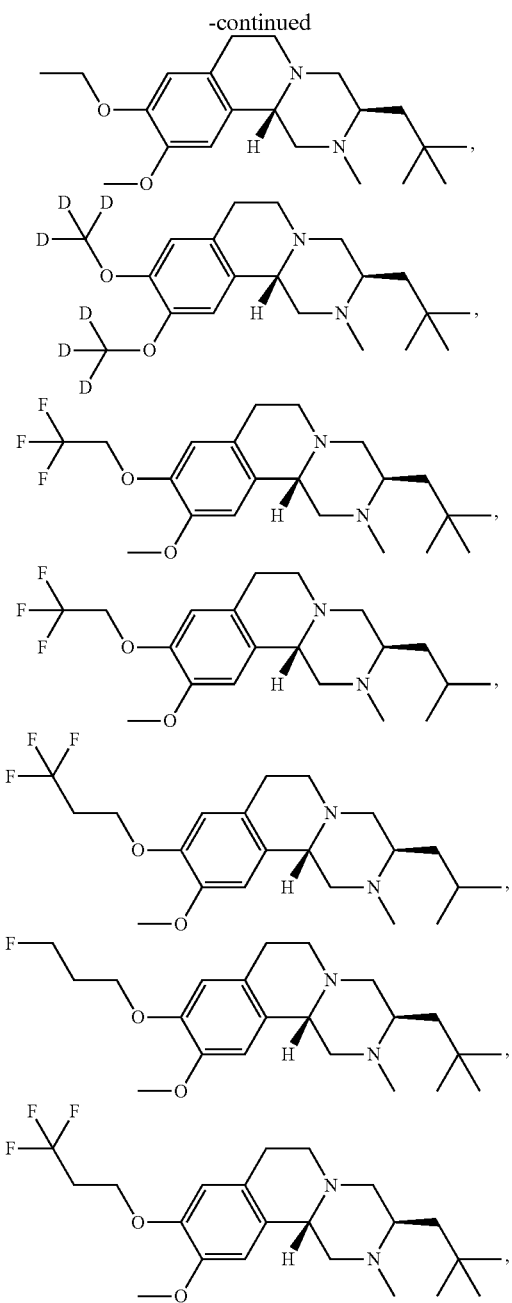

or a pharmaceutically acceptable salt, solvate, or hydrate thereof.

18. The compound of claim 17, selected from

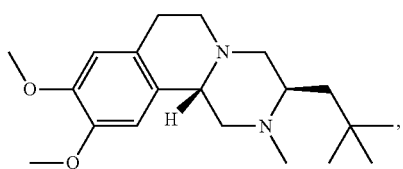 [SMILES: COc1cc2c(cc1OC)[C@H]1CN(C)[C@H](CC(C)(C)C)CN1CC2]

or a pharmaceutically acceptable salt, solvate, or hydrate thereof.

19. The compound of claim 18, which is a diphosphate salt, or a solvate or hydrate thereof.

20. The compound of claim 17, selected from

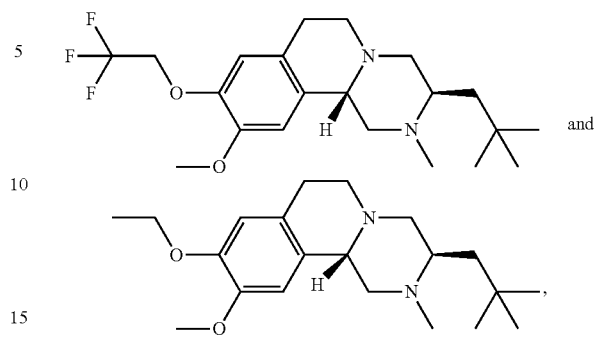

or a pharmaceutically acceptable salt, solvate, or hydrate thereof.

21. The compound of claim 17, which is

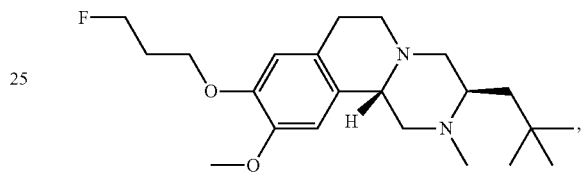

or a pharmaceutically acceptable salt, solvate, or hydrate thereof.

22. The compound of claim 17, which is

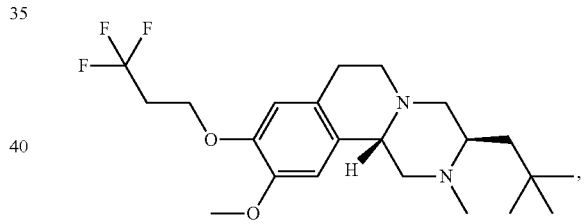

or a pharmaceutically acceptable salt, solvate, or hydrate thereof.

23. The compound of claim 17, which is

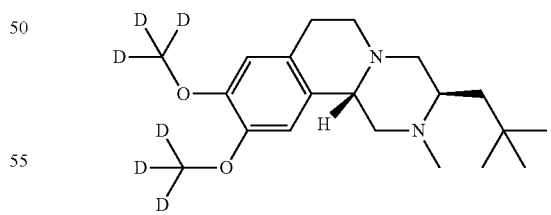

or a pharmaceutically acceptable salt, solvate, or hydrate thereof.

24. A pharmaceutical composition comprising one or more compounds of claim 2 in combination with one or more pharmaceutically acceptable excipients and/or diluents.

25. A process for preparing a composition comprising admixing a compound of claim 2 and one or more pharmaceutically acceptable excipients and/or diluents.

26. A process for preparing a compound of Structure vi having formula:

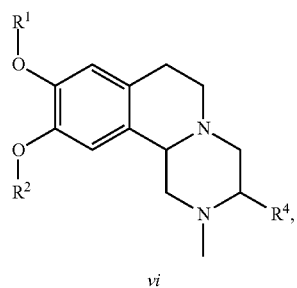

vi or a salt thereof,
wherein:
R¹ and R² are independently lower alkyl, lower cycloalkyl, or lower cycloalkylalkyl, wherein each lower alkyl, lower cycloalkyl, and lower cycloalkylalkyl is independently unsubstituted or substituted with one or more halo, cyano, or lower alkoxy; and
R⁴ is lower alkyl or lower cycloalkylalkyl,
comprising:
a) reacting a compound of Structure iii, having the formula:

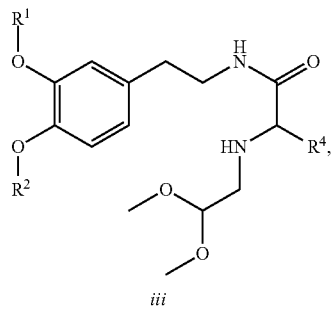

iii or a salt thereof,
with paraformaldehyde under reductive amination conditions to provide a compound of Structure iv having the formula:

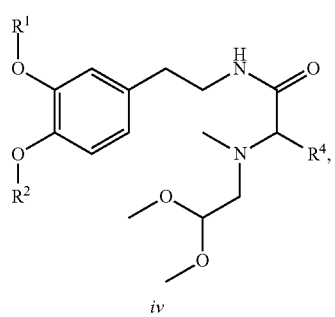

iv or a salt thereof;
b) cyclizing the compound of Structure iv, or a salt thereof, under acidic conditions, to provide a compound of Structure v, having the formula:

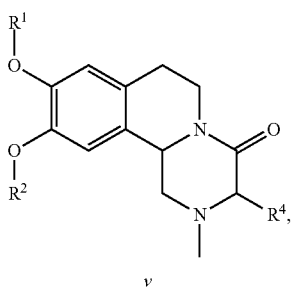

v or a salt thereof; and
c) reducing the compound of Structure v, or a salt thereof, to provide the compound of Structure vi, or a salt thereof.

27. The process of claim 26, wherein:
in step a) the reacting the compound of Structure iii, or a salt thereof, under reductive amination conditions comprises reacting the compound of Structure iii, or a salt thereof, with paraformaldehyde in the presence of acetic acid, and then treating with a reducing agent;
in step b) cyclizing the compound of Structure iv, or a salt thereof, under acidic conditions comprises reacting the compound of Structure iv with concentrated sulfuric acid; and
in step c) the reducing the compound of Structure v, or a salt thereof, is performed using a reducing agent where the reducing agent is lithium aluminum hydride.

28. A process for preparing Compound 11-2 having formula:

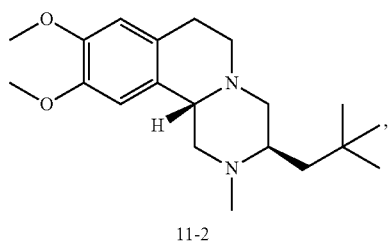 [SMILES: COc1cc2c(cc1OC)[C@H]1CN(C)[C@H](CC(C)(C)C)CN1CC2]

11-2 or a salt thereof,
comprising:
a) reacting a compound of Structure 11b, having the formula:

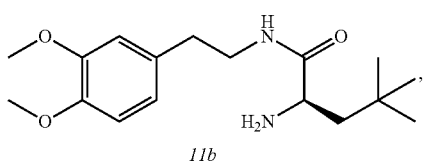 [SMILES: COc1ccc(CCNC(=O)[C@H](N)CC(C)(C)C)cc1OC]

11b or a salt thereof, with 2,2-dimethoxyacetaldehyde under reductive amination conditions to provide a compound of Structure 11c having the formula:

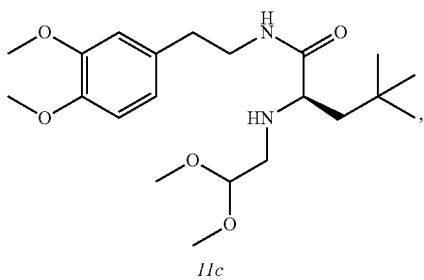 [SMILES: COc1ccc(CCNC(=O)[C@@H](CC(C)(C)C)NCC(OC)OC)cc1OC]

11c or a salt thereof;

b) reacting the compound of Structure 11c, or a salt thereof, with paraformaldehyde under reductive amination conditions to provide a compound of Structure 11d having the formula:

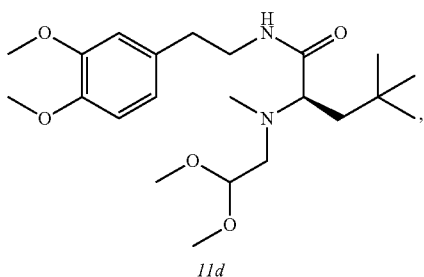 [SMILES: COc1ccc(CCNC(=O)[C@@H](CC(C)(C)C)N(C)CC(OC)OC)cc1OC]

11d or a salt thereof;

c) cyclizing the compound of Structure 11d, or a salt thereof, under acidic conditions to provide a compound of Structure 11e, having the formula:

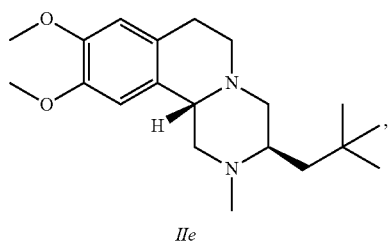 [SMILES: COc1cc2c(cc1OC)[C@H]1CN(C)[C@H](CC(C)(C)C)CN1CC2]

11e or a salt thereof; and d) reducing the compound of Structure 11e, or a salt thereof, to provide Compound 11-2, or a salt thereof.

29. The process of claim 28, wherein:

in step a) the reacting the compound of Structure 11b, or a salt thereof, under reductive amination conditions comprises reacting the compound of Structure 11b, or a salt thereof, with 2,2-dimethoxyacetaldehyde in the presence of acetic acid, and then treating with sodium cyanoborohydride;

in step b) the reacting the compound of Structure 11c, or a salt thereof, under reductive amination conditions comprises reacting the compound of Structure 11c, or a salt thereof, with paraformaldehyde in the presence of acetic acid, and then treating with sodium cyanoborohydride;

in step c) the cyclizing the compound of Structure 11d, or a salt thereof, under acidic conditions comprises treating the compound of Structure 11d, or a salt thereof, with concentrated sulfuric acid; and in step d) the reducing the compound of Structure 11e, or a salt thereof, is performed using a reducing agent where the reducing agent is lithium aluminum hydride.

* * * * *